United States Patent
Wu et al.

(10) Patent No.: US 7,476,764 B2
(45) Date of Patent: Jan. 13, 2009

(54) PHENYLCARBOXYAMIDES AS BETA-SECRETASE INHIBITORS

(75) Inventors: Yong-Jin Wu, Madison, CT (US); Yunhui Zhang, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/494,145

(22) Filed: Jul. 27, 2006

(65) Prior Publication Data

US 2007/0032470 A1 Feb. 8, 2007

Related U.S. Application Data

(60) Provisional application No. 60/705,610, filed on Aug. 4, 2005.

(51) Int. Cl.
 C07C 233/00 (2006.01)
 A01N 37/18 (2006.01)
(52) U.S. Cl. .............. 564/156; 564/183; 514/616; 514/617
(58) Field of Classification Search ............... None
 See application file for complete search history.

(56) References Cited

U.S. PATENT DOCUMENTS 7,214,715 B2 * 5/2007 Beck et al. ............ 514/616

FOREIGN PATENT DOCUMENTS

WO  WO 2004/043916  5/2004
WO  WO 2004/050619  6/2004

OTHER PUBLICATIONS

Maillard et al., caplus an: 2002:31402.*
Maillard et al., caplus AN 2002:31402.*
Hussain, I. et al., "Identification of a Novel Aspartic Protease (Asp 2) as β-Secretase", *Mol. Cell. Neurosci*, (1999) 14: 419-427.
Lin, X. et al., "Human aspartic protease memapsin 2 cleaves the β-secretase site of β-amyloid precursor protein", Proceedings of the National Academy of Sciences of the USA, (2000) 97: 1456-1460.
Luo, Y., et al., "Mice deficient in BACE1, the Alzheimer's β-secretase, have normal phenotype and abolished β-amyloid generation", *Nature Neuroscience* (2001) 4: 231-232.
Roberds, S.L. et al., "BACE knockout mice are healthy despite lacking the primary β-secretase activity in brain: implications for Alzheimer' disease therapeutics", *Human Molecular Genetics* (2001) 10: 1317-1324.
Seiffert, D.; et al., "Presenilin-1 and -2 are molecular targets for γ-secretase inhibitors", *J. Biol. Chem.* (2000) 275, 34086-34091.
Selkoe, D. J., "Alzheimer's Disease: Genes, Proteins, and Therapy", *Physiol. Rev.* (2001) 81, 741-766.

Selkoe, D. J., "Biochemical Analyses of Alzheimer's Brain Lesions lead to the Identification of αβand its Precursor", *Ann, Rev. Cell Biol.* (1994) 10: 374-403.
Sinha, S., et al., "Purification and cloning of amyloid precursor protein β-secretase from human brain", *Nature (London)* (1999) 402: 537-540.
Stachel, S.J., et al., , "Structure-Based Design of Potent and Selective Cell-Permeable Inhibitors of Human β-Secretase (BACE-1)", *J. Med. Chem.* (2004) 47: 6447-6450.
Thaisrivongs, S. et al., "Conformationally Constrained Renin Inhibitory Peptides: α-Lactam-Bridged Dipeptide Isostere as Conformational Restrictions", *J. Med. Chem.* (1988) 31: 1369-1376.
Thaisrivongs, et al., "Renin inhibitory peptides: a study of structural modifications in the peptide backbone", *J. Hypertension* (1989), 7 Suppl. 2: S21-S23.
Thal, D. R., et al., "Two types of Sporadic Cerebral Amyloid Angiopathy", *J. Neuropath. and Exper. Neurology* (2002) 61: 282-293.
Vassar, R., et al., "β-Secretase cleavage of Alzheimer's amyloid precursor protein by the transmembrane aspartic protease BACE", *Science* (1999) 286: 735-741.
Walsh, D. M., et al., "Naturally secreted oligomers of amyloid β protein potently inhibit hippocampal long-term potentiation in vivo", *Nature* (2002) 416, 535-539.
Wolfe, M. S., "Secretase Targets for Alzheimer's Disease: Identification and Therapeutic Potential", *J. Med. Chem.* (2001) 44, 2039-2060.
Yan, R. et al., "Membrane-anchored aspartyl protease with Alzheimer's disease β-secretase activity", *Nature* (1999) 402: 533-537.

* cited by examiner

*Primary Examiner*—Rebecca Anderson
*Assistant Examiner*—Sun Jae Y Loewe
(74) *Attorney, Agent, or Firm*—John F. Levis; Aldo A. Algieri

(57) ABSTRACT

There is provided a series of novel phenylcarboxyamides of Formula (I)

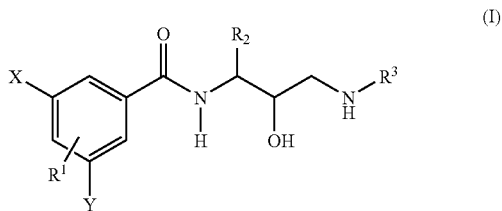

or a stereoisomer; or a pharmaceutically acceptable salt thereof, wherein $R^1$, $R^2$, $R^3$, X and Y as defined herein, their pharmaceutical compositions and methods of use. These novel compounds inhibit the processing of amyloid precursor protein (APP) by β-secretase and, more specifically, inhibit the production of Aβ-peptide. The present disclosure is directed to compounds useful in the treatment of neurological disorders related to β-amyloid production, such as Alzheimer's disease and other conditions affected by anti-amyloid activity.

9 Claims, No Drawings

PHENYLCARBOXYAMIDES AS BETA-SECRETASE INHIBITORS

CROSS-REFERENCE TO RELATED APPLICATIONS

This is a non-provisional application which claims the benefit of U.S. Provisional Application No. 60/705,610 filed Aug. 4, 2005.

FIELD OF THE DISCLOSURE

This patent application provides novel substituted phenylcarboxyamides having drug and bio-affecting properties, their pharmaceutical compositions and method of use. In particular, the disclosure is concerned with a series of novel phenylcarboxyamides which are inhibitors of the β-amyloid peptide (β-AP) production, thereby acting to prevent the accumulation of amyloid protein deposits in the brain and, therefore, are useful in the treatment of neurological disorders related to β-amyloid production. More particularly, the present disclosure relates to the treatment of Alzheimer's Disease (AD) and similar diseases.

BACKGROUND

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Selkoe, D. J. *Ann. Rev. Cell Biol.*, 1994, 10: 373-403).

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Biochemical and immunological studies reveal that the dominant proteinaceous component of the amyloid plaque is an approximately 4.2 kilodalton (kD) protein of about 39 to 43 amino acids. This protein is designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Compelling evidence accumulated during the last decade reveals that Aβ is an internal polypeptide derived from a type 1 integral membrane protein, termed β-amyloid precursor protein (APP) (Selkoe, D. *Physiol. Rev.* 2001, 81, 741-766; Wolfe, M. *J. Med. Chem.* 2001, 44, 2039-2060). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, D.; Bradley, J. et al., *J. Biol. Chem.* 2000, 275, 34086-34091).

In addition to AD, excess production and/or reduced clearance of Aβ causes cerebral amyloid angiopathy (CAA) (reviewed in Thal, D., Gherbremedhin, E. et al., *J. Neuropath. Exp. Neuro.* 2002, 61, 282-293). In these patients, vascular amyloid deposits cause degeneration of vessel walls and aneurysms that may be responsible for 10-15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

A logical approach to reducing Aβ levels is to interfere with the action of the secretases that are directly involved in the cleavage of APP to Aβ. The β-secretase enzyme (BACE) is responsible for cleaving APP and forms the amino-terminus of Aβ, initiating the amyloidogenic pathway. The BACE enzyme is a transmembrane aspartyl protease and was described in the literature by several independent groups [see Hussain, I. et al., (1999) *Mol. Cell. Neurosci.*, 14: 419-427; Lin, X. et al., (2000) *Proceedings of the National Academy of Sciences of the United States of America*, 97: 1456-1460; Sinha, S., et al., (1999) *Nature (London)*, 402: 537-540; Vassar, R., et al., (1999) *Science (Washington, D.C.)*, 286: 735-741; Walsh, D. M. et al., (2002) *Nature* 416, 535-539; Wolfe, M. S., (2001) *J. Med. Chem.* 44, 2039-2060; Yan, R. et al., (1999) *Nature (London)*, 402: 533-537].

Removal of BACE activity in mice by gene targeting completely abolishes Aβ production [see Luo, Y., et al., (2001) *Nature Neuroscience*, 4: 231-232; Roberds, S. L. et al., (2001) *Human Molecular Genetics*, 10: 1317-1324].

BACE−/− mice also show no detectable negative phenotypes, suggesting that disruption of BACE-mediated cleavage of APP does not produce additional undesired effects. This demonstrates that a drug substance capable of inhibiting β-secretase activity should lower or halt the synthesis of Aβ and should provide a safe treatment for Alzheimer's disease.

PCT Publication WO 2004/043916, published May, 27, 2004, discloses phenylcarboxamides as beta-secretase inhibitors. Published article Thaisrivongs et al., *J. Hypertension* (1989), Suppl. (2), S21-S23 discusses related rennin inhibitors.

PCT Publication WO 2004/050619, published Jun. 19, 2004, discloses hydroxyamine derivatives as beta-secretase inhibitors.

Published article Thaisrivongs, S. et al., *J. Med. Chem.* (1988), 31(7): 1369-76 discusses related rennin inhibitors and Stachel, S. J. et al., *J. Med. Chem.* (2004) 47: 6447-6450 discusses inhibitors of human beta-secretase.

At present there remains an urgent need to develop pharmaceutical agents capable for effective treatment in halting, slowing, preventing, and/or reversing the progression of Alzheimer's disease. Compounds that are effective inhibitors of beta-secretase, that inhibit beta-secretase mediated cleavage of APP, that are effective inhibitors of Aβ protein production by beta-secretase, and/or are effective in reducing soluble Aβ protein, amyloid beta deposits or amyloid beta plaques, are needed for effective treatment in halting, slowing, preventing, and/or reversing neurological disorders related to Aβ protein production, such as Alzheimer's disease.

SUMMARY OF THE DISCLOSURE

A series of phenylcarboxyamide derivatives having the Formula (I)

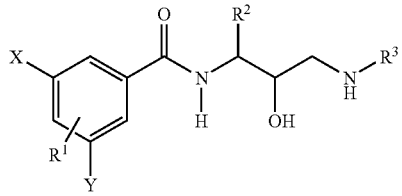

or a stereoisomer; or a pharmaceutically acceptable salt thereof, wherein $R^1$, $R^2$, $R^3$, X and Y as defined below are effective inhibitors of the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds or a pharmaceutical composition containing a therapeutically effective amount of at least one of these compounds to patients suffering from, or susceptible to, these conditions involves reducing β-AP available for accumulation and deposition in brains of these patients.

DETAILED DESCRIPTION

The present application comprises compounds of Formula I, their pharmaceutical formulations, and their use in inhibiting β-AP production in patients suffering from or susceptible to AD or other disorders resulting from β-AP accumulation in brain tissue. The compounds of Formula I which include stereoisomers and pharmaceutically acceptable salts thereof have the following formula and meanings:

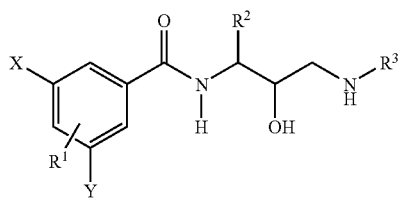

wherein
X is selected from the group consisting of

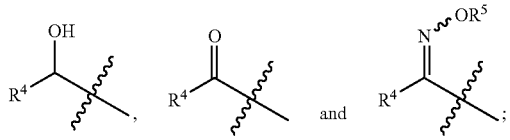

Y is —C(O)NR$^6$R$^7$, C(O)NH—C$_{1-3}$alkyl-aryl, C(O)NH—C$_{1-3}$alkyl-heteroaryl, —SO$_2$R$^6$, —NR$^6$S(O)$_m$R$^7$,

[structures of two cyclic groups containing N with (CH$_2$)$_n$ substituents, one with S(O)$_m$ and one with C=O]

$R^1$ is H, CF$_3$, C$_{1-4}$alkyl, OC$_{1-4}$alkyl, NH$_2$, NHC(O)C$_{1-4}$alkyl, CN or halogen;
$R^2$ and $R^3$ each are independently —C$_{1-4}$alkyl-aryl or —C$_{1-4}$ alkyl-heteroaryl;
$R^4$, $R^6$ and $R^7$ are each independently C$_{1-6}$ alkyl;
$R^5$ is C$_{1-6}$alkyl, allyl or benzyl;
m is 1 or 2; and
n is an integer from 1 to 3;
or a nontoxic pharmaceutically acceptable salt thereof.

The present application also provides a method for the treatment or alleviation of disorders associated with β-amyloid peptide, especially Alzheimer's Disease, cerebral amyloid angiopathy and Down's Syndrome, which comprises administering together with a conventional adjuvant, carrier or diluent a therapeutically effective amount of a compound of Formula (I) or a pharmaceutically acceptable salt thereof.

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is well known in the art, see Colin Dingwall, *Journal of Clinical Investigation*, November 2001, 108 (9): 1243-1246; as well as PCT international patent application WO 01/92235, published Dec. 6, 2001, herein incorporated by reference in its entirety.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The term "substituted," as used herein and in the claims, means that any one or more hydrogens on the designated atom is replaced with a selection from the indicated group, provided that the designated atom's normal valency is not exceeded, and that the substitution results in a stable compound.

As used herein and in the claims, "alkyl" or "alkylene" is intended to include both branched and straight-chain saturated aliphatic hydrocarbon groups having the specified number of carbon atoms; for example, "C$_{1-3}$alkyl, C$_{1-4}$alkyl, and C$_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, pentyl and hexyl. Preferred "alkyl" group, unless otherwise specified, is "C$_{1-4}$ alkyl". Additionally, unless otherwise specified, "propyl" denotes n-propyl or i-propyl; "butyl" denotes n-butyl, i-butyl, sec-butyl, or t-butyl.

As used herein and in the claims, "halogen" refers to fluoro, chloro, bromo, and iodo. Unless otherwise specified, preferred halogens are fluoro and chloro. "Counterion" is used to represent a small, negatively charged species such as chloride, bromide, hydroxide, acetate, sulfate, and the like.

As used herein and in the claims, "aryl" is intended to include monocyclic aromatic rings, e.g. phenyl, and bicyclic aromatic rings, e.g. naphthyl, and carbocyclic benzofused rings, e.g. $C_{3-8}$ cycloalkyl fused to a phenyl ring, such as dihydroindenyl or tetrahydronaphthalenyl, optionally substituted by one or more $C_{1-4}$alkyl, halogen, —$OCF_3$. hydroxyl, $C_{1-4}$alkoxy, cyano, nitro, amino or $NHC(O)C_{1-4}$alkyl.

As used herein and in the claims, "heteroaryl" is intended to include mono- and bicyclic heterocyclic aromatic rings containing 1-4 heteroatoms selected from nitrogen, oxygen, and sulfur. Examples of monocyclic heterocyclic aromatic rings include thienyl, furyl, pyrrolyl, triazolyl, imidazolyl, oxazolyl, thiazolyl, oxadiazolyl, isothiazolyl, isoxazolyl, thiaziazolyl, pyrazolyl, pyrimidyl, pyridazinyl, pyrazinyl, pyridyl and tetrazolyl. Examples of bicyclic heterocyclic aromatic rings include quinolinyl, isoquinolinyl, quinazolinyl, quinoxalinyl, cinnolinyl, naphthyridinyl, indolyl, indazolyl, pyrrolopyridinyl, benzofuranyl, benzothienyl, benzimidazolyl, benzoxazolyl, benzisoxazolyl, benzothiazolyl, benzisothiazolyl, benzoxadiazolyl and benzothiadiazolyl, optionally substituted by one or more $C_{1-4}$alkyl, halogen, —$OCF_3$. hydroxyl, $C_{1-4}$alkoxy, cyano, nitro, amino or $NHC(O)C_{1-4}$alkyl.

The compounds described herein may have asymmetric centers. An example of a preferred stereochemical configuration is the isomer:

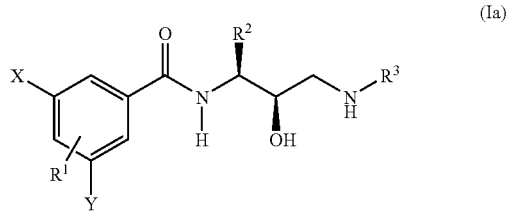

(Ia)

or pharmaceutically acceptable salt thereof, but is not intended to be limited to this example. It is understood, that whether a chiral center in an isomer is "R" or "S" depends on the chemical nature of the substituents of the chiral center. All configurations of compounds of the invention are considered part of the invention. Compounds of the present disclosure containing an asymmetrically substituted atom may be isolated in optically active or racemic forms. It is well known in the art how to prepare optically active forms, such as by resolution of racemic forms or by synthesis from optically active starting materials. Mixtures of isomers of the compounds of the examples or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereoisomeric salts with optically active salt-forming agents, separating the mixture into diastereomeric salts and converting the separated salts into the free compounds. The enantiomeric forms may also be separated by fractionation through chiral high pressure liquid chromatography columns. All chiral, diastereomeric, racemic forms and all geometric isomeric forms of a structure are intended, unless the specific stereochemistry or isomeric form is specifically indicated.

The phrase "non-toxic pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein and in the claims, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

In the method of the present application, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with β-amyloid peptide.

The compounds of the present application can be prepared in a number of ways well known to one skilled in the art of organic synthesis. The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In general, the present compounds represented by Formula I (Scheme 1) may be prepared by coupling, under standard conditions known to one skilled in the art, a substituted benzoic acid of formula 1 and a hydroxyethylamine of formula 2, wherein P represents a protecting group. The protecting groups include —C(O)O—Bu-t (Boc) and —C(O)O—CH$_2$Ph (CBZ). Other suitable protecting groups are disclosed in *Protection Groups in Organic Synthesis, Second Edition*, Theodore W. Greene and Peter G. M. Wuts (John Wiley & Sons, 1991) Chapter 7, for amino groups. The preferred conditions involved 1-(3-dimethyl-aminopropyl)-3-ethylcarbodiimide hydrochloride (EDAC.HCl), 1-hydroxybenzotriazole (HOBT) and diisopropylethylamine (DIPEA) or 1-(3-dimethyl-aminopropyl)-3-ethylcarbodiimide hydrochloride (EDAC.HCl), 2-(dimethylamino)pyridine (DMAP) and triethylamine (TEA). Compounds of formula 3 underwent deprotection to give compounds of formula I.

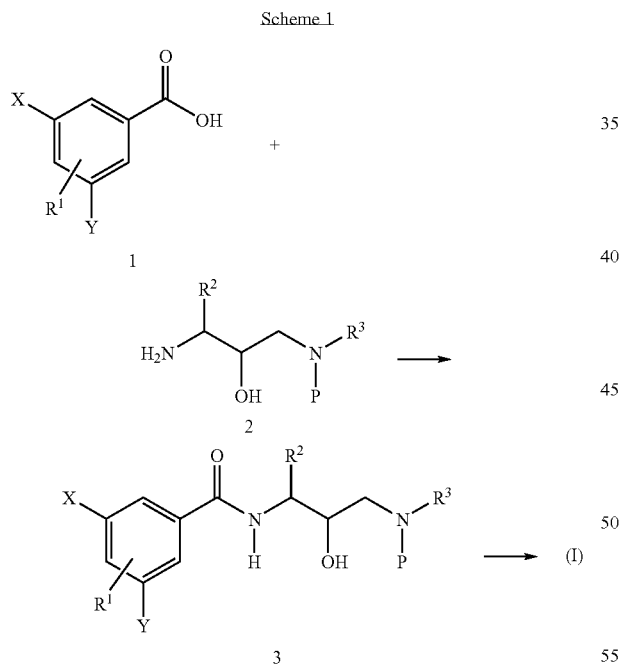

Scheme 2 shows the synthesis of compounds of formula I, wherein X is —C(O)R$^4$ and Y is —C(O)NR$^6$R$^7$. Compounds of formula 4 are reduced, under standard conditions known to one skilled in the art, to give amines of formula 5, which are converted to bromides of formula 6, upon treatment with tert-butyl nitrite in the presence of CuCl$_2$ or CuBr$_2$ under thermal conditions or tert-butyl thionitrite or tert-butyl thionitrate in the presence of CuCl$_2$ or CuBr$_2$ at room temperature. Compounds of formula 6 are converted to those of formula 7 under standard conditions known to one skilled in the art. Arylboronates of formula 8 are made through palladium-catalyzed coupling of 7 with bis(pinacolato)diboron using the procedures of Zhang et. al. (J. Org. Chem., 2003, 68, 3729-3732). Compounds of formula 8 undergoes palladium-catalyzed cross-coupling with acid chlorides of formula R$^4$C(O)Cl to give compounds of formula 9 following the procedures of Haddach and McCarthy (Tetrahedron Lett., 1999, 40, 3109-3112). Compounds of formula 9 are hydrolyzed under basic conditions to give acids of formula 10, which are converted to compounds of formula Ib via 11 by coupling with amine 2 as shown in Scheme 2, followed by removal of the protecting group.

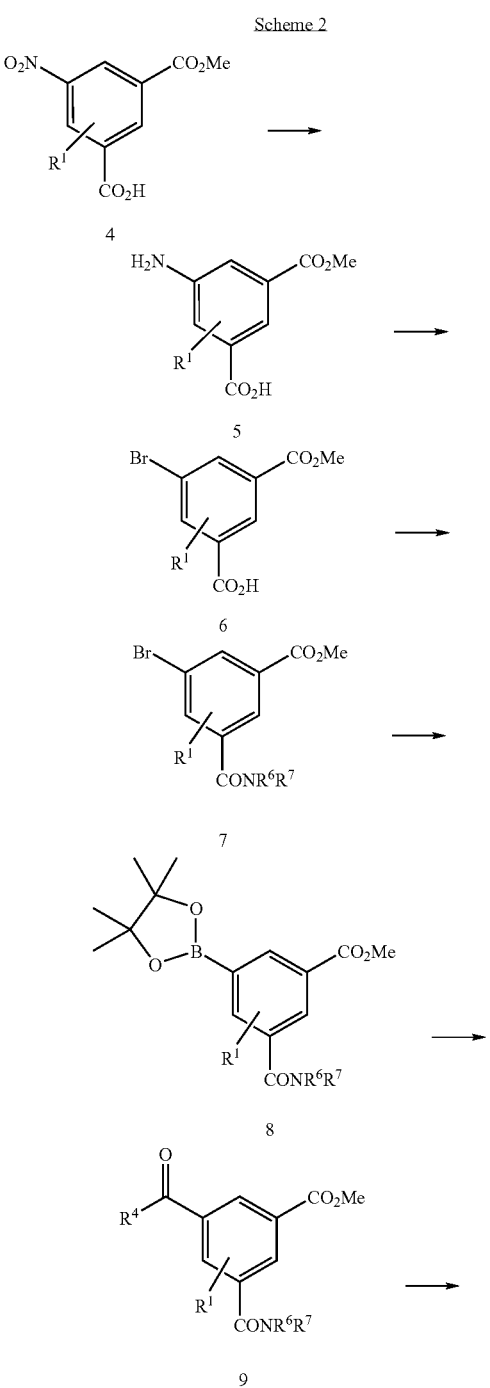

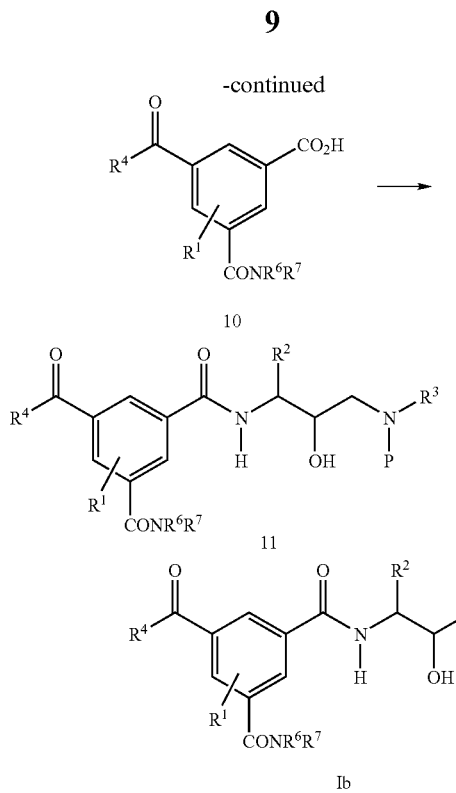

Scheme 5 shows the synthesis of compounds of formula I wherein X is —CH(OH)R⁴ and Y is —C(O)NR⁶R⁷. Treatment of 9, prepared according to Scheme 2, with a reducing agent such as sodium borohydride in methanol or ethanol provides 12. Hydrolysis of 12 under basic conditions furnishes acids of formula 13, which are converted to compounds of formula Id following the sequence shown in Scheme 1.

Scheme 3 describes an alternative synthesis of intermediates 9 wherein R⁴ is methyl. Bromides of formula 7 undergo palladium-catalyzed Heck reaction with n-butyl vinyl ether to provide compounds of formula 9a, after hydrolysis under acidic conditions, following the procedures of Hallberg et. al. (J. Oeg. Chem., 2001, 66, 4340-4343).

Scheme 4 describes the synthesis of compounds of formula I wherein X is —C(R⁴)=N—OR⁵ and Y is —C(O)NR⁶R⁷. Treatment of 11 (Scheme 2) with R⁵O—NH₂ hydrochloride salt in ethanol or propanol under thermal conditions provides compounds of formula Ic, after removal of the protecting group.

Scheme 6 describes a general synthesis of compounds of formula I, wherein Y is —SO₂R⁶, —NR⁶S(O)ₘR⁷, in which m is 1 or 2. Compounds of formula 15, wherein Y is —SO₂R⁶, are made from compounds of formula 14 by means of copper-catalyzed coupling with sulfinic acid salts of formula R⁶SO₂Na using the procedures of Wang and Baskin (Org. Lett., 2002, 4, 4423-4425). For compounds of formula 15, wherein Y is —NR⁶S(O)ₘR⁷, copper-catalyzed N-arylation of 15 is utilized following the procedures of Buchwald et. al., J. Amer. Chem. Soc., (2001) 123: 7727-7729 or Wu and He, Tetrahedron Lett., 2003: 44, 3385-3386, and Steinhuebelm *Tetrahedron Lett.*, (2004) 45: 3305-3307. Compounds of formula 15 are converted to Ig in the same fashion as 6 to Ib shown in Scheme 2; to Ih as 9 to Id in Scheme 5; to Ii as 9 to Ic in Scheme 2 and 4.

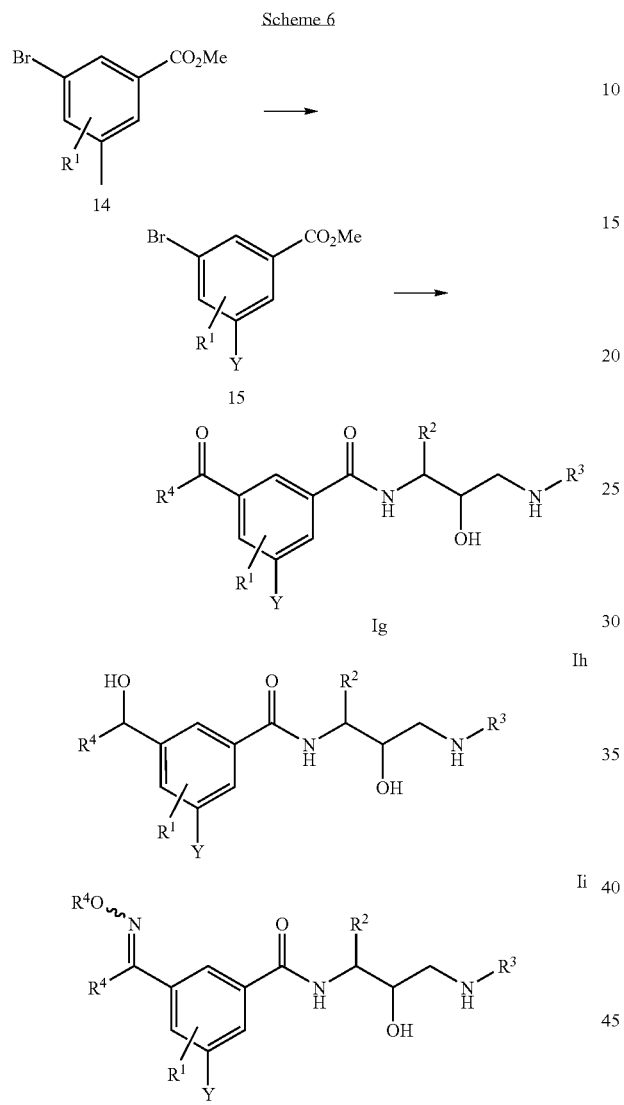

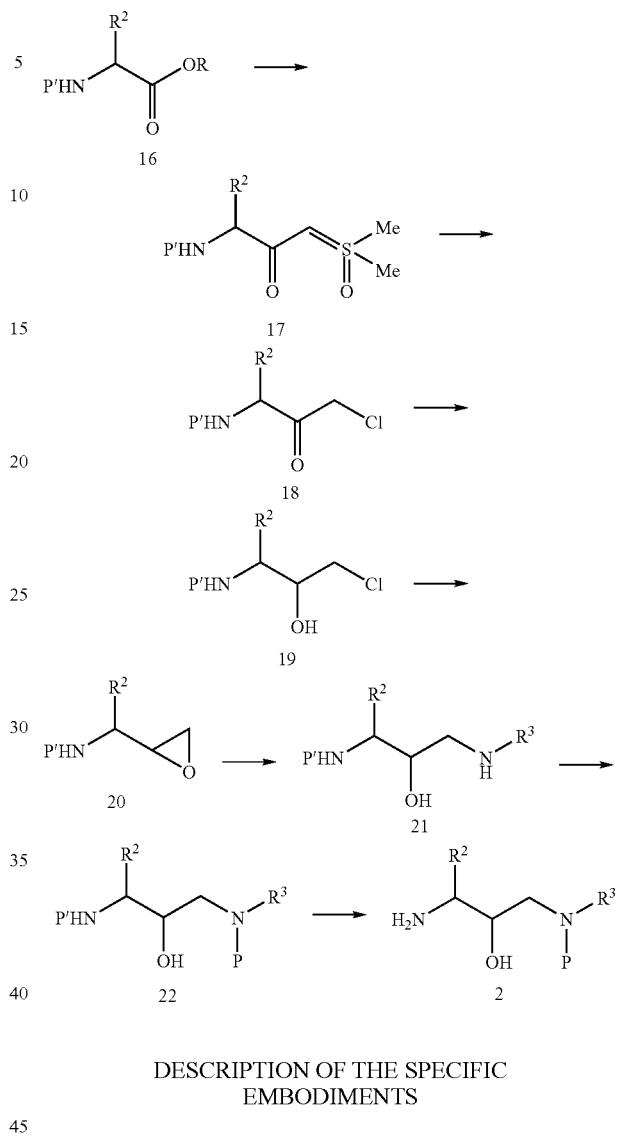

Scheme 7 describes a general synthesis of amine of formula 2 utilized in Scheme 1. Epoxides of formula 20, wherein P' is an amino protecting group similar to P as defined previously, may be prepared from 16 following the procedures of Nugent et. al, *J. Org. Chem.* (2004) 69: 1629-1633). Treatment of 16 with dimethylsulfoxonium methylide provides 17, which is converted to 18 upon exposure to lithium chloride and methanesulfonic acid. Reduction of 18 is achieved with sodium borohydride to give 19. Ring-clousure of 19 is carried out with a base such as potassium tert-butoxide to furnish 20. Epoxides of formula 20 are converted to 21 by treatment with amines of formula $R^3NH_2$. The free amine of 21 is protected under standard conditions known to one skilled in the art to provide 22, which, upon selective deprotection of P' group in which P and P' are different amino protecting groups, generates amines of formula 2.

DESCRIPTION OF THE SPECIFIC EMBODIMENTS

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on a Bruker DRX-500f at 500 MHz; a Bruker DPX-300B at 300 MHz; or a Varian Gemini 300 at 300 MHz. The chemical shifts were reported in ppm on the δ scale relative to δTMS=0. The following internal references were used for the residual protons in the following solvents: $CDCl_3$ ($δ_H$ 7.26), $CD_3OD$ ($δ_H$ 3.30) and DMSO-$d_6$ ($δ_H$ 2.50). Standard acronyms were employed to describe the multiplicity patterns: s (singlet), d (doublet), t (triplet), q (quartet), m (multiplet), b (broad), app (apparent). The coupling constant (J) is in hertz. LC/MS was performed on a Shimadzu LC-10AS liquid chromatograph using a SPD-10AV UV-VIS detector with Mass Spectrometry data determined using a Micromass LC Platform in positive electrospray ionization mode (ESI+). Mass Spectrometry (MS) data was obtained using a standard flow injection technique on a Micromass LC Platform in positive electrospray ionization mode (ESI+) unless otherwise noted. High resolution mass spectrometry (HRMS) data was obtained using a standard flow injection technique on a Finnigan MAT 900 mass spectrometer in electrospray ionization (ESI) mode. The analytical reverse phase HPLC method A is as follows unless otherwise noted: Column Phenomenex Luna C18 S10 (4.6×50 mm), Start % B=0, Final % B=100, Gradient Time=2 min, Flow rate 4 ml/min. Wavelength=220 nm, Solvent A=10% MeOH–90% $H_2O$–0.1% TFA, Solvent B=90% MeOH–10% $H_2O$–0.1% TFA; and $R_t$ in min. HPLC method B is the same as method A with the exception of 5 mL/min flow rate. Preparative reverse phase HPLC was performed on a Shimadzu LC-8A automated preparative HPLC system with detector (SPD-10AV UV-VIS) wavelength and solvent systems (A and B) the same as above except where otherwise noted.

The compounds of this application and their preparation can be understood further by the following working examples. These examples are meant to be illustrative of the present application, and are not to be taken as limiting thereof.

Chemical abbreviations used in the specification and Examples are defined as follows:

"Boc" or "BOC" for t-butyloxycarbonyl,
"BOP" for benzotriazol-1-yloxytris-(dimethylamino)-phosphonium hexafluorophosphate,
"$CD_3OD$" for deuteromethanol,
"$CDCl_3$" for deuterochloroform,
"DCC" for 1,3-dicyclohexylcarbodiimide,
"DCM" for dichloromethane
"DEAD" for diethyl azodicarboxylate,
"DIEA", "Hunig's base", or "DIPEA" for N,N-diisopropylethylamine,
"DMF" for N,N-dimethylformamide,
"DMAP" for 4-dimethylaminopyridine,
"DMPU" for 1,3-dimethyl-3,4,5,6-tetrahydro-2(1H)-pyrimidone,
"DMSO" for dimethylsulfoxide,
"DPPA" for diphenylphosphorylazide
"Et" for ethyl,
"EtOAC" for ethyl acetate,
"HOAc" for acetic acid,
"HOBt" for 1-hydroxybenzotriazole hydrate,
"HATU" for O-(7-azabenzotriazol-1-yl)-N,N,N',N'-tetramethyluronium hexafluorophosphate,
"HMPA" for hexamethylphosphoramide,
"LDA" for lithium diisopropylamide,
"LiHMDS" for lithium bis(trimethylsilyl)amide,
"NaHMDS" for sodium bis(trimethylsilyl)amide,
"NMM" for 4-methylmorpholine,
"PyBOP" for benzotriazole-1-yl-oxy-tris-pyrrolidino-phosphonium hexafluorophosphate,
"$TMSCH_2N_2$" for (trimethylsilyl)diazomethane,
"$TMSN_3$" for Azidotrimethylsilane,
"TBTU" for O-(1H-benzotriazol-1-yl)-N,N,N',N'-tetramethyluronium tetrafluoroborate,
"TEA" for triethylamine,
"TFA" for trifluoroacetic acid, and
"THF" for tetrahydrofuran.

Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

EXAMPLE 1

$N^1$-((2S,3R)-4-(3-methoxybenzylamino)-1-(3,5-difluorophenyl)-3-hydroxybutan-2-yl)-5-acetyl-$N^3$,$N^3$-dipropylisophthalamide TFA salt

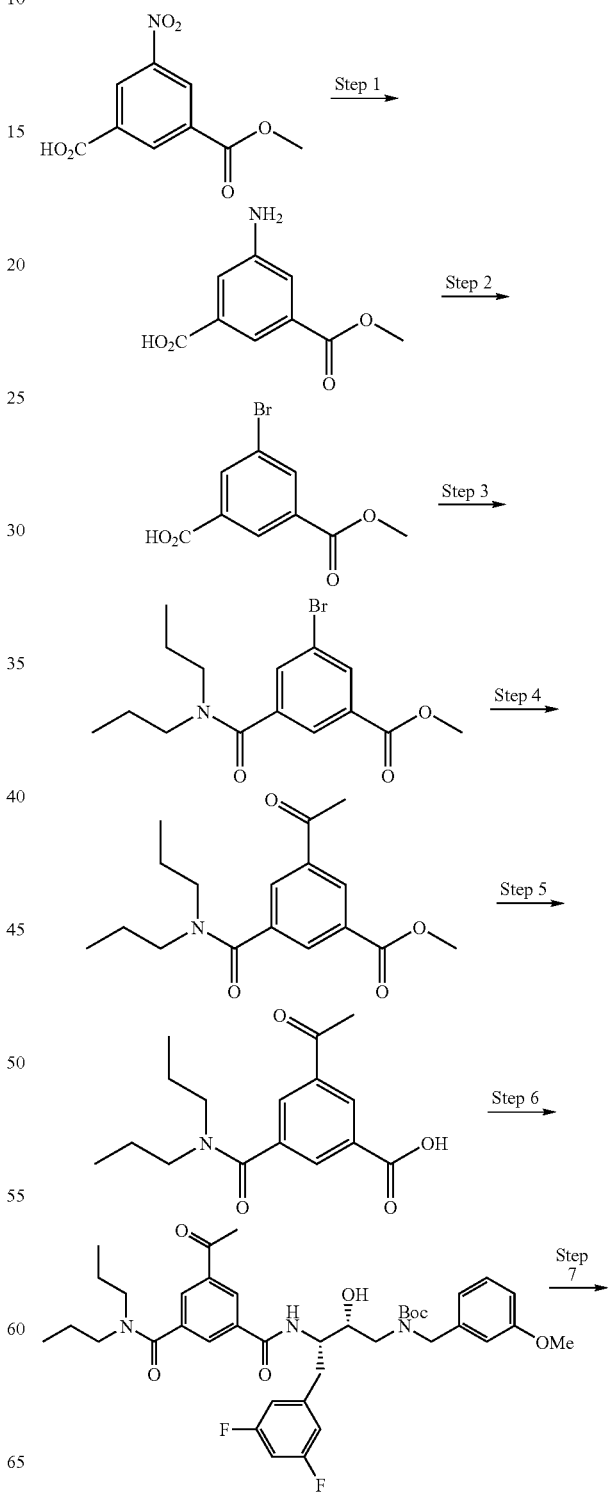

-continued

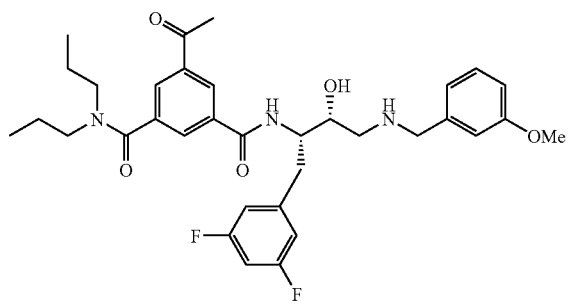

Step 1: Preparation of 3-amino-5-(methoxycarbonyl)benzoic acid. A suspension of 3-(methoxycarbonyl)-5-nitrobenzoic acid (11.25 g, 50 mmol) and palladium on carbon (10 wt %, 1.0 g) in MeOH (10 mL) was shaken in hydrogenator under hydrogen at 50 psi for 3 h. The mixture was filtered and concentrated in vacuo to give the title compound (8.0 g, 82% yield): $^1$H NMR (CD$_3$OD, 500 MHz) δ ppm 3.91 (3H, s), 7.53 (1H, m), 7.55 (1H, m), 7.92 (1H, m). HPLC retention time: 0.922 min (method A). MS (ESI) (M+H)$^+$ 196.12.

Step 2: Preparation of 3-bromo-5-(methoxycarbonyl)benzoic acid. A mixture of copper (II) bromide (5.55 g, 24.9 mmol), n-butyl nitrite (3.21 g, 31.2 mmol) and acetonitrile (90 mL) was stirred in a round bottom flask at 0° C. 3-Amino-5-(methoxycarbonyl)benzoic acid (4.05 g, 20.77 mmol) was added as a slurry in warm acetonitrile (210 mL) over 25 min. and the mixture was stirred at room temperature for 1 h. The mixture was concentrated and partitioned between dichloromethane and 3N hydrochloric acid. The organic layer was separated, dried over MgSO$_4$, and concentrated in vacuo to give the title compound (5.3 g): $^1$H NMR (CD$_3$OD, 500 MHz) δ ppm 3.97 (3H, s), 8.34-8.36 (2H, m), 8.58 (1H, m).

Step 3: Preparation of methyl 3-bromo-5-(dipropylcarbamoyl)-benzoate. A mixture of 3-bromo-5-(methoxycarbonyl)benzoic acid (2.0 g, 7.72 mmol) and HATU (3.52 g, 9.27 mmol) in DMF (70 mL) was stirred at room temperature for 10 min. Then dipropylamine (0.78 g, 1.1 mL, 7.72 mmol) was added and the resulting mixture was stirred at room temperature overnight. The mixture was diluted with ethyl acetate, washed with H$_2$O (3 times) and brine, dried over sodium sulfate, and concentrated under vacuum to give the title compound (2.6 g, 99.5% yield): $^1$H NMR (CD$_3$OD, 500 MHz) δ ppm 0.78 (3H, t, J=5 Hz), 1.01 (3H, t, J=5 Hz), 1.60 (2H, m), 1.74 (2H, m), 3.21 (2H, m), 3.49 (2H, m), 3.96 (3H, s), 7.79 (1H, m), 7.94 (1H, m), 8.23 (1H, m). HPLC retention time: 2.018 min (method B). MS (ESI) (M+H)$^+$ 342.09.

Step 4: Preparation of methyl 3-acetyl-5-(dipropylcarbamoyl)-benzoate. A mixture of methyl 3-bromo-5-(dipropylcarbamoyl)benzoate (342 mg, 1.0 mmol), 1-(vinyloxy)butane (200.4 mg, 0.26 mL, 2.0 mmol), palladium acetate (6.68 mg, 0.030 mmol), DPPP (27.2 mg, 0.066 mmol) and potassium carbonate (166 mg, 1.2 mmol) in DMF (2.5 mL) and H$_2$O (0.3 mL) in a Smith process vial was heated at 122° C. in microwave for 3 h. The reaction mixture was cooled down to RT and hydrolyzed by addition of 5% HCl slowly. The reaction mixture was worked up by extraction with ethyl acetate and concentration under vacuum. The crude mixture was purified by reverse phase prep HPLC to give the title compound: HPLC retention time: 1.805 min (method A). MS (ESI) (M+H)$^+$ 306.26.

Step 5: Preparation of 3-acetyl-5-(dipropylcarbamoyl) benzoic acid. To a solution of methyl 3-acetyl-5-(dipropylcarbamoyl)benzoate (38 mg, 0.125 mmol) in a mixture of THF (0.1 mL), MeOH (0.2 mL) and H$_2$O (0.5 mL), was added LiOH (8.9 mg, 0.374 mmol) and the mixture was stirred at room temperature for 1 h. The mixture was concentrated and partitioned between ethyl acetate and H$_2$O. The aqueous layer was washed with ethyl acetate twice and acidified with 1N HCl solution to pH around 2~3. The aqueous layer was extracted with ethyl acetate 3 times and the combined organic layers were dried over sodium sulfate and concentrated under vacuum to give the title compound (35 mg, 97.2% yield): $^1$H NMR (CD$_3$OD, 500 MHz) δ ppm 0.78 (3H, m), 1.03 (3H, t, J=5 Hz), 1.62 (2H, m), 1.77 (2H, m), 2.69 (3H, s), 3.23 (2H, m), 3.52 (2H, m), 8.17 (1H, m), 8.21 (1H, m), 8.68 (1H, m). HPLC retention time: 1.687 min (method A). MS (ESI) (M+H)$^+$ 292.23.

Step 6: Preparation of tert-butyl 3-methoxybenzyl((2R, 3S)-3-(3-acetyl-5-(benzamido)benzamido)-4-(3,5-difluorophenyl)-2-hydroxybutyl)-carbamate. A mixture of 3-acetyl-5-(dipropylcarbamoyl)benzoic acid (95 mg, 0.326 mmol), HATU (149 mg, 0.392 mmol) and Hunig's base (168.8 mg, 0.2 mL, 1.306 mmol) in DMF (2.9 mL) was stirred for 10 min and then tert-butyl 3-methoxybenzyl((2R,3S)-3-amino-4-(3,5-difluorophenyl)-2-hydroxybutyl)-carbamate (142 mg, 0.326 mmol) was added. The reaction mixture was stirred at room temperature overnight. The reaction mixture was diluted with ethyl acetate and washed with H$_2$O 3 times. The organic layer was dried over sodium sulfate and concentrated under vacuum to give the title compound (220 mg) which was ready for next step without further purification: $^1$H NMR (CD$_3$OD, 500 MHz) δ ppm 0.71 (3H, m), 1.02 (3H, m), 1.48-1.55 (11H, m), 1.74-1.76 (2H, m), 2.66 (2H, m), 2.87 (1H, m), 3.11-3.17 (3H, m), 3.33 (1H, m), 3.50 (2H, m), 3.76 (4H, m), 3.98 (1H, m), 4.32 (1H, m), 4.42-4.45 (1H, m), 4.68-4.82 (2H, m), 6.70-6.74 (1H, m), 6.80 (3H, m), 6.90 (2H, m), 7.22 (1H, m), 7.51-7.87 (1H, m), 8.07 (1H, m), 8.36-8.56 (1H, m). HPLC retention time: 2.195 min (method B). MS (ESI) (M+H)$^+$ 710.31.

Step 7: N$^1$-((2S,3R)-4-(3-methoxybenzylamino)-1-(3,5-difluoro-phenyl)-3-hydroxybutan-2-yl)-5-acetyl-N$^3$,N$^3$-dipropylisophthalamide TFA salt. tert-Butyl 3-methoxybenzyl((2R,3S)-3-(3-acetyl-5-(benzamido)benzamido)-4-(3,5-difluorophenyl)-2-hydroxybutyl)carbamate (7.0 mg) was treated with HCl (1 M solution in ether, 0.4 mL) and the mixture was stirred at room temperature overnight. The reaction mixture was concentrated under vacuum and purified by reverse phase prep HPLC to give the title compound (5 mg): $^1$H NMR (CD$_3$OD, 500 MHz) δ ppm 0.73 (3H, m), 1.03 (3H, m), 1.55 (2H, m), 1.76 (2H, m), 2.66 (3H, s), 2.88 (1H, m), 3.08 (1H, dd, J=10, 15 Hz), 3.17-3.24 (3H, m), 3.39 (1H, dd, J=5, 15 Hz), 3.52 (2H, m), 3.81 (3H, s), 4.00 (1H, m), 4.21-4.30 (3H, m), 6.77 (1H, m), 6.90-6.92 (2H, m), 6.98 (1H, m), 7.06 (1H, d, J=5 Hz), 7.09 (1H, m), 7.35 (1H, m), 7.80 (1H, m), 8.10 (1H, m), 8.29 (1H, m). HPLC retention time: 2.088 min (method B). MS (ESI) (M+H)$^+$ 610.26.

EXAMPLE 2

N¹-((2S,3R)-4-(3-methoxybenzylamino)-1-(3,5-difluorophenyl)-3-hydroxybutan-2-yl)-5-(1-hydroxyethyl)-N³,N³-dipropylisophthalamide TFA salt

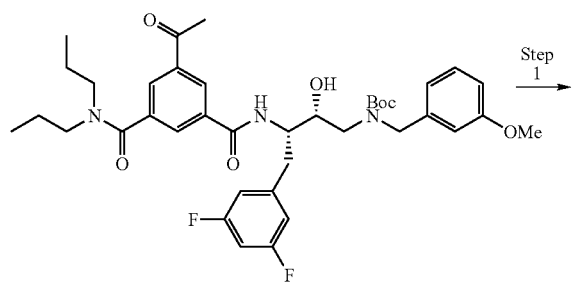

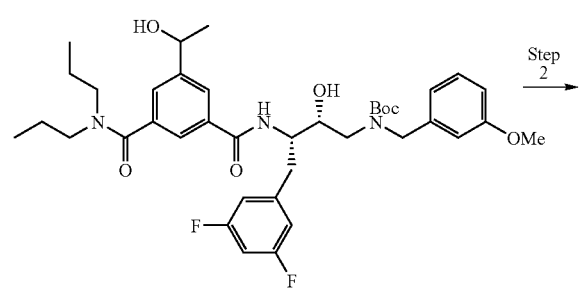

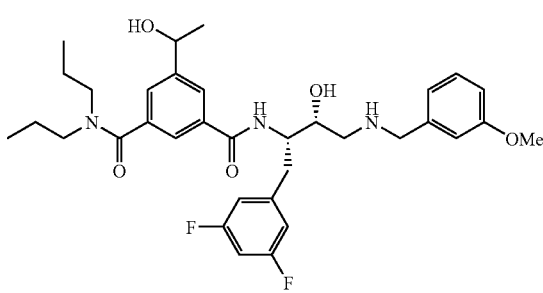

Step 1: Preparation of tert-butyl 3-methoxybenzyl((2R,3S)-3-(3-(benzamido)-5-(1-hydroxyethyl)benzamido)-4-(3,5-difluorophenyl)-2-hydroxybutyl)carbamate. tert-Butyl 3-methoxybenzyl((2R,3S)-3-(3-acetyl-5-(benzamido)benzamido)-4-(3,5-difluorophenyl)-2-hydroxybutyl)carbamate (20 mg, 0.0282 mmol) was dissolved in MeOH (0.2 mL) and sodium borohydride (1.43 mg, 0.0378 mmol) was added. The reaction mixture was stirred at room temperature for 2 h. The mixture was concentrated and partitioned between ethyl acetate and H₂O. The organic layer was separated and purified by reverse phase prep HPLC to give the title compound (15 mg): ¹H NMR (CD₃OD, 500 MHz) δ ppm 0.71 (3H, t, J=5 Hz), 1.02 (3H, m), 1.45-1.47 (2H, m), 1.54 (2H, m), 1.74 (2H, m), 2.85 (1H, m), 3.09-3.18 (3H, m), 3.28 (1H, m), 3.49 (2H, m), 3.72-3.81 (4H, m), 3.97 (1H, m), 4.29 (1H, m), 4.41-4.44 (1H, m), 4.75 (1H, m), 4.90 (1H, m), 6.71 (1H, m), 6.81-6.82 (3H, m), 6.89 (2H, m), 7.22 (1H, m), 7.49-7.52 (2H, m), 7.76 (1H, m). HPLC retention time: 2.223 min (method A). MS (ESI) (M+H)⁺ 712.57.

Step 2: Preparation of N¹-((2S,3R)-4-(3-methoxybenzylamino)-1-(3,5-difluorophenyl)-3-hydroxybutan-2-yl)-5-(1-hydroxyethyl)-N³,N³-dipropylisophthalamide TFA salt. tert-Butyl 3-methoxybenzyl((2R,3S)-3-(3-(benzamido)-5-(1-hydroxyethyl)benzamido)-4-(3,5-difluorophenyl)-2-hydroxybutyl)carbamate (8.0 mg) was treated with HCl (1 M solution in ether, 0.4 mL) and the mixture was stirred at room temperature for 12 h. The reaction mixture was concentrated under vacuum and purified by reverse phase prep HPLC to give the title compound (6 mg): ¹H NMR (CD₃OD, 400 MHz) δ ppm 0.68 (3H, t, J=8 Hz), 0.99 (3H, m), 1.42 (3H, m), 1.50 (2H, m), 1.71 (2H, m), 2.82 (1H, dd, J=12, 16 Hz), 3.04 (1H, dd, J=8, 12 Hz), 3.12 (2H, t, J=8 Hz), 3.18 (1H, dd, J=4, 12 Hz), 3.33-3.37 (2H, m), 3.46 (2H, t, J=8 Hz), 3.79 (3H, s), 3.92 (1H, dt, J=4, 8 Hz), 4.16-4.24 (3H, m), 6.73 (1H, m), 6.87 (2H, m), 6.96 (1H, m), 7.04 (1H, d, J=4 Hz), 7.07 (1H, m), 7.32 (1H, t, J=8 Hz), 7.41 (1H, s), 7.50 (1H, m), 7.67 (1H, d, J=8 Hz). HPLC retention time: 2.023 min (method B). MS (ESI) (M+H)⁺ 612.28.

EXAMPLE 3

N¹-((2S,3R)-4-(3-methoxybenzylamino)-1-(3,5-difluorophenyl)-3-hydroxybutan-2-yl)-5-((E)-1-(methoxyimino)ethyl)-N³,N³-dipropylisophthalamide TFA salt

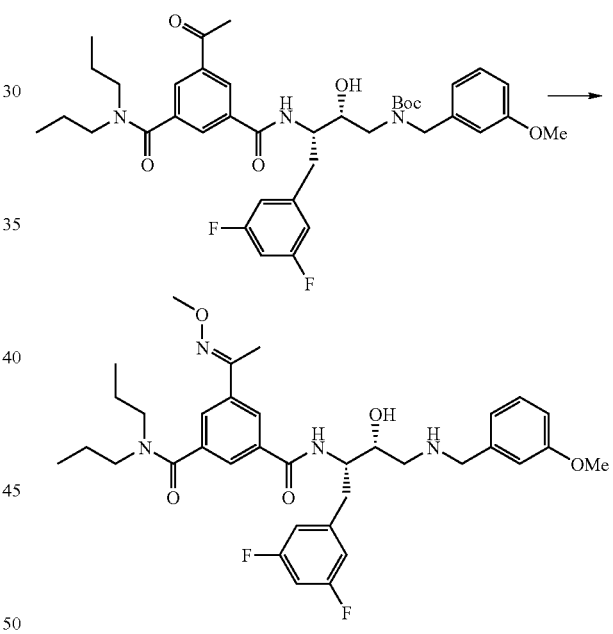

A mixture of tert-butyl 3-methoxybenzyl((2R,3S)-3-(3-acetyl-5-(benzamido)benzamido)-4-(3,5-difluorophenyl)-2-hydroxybutyl)carbamate (20 mg, 0.0282 mmol) and methoxyamine hydrochloride (4.71 mg, 0.0564 mmol) in ethanol (0.2 mL) was heated at 80° C. for 2 h. The reaction mixture was purified by reverse phase prep HPLC to give the title compound (10 mg): ¹H NMR (CD₃OD, 500 MHz) δ ppm 0.73 (3H, m), 1.03 (3H, m), 1.56 (2H, m), 1.76 (2H, m), 2.25 (3H, s), 2.86 (1H, dd, J=10, 15 Hz), 3.08 (1H, m), 3.16-3.22 (3H, m), 3.39 (1H, dd, J=5, 15 Hz), 3.50 (2H, m), 3.81 (3H, s), 3.98 (1H, m), 4.02 (3H, s), 4.21-4.28 (3H, m), 6.77 (1H, m), 6.91-6.94 (2H, m), 6.98 (1H, m), 7.06 (1H, d, J=5 Hz), 7.09 (1H, m), 7.34 (1H, m), 7.56 (1H, m), 7.82 (1H, m), 7.96 (1H, m). HPLC retention time: 2.027 min (method A). MS (ESI) (M+H)⁺ 639.50.

EXAMPLE 4

N$^1$-((2S,3R)-4-(3-methoxybenzylamino)-1-(3,5-difluorophenyl)-3-hydroxybutan-2-yl)-5-((E)-1-(benzyloxyimino)ethyl)-N$^3$,N$^3$-dipropylisophthalamide TFA salt

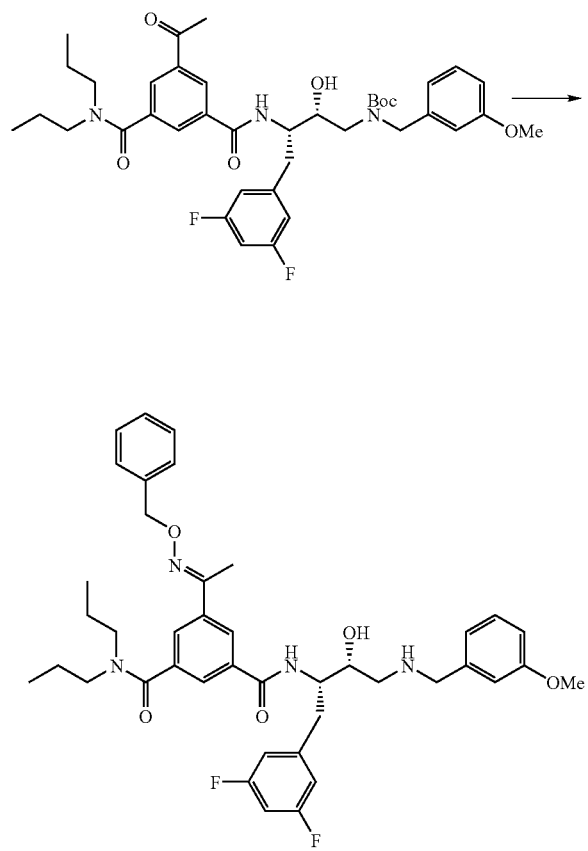

A mixture of tert-butyl 3-methoxybenzyl((2R,3S)-3-(3-acetyl-5-(benzamido)benzamido)-4-(3,5-difluorophenyl)-2-hydroxybutyl)carbamate (20 mg, 0.0282 mmol) and benzoxyamine hydrochloride (9.0 mg, 0.0564 mmol) in ethanol (0.2 mL) was heated at 80° C. for 2 h. The reaction mixture was purified by reverse phase prep HPLC to give the title compound (11 mg): $^1$H NMR (CD$_3$OD, 500 MHz) δ ppm 0.71 (3H, m), 1.02 (3H, m), 1.54 (2H, m), 1.75 (2H, m), 2.30 (3H, s), 2.86 (1H, dd, J=10, 15 Hz), 3.06 (1H, dd, J=10, 15 Hz), 3.15 (2H, m), 3.20 (1H, m), 3.38 (1H, m), 3.50 (2H, m), 3.78 (3H, s), 3.96 (1H, m), 4.02 (3H, s), 4.20-4.28 (3H, m), 5.27 (2H, s), 6.77 (1H, m), 6.90-6.92 (2H, m), 6.95 (1H, m), 7.06 (1H, d, J=5 Hz), 7.08 (1H, m), 7.29-7.33 (2H, m), 7.34-7.37 (2H, m), 7.41 (2H, d, J=10 Hz), 7.55 (1H, m), 7.81 (1H, m), 7.94 (1H, m). HPLC retention time: 2.168 min (method A). MS (ESI) (M+H)$^+$ 715.54.

EXAMPLE 5

N$^1$-((2S,3R)-4-(3-methoxybenzylamino)-1-(3,5-difluorophenyl)-3-hydroxybutan-2-yl)-5-((E)-1-(hydroxyimino)ethyl)-N$^3$,N$^3$-dipropylisophthalamide hydrochloride

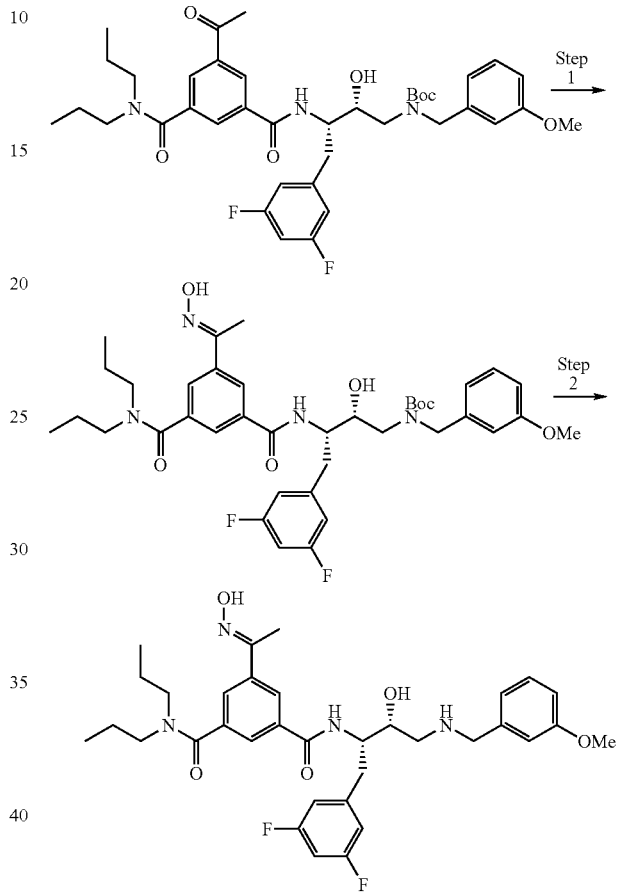

Step 1: Preparation of tert-butyl 3-methoxybenzyl((2R,3S)-3-(3-(benzamido)-5-((E)-1-(hydroxyimino)ethyl)benzamido)-4-(3,5-difluorophenyl)-2-hydroxybutyl)carbamate. A mixture of tert-butyl 3-methoxybenzyl((2R,3S)-3-(3-acetyl-5-(benzamido)benzamido)-4-(3,5-difluorophenyl)-2-hydroxybutyl)carbamate (20 mg, 0.0282 mmol) and hydroxyamine hydrochloride (0.0564 mmol) in ethanol (0.14 mL) was heated at 80° C. for 2 h. The reaction mixture was purified by reverse phase prep HPLC to give the title compound (10 mg): HPLC retention time: 2.255 min (method A). MS (ESI) (M+H)$^+$ 725.53.

Step 2: Preparation of N$^1$-((2S,3R)-4-(3-methoxybenzylamino)-1-(3,5-difluorophenyl)-3-hydroxybutan-2-yl)-5-((E)-1-(hydroxyimino)ethyl)-N$^3$,N$^3$-dipropylisophthalamide hydrochloride. tert-Butyl 3-methoxybenzyl((2R,3S)-3-(3-(benzamido)-5-((E)-1-(hydroxyimino)ethyl)benzamido)-4-(3,5-difluorophenyl)-2-hydroxybutyl)carbamate (10 mg) was treated with HCl (1 M solution in ether, 0.3 mL) and the mixture was stirred at RT for overnight. The reaction mixture was concentrated under vacuum to give the title compound (7 mg): $^1$H NMR (CD$_3$OD, 500 MHz) δ ppm 0.72 (3H, m), 1.02 (3H, m), 1.54 (2H, m), 1.74 (2H, m), 2.26 (3H, s), 2.88 (1H, m), 3.08 (1H, m), 3.16-3.22 (3H, m), 3.36-3.40 (1H, m), 3.50

(2H, m), 3.81 (3H, s), 3.98 (1H, m), 4.20-4.28 (3H, m), 6.77 (1H, m), 6.92 (2H, d, J=5 Hz), 6.98 (1H, m), 7.07 (1H, d, J=10 Hz), 7.10 (1H, s), 7.34 (1H, m), 7.54 (1H, s), 7.83 (1H, s), 7.95 (1H, s). HPLC retention time: 1.812 min (method B). MS (ESI) (M+H)+ 625.17.

EXAMPLE 6

N$^1$-((2S,3R)-4-(3-methoxybenzylamino)-1-(3,5-difluorophenyl)-3-hydroxybutan-2-yl)-5-((E)-1-(isobutoxyimino)ethyl)-N$^3$,N$^3$-dipropylisophthalamide TFA salt

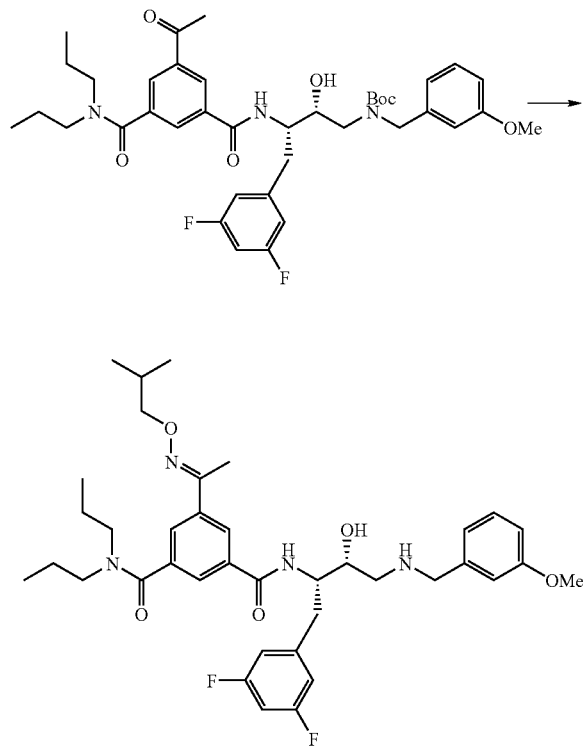

A mixture of tert-butyl 3-methoxybenzyl((2R,3S)-3-(3-acetyl-5-(benzamido)benzamido)-4-(3,5-difluorophenyl)-2-hydroxybutyl)carbamate (10 mg, 0.014 mmol) and o-isobutylhydroxylamine hydrochloride (3.54 mg, 0.028 mmol) in ethanol (0.14 mL) was heated at 80° C. for 2 h. The reaction mixture was purified by reverse phase prep HPLC to give the title compound (4.2 mg): $^1$H NMR (CD$_3$OD, 500 MHz) δ ppm 0.74 (3H, m), 1.00 (6H, d, J=5 Hz), 1.03 (3H, m), 1.56 (2H, m), 1.76 (2H, m), 2.07 (1H, m), 2.27 (3H, s), 2.86 (1H, dd, J=10, 15 Hz), 3.08 (1H, m), 3.17 (2H, t, J=5 Hz), 3.21 (1H, m), 3.39 (1H, dd, J=5, 15 Hz), 3.50 (2H, m), 3.81 (3H, s), 3.95-4.02 (3H, m), 4.21-4.29 (3H, m), 6.77 (1H, m), 6.91-6.93 (2H, m), 6.98 (1H, m), 7.06 (1H, d, J=5 Hz), 7.09 (1H, m), 7.34 (1H, m), 7.56 (1H, m), 7.83 (1H, m), 7.95 (1H, m). HPLC retention time: 2.183 min (method A). MS (ESI) (M+H)+ 681.32.

EXAMPLE 7

N$^1$-((2S,3R)-4-(3-methoxybenzylamino)-1-(3,5-difluorophenyl)-3-hydroxybutan-2-yl)-5-((E)-1-(allyloxyimino)ethyl)-N$^3$,N$^3$-dipropylisophthalamide TFA salt

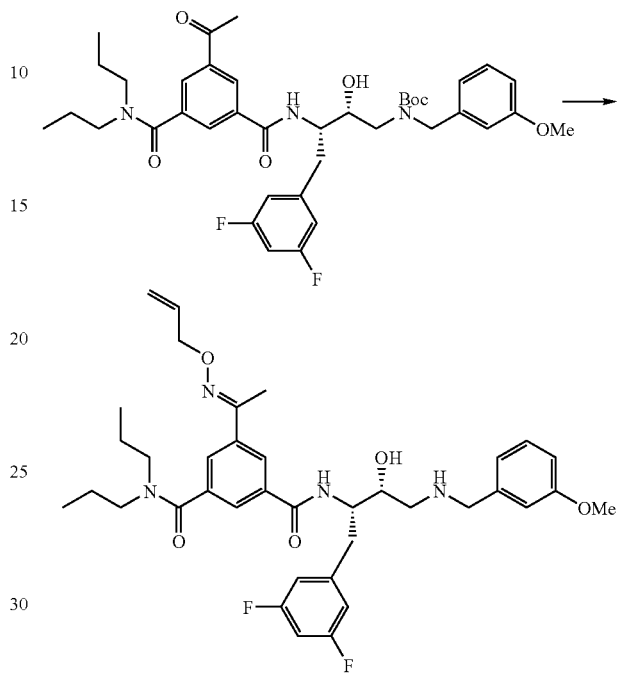

A mixture of tert-butyl 3-methoxybenzyl((2R,3S)-3-(3-acetyl-5-(benzamido)benzamido)-4-(3,5-difluorophenyl)-2-hydroxybutyl)carbamate (10 mg, 0.014 mmol) and o-allylhydroxylamine hydrochloride (3.1 mg, 0.028 mmol) in ethanol (0.14 mL) was heated at 80° C. for 2 h. The reaction mixture was purified by reverse phase prep HPLC to give the title compound (4.3 mg): $^1$H NMR (CD$_3$OD, 500 MHz) δ ppm 0.74 (3H, m), 1.03 (3H, m), 1.56 (2H, m), 1.76 (2H, m), 2.29 (3H, s), 2.86 (1H, dd, J=10, 15 Hz), 3.08 (1H, m), 3.17 (2H, m), 3.21 (1H, m), 3.39 (1H, dd, J=5, 15 Hz), 3.50 (2H, m), 3.81 (3H, s), 3.98 (1H, m), 4.21-4.28 (3H, m), 4.74 (2H, m), 5.24 (1H, dd, J=5, 10 Hz), 5.34 (1H, m), 6.08 (1H, m), 6.77 (1H, m), 6.90-6.93 (2H, m), 6.98 (1H, m), 7.06 (1H, d, J=5 Hz), 7.09 (1H, m), 7.34 (1H, m), 7.56 (1H, m), 7.83 (1H, m), 7.96 (1H, m). HPLC retention time: 2.088 min (method A). MS (ESI) (M+H)+ 665.32.

EXAMPLE 8

N$^1$-((2S,3R)-4-(3-methoxybenzylamino)-1-(3,5-difluorophenyl)-3-hydroxybutan-2-yl)-5-acetyl-N$^3$-methyl-N$^3$-propylisophthalamide TFA salt

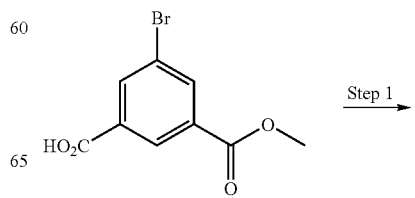

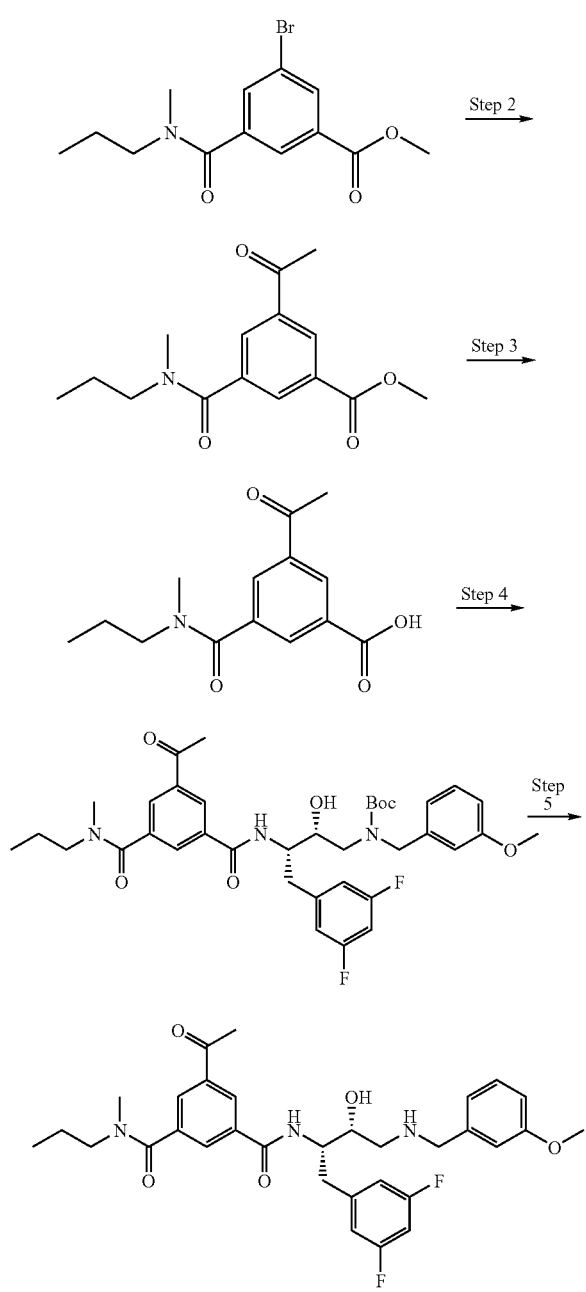

Step 1: Preparation of methyl 3-bromo-5-(methyl(propyl) carbamoyl)benzoate. A mixture of 3-bromo-5-(methoxycarbonyl)benzoic acid (1.0 g, 3.86 mmol) and HATU (1.76 g, 4.63 mmol) in DMF (35 mL) was stirred at room temperature for 10 min. Then N-methylpropan-1-amine (0.28 g, 0.4 mL, 3.86 mmol) was added and the resulting mixture was stirred at room temperature overnight. The mixture was diluted with ethyl acetate, washed with H$_2$O (3 times) and brine, dried over sodium sulfate, and concentrated under vacuum to give the title compound (1.2 g, 99% yield): HPLC retention time: 1.89 min (method A). MS (ESI) (M+H)$^+$ 314.03.

Step 2: Preparation of methyl 3-acetyl-5-(methyl(propyl)-carbamoyl)benzoate. A mixture of methyl 3-bromo-5-(methyl(propyl)carbamoyl)benzoate (314 mg, 1.0 mmol), 1-(vinyloxy)butane (200.4 mg, 0.26 mL, 2.0 mmol), palladium acetate (6.68 mg, 0.030 mmol), DPPP (27.2 mg, 0.066 mmol) and potassium carbonate (166 mg, 1.2 mmol) in DMF (2.5 mL) and H$_2$O (0.3 mL) in a Smith process vial was heated at 122° C. in microwave for 3 h. The reaction mixture was cooled down to RT and hydrolyzed by addition of 5% HCl slowly. The reaction mixture was worked up by extraction with ethyl acetate and concentration under vacuum. The crude mixture was purified by reverse phase prep HPLC to give the title compound (175 mg, 63% yield): HPLC retention time: 1.58 min (method A). MS (ESI) (M+H)$^+$ 278.19.

Step 3: Preparation of 3-acetyl-5-(methyl(propyl)carbamoyl)benzoic acid. To a solution of methyl 3-acetyl-5-(methyl (propyl)carbamoyl)benzoate (107 mg, 0.386 mmol) in a mixture of THF (0.4 mL), MeOH (0.8 mL) and H$_2$O (2.0 mL), was added LiOH (28 mg, 1.159 mmol) and the mixture was stirred at room temperature for 1 h. The mixture was concentrated and partitioned between ethyl acetate and H$_2$O. The aqueous layer was washed with ethyl acetate twice and acidified with 1N HCl solution to pH around 2~3. The aqueous layer was extracted with ethyl acetate 3 times and the combined organic layers were dried over sodium sulfate and concentrated under vacuum to give the title compound which was ready for next step without further purification: HPLC retention time: 1.412 min (method A). MS (ESI) (M+H)$^+$ 264.18.

Step 4: Preparation of tert-butyl 3-methoxybenzyl((2R,3S)-3-(3-acetyl-5-(benzamido)benzamido)-4-(3,5-difluorophenyl)-2-hydroxybutyl)carbamate. A mixture of 3-acetyl-5-(methyl(propyl)carbamoyl)-benzoic acid (from step 3, 0.386 mmol), HATU (176 mg, 0.464 mmol) and Hunig's base (200 mg, 0.3 mL, 1.545 mmol) in DMF (4.0 mL) was stirred for 10 min and then tert-butyl 3-methoxybenzyl((2R,3S)-3-amino-4-(3,5-difluorophenyl)-2-hydroxybutyl)-carbamate (168 mg, 0.386 mmol) was added. The reaction mixture was stirred at room temperature overnight. The reaction mixture was diluted with ethyl acetate and washed with H$_2$O 3 times. The organic layer was dried over sodium sulfate and concentrated under vacuum. The crude product was purified by reverse phase prep HPLC to give the title compound (100 mg): HPLC retention time: 2.185 min (method A). MS (ESI) (M+H)$^+$ 682.32.

Step 5: N$^1$-((2S,3R)-4-(3-methoxybenzylamino)-1-(3,5-difluorophenyl)-3-hydroxybutan-2-yl)-5-acetyl-N$^3$,N$^3$-dipropylisophthalamide TFA salt. tert-Butyl 3-methoxybenzyl((2R,3S)-3-(3-acetyl-5-(benzamido)benzamido)-4-(3,5-difluorophenyl)-2-hydroxybutyl)carbamate (7 mg) was treated with HCl (1 M solution in ether, 0.1 mL) and the mixture was stirred at room temperature overnight. The reaction mixture was concentrated under vacuum and purified by reverse phase prep HPLC to give the title compound (5 mg): $^1$H NMR (CD$_3$OD, 500 MHz) δ ppm 0.76-1.05 (3H, m), 1.6-1.78 (2H, m), 2.68 (3H, s), 2.88 (1H, m), 2.97-3.4 (7H, m), 3.58 (1H, m), 3.81 (3H, s), 4.00 (1H, m), 4.21-4.30 (3H, m), 6.79-7.35 (7H, m), 7.82 (1H, s), 8.15 (1H, s), 8.3 (1H, s). HPLC retention time: 1.738 min (method A). MS (ESI) (M+H)$^+$ 582.30.

EXAMPLE 9

N$^1$-((2S,3R)-4-(3-methoxybenzylamino)-1-(3,5-difluorophenyl)-3-hydroxybutan-2-yl)-5-((E)-1-(hydroxyimino)ethyl)-N$^3$-methyl-N$^3$-propylisophthalamide hydrochloride

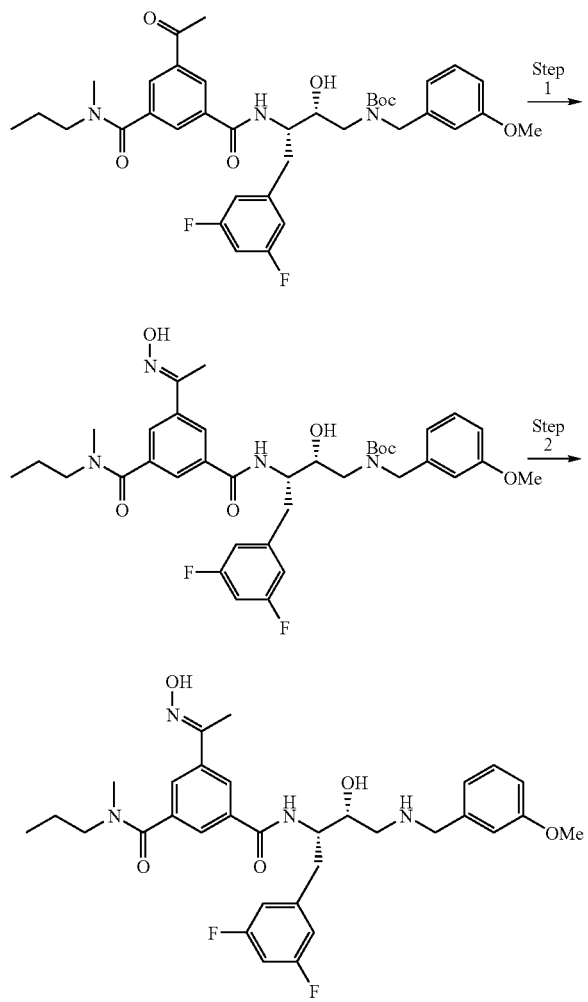

Step 1: Preparation of tert-butyl 3-methoxybenzyl((2R,3S)-3-(3-(benzamido)-5-((E)-1-(hydroxyimino)ethyl)benzamido)-4-(3,5-difluorophenyl)-2-hydroxybutyl)carbamate. A mixture of tert-butyl 3-methoxybenzyl((2R,3S)-3-(3-acetyl-5-(benzamido)benzamido)-4-(3,5-difluorophenyl)-2-hydroxybutyl)carbamate (10 mg, 0.0147 mmol) and hydroxyamine hydrochloride (2.0 mg, 0.0294 mmol) in ethanol (0.1 mL) was heated at 80° C. for 2 h. The reaction mixture was purified by reverse phase prep HPLC to give the title compound: HPLC retention time: 2.16 min (method A). MS (ESI) (M+H)$^+$ 697.90

Step 2: Preparation of N$^1$-((2S,3R)-4-(3-methoxybenzylamino)-1-(3,5-difluorophenyl)-3-hydroxybutan-2-yl)-5-((E)-1-(hydroxyimino)ethyl)-N$^3$-methyl-N$^3$-propylisophthalamide hydrochloride. tert-Butyl 3-methoxybenzyl-((2R,3S)-3-(3-(benzamido)-5-((E)-1-(hydroxyimino)ethyl)benzamido)-4-(3,5-difluorophenyl)-2-hydroxybutyl) carbamate (from step 1, 0.0147 mmol) was treated with HCl (1 M solution in ether, 0.1 mL) and the mixture was stirred at RT for overnight. The reaction mixture was concentrated under vacuum to give the title compound (8 mg): $^1$H NMR (CD$_3$OD, 500 MHz) δ ppm 0.76-1.05 (3H, m), 1.6-1.75 (2H, m), 2.28 (3H, s), 2.85-3.55 (9H, m), 3.82 (3H, s), 3.92-3.99 (1H, m), 4.21-4.30 (3H, m), 6.76-7.39 (7H, m), 7.58 (1H, s), 7.88 (1H, s), 7.98 (1H, s). HPLC retention time: 1.727 min (method A). MS (ESI) (M+H)$^+$ 597.35.

Examples 10-13 were prepared using the procedures described in Example 9.

EXAMPLE 10

N$^1$-((2S,3R)-4-(3-methoxybenzylamino)-1-(3,5-difluorophenyl)-3-hydroxybutan-2-yl)-5-((E)-1-(methoxyimino)ethyl)-N$^3$-methyl-N$^3$-propylisophthalamide hydrochloride

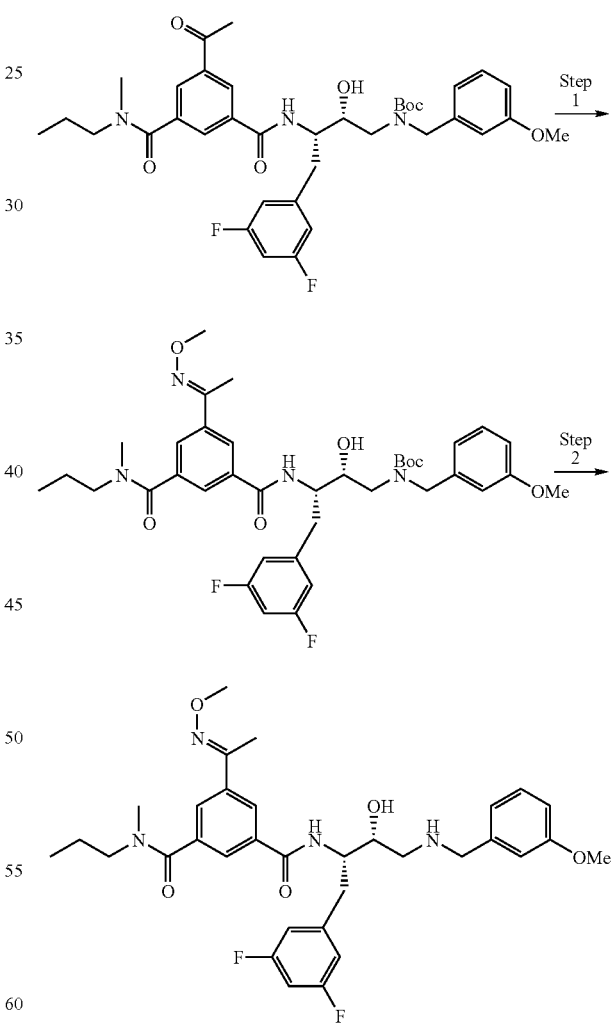

$^1$H NMR (CD$_3$OD, 500 MHz) δ ppm 0.76-1.1 (3H, m), 1.58-1.8 (2H, m), 2.28 (3H, s), 2.86-3.56 (9H, m), 3.8 (3H, s), 3.95-3.99 (1H, m), 4.0 (3H, s), 4.21-4.28 (3H, m), 6.76-7.36 (7H, m), 7.6 (1H, s), 7.88 (1H, s), 7.98 (1H, s). HPLC retention time: 1.905 min (method A). MS (ESI) (M+H)$^+$ 611.43.

EXAMPLE 11

N$^1$-((2S,3R)-4-(3-methoxybenzylamino)-1-(3,5-difluorophenyl)-3-hydroxybutan-2-yl)-5-((E)-1-(benzyloxyimino)ethyl)-N$^3$-methyl-N$^3$-propylisophthalamide hydrochloride

EXAMPLE 12

N$^1$-((2S,3R)-4-(3-methoxybenzylamino)-1-(3,5-difluorophenyl)-3-hydroxybutan-2-yl)-5-((E)-1-(isobutoxyimino)ethyl)-N$^3$-methyl-N$^3$-propylisophthalamide hydrochloride

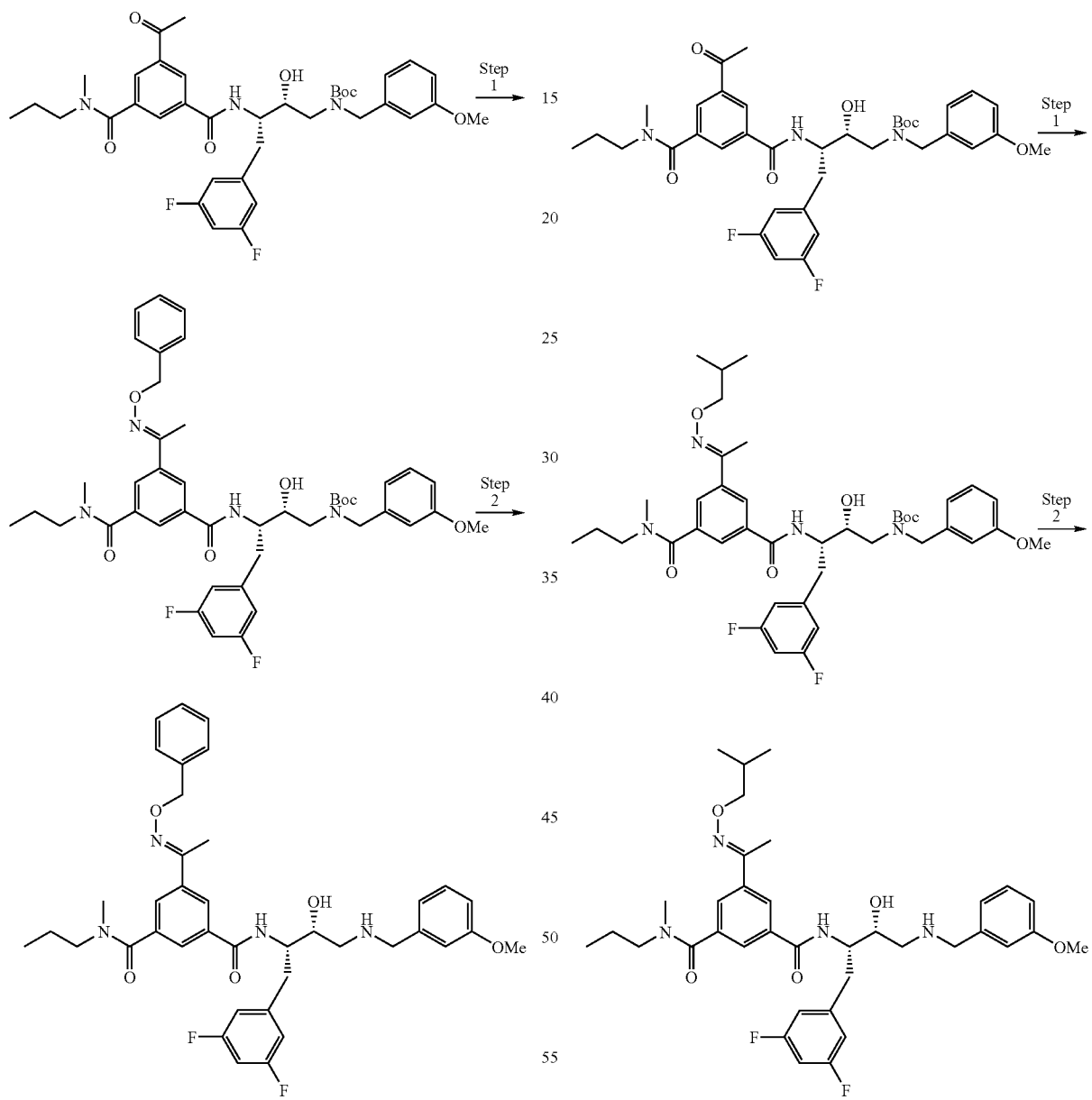

$^1$H NMR (CD$_3$OD, 500 MHz) δ ppm 0.7-1.08 (3H, m), 1.52-1.8 (2H, m), 2.3 (3H, s), 2.82-3.4 (8H, m), 3.5-3.57 (1H, m), 3.8 (3H, s), 3.94-3.97 (1H, m), 4.2-4.27 (3H, m), 5.27 (2H, s), 6.76-7.36 (12H, m), 7.6 (1H, s), 7.86 (1H, s), 7.95 (1H, s). HPLC retention time: 2.082 min (method A). MS (ESI) (M+H)$^+$ 687.31.

$^1$H NMR (CD$_3$OD, 500 MHz) δ ppm 0.75-1.1 (9H, m), 1.6-1.8 (2H, m), 2.3 (3H, s), 2.86-3.56 (9H, m), 3.81 (3H, s), 3.95-3.98 (1H, m), 4.01-4.02 (2H, d, J=7 Hz), 4.2-4.28 (3H, m), 6.76-7.38 (7H, m), 7.6 (1H, s), 7.88 (1H, s), 7.98 (1H, s). HPLC retention time: 2.107 min (method A). MS (ESI) (M+H)$^+$ 653.37.

EXAMPLE 13

N$^1$-((2S,3R)-4-(3-methoxybenzylamino)-1-(3,5-difluorophenyl)-3-hydroxybutan-2-yl)-5-((E)-1-(allyloxyimino)ethyl)-N$^3$-methyl-N$^3$-propylisophthalamide hydrochloride

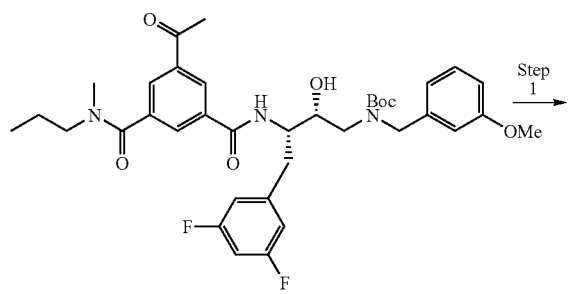

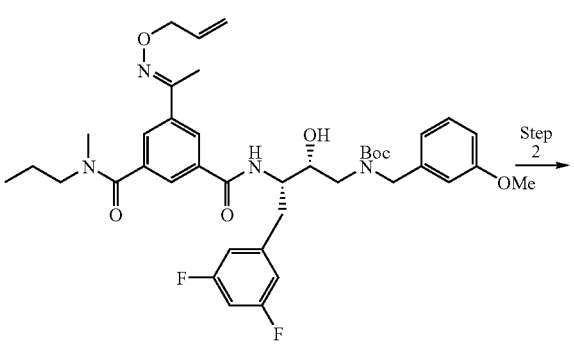

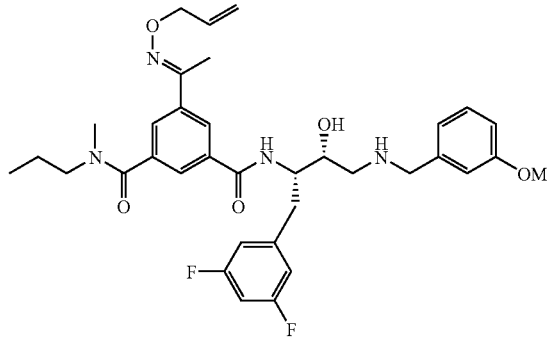

$^1$H NMR (CD$_3$OD, 500 MHz) δ ppm 0.7-1.08 (3H, m), 1.57-1.8 (2H, m), 2.3 (3H, s), 2.8-3.6 (9H, m), 3.81 (3H, s), 3.92-3.98 (1H, m), 4.2-4.3 (3H, m), 4.73-4.74 (2H, d, J=5.5 Hz), 5.24 (1H, dd, J=1.5, 10.5 Hz), 5.34 (1H, dd, J=1.5, 17 Hz), 6.05-6.15 (1H, m), 6.76-7.37 (7H, m), 7.6 (1H, s), 7.88 (1H, s), 7.98 (1H, s). HPLC retention time: 2.00 min (method A). MS (ESI) (M+H)$^+$ 637.34.

EXAMPLE 14

N$^1$-((2S,3R)-4-(3-methoxybenzylamino)-1-(3,5-difluorophenyl)-3-hydroxybutan-2-yl)-N$^3$-methyl-5-((E)-1-(propoxyimino)ethyl)-N$^3$-propylisophthalamide

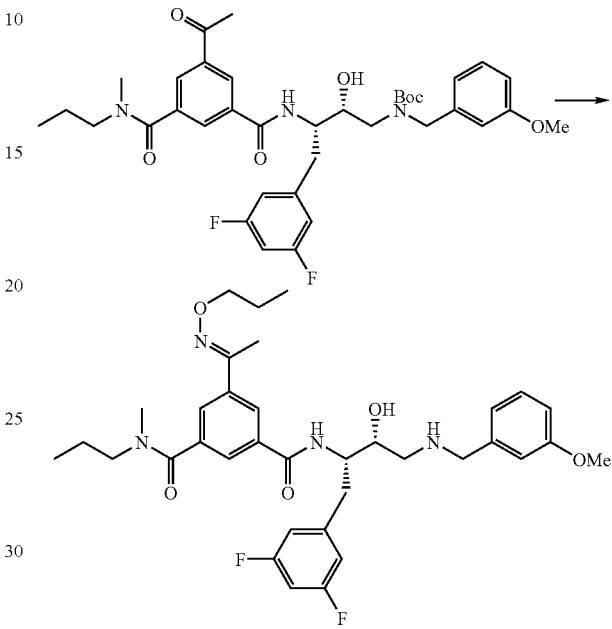

A mixture of tert-butyl 3-methoxybenzyl((2R,3S)-3-(3-acetyl-5-(benzamido)benzamido)-4-(3,5-difluorophenyl)-2-hydroxybutyl)carbamate (7 mg, 0.0103 mmol) and hydroxyamine hydrochloride (5.7 mg, 0.0514 mmol) in ethanol (0.1 mL) was heated at 80° C. overnight. The reaction mixture was purified by reverse phase prep HPLC to give the title compound (5 mg, 76.2% yield).
$^1$H NMR (CD$_3$OD, 500 MHz) δ ppm 0.75-1.07 (m, 6H), 1.55-1.8 (m, 4H), 2.26 (s, 3H), 2.85-3.6 (m, 9H), 3.80 (s, 3H), 4.0-4.3 (m, 6H), 6.75-7.35 (m, 7H), 7.58 (s, 1H), 7.85 (s, 1H), 7.96 (s, 1H). HPLC retention time: 2.03 min (method A). MS (ESI) (M+H)$^+$ 639.39.

EXAMPLE 15

N$^1$-((2S,3R)-4-(3-methoxybenzylamino)-1-(3,5-difluorophenyl)-3-hydroxybutan-2-yl)-5-((E)-1-(allyloxyimino)ethyl)-N$^3$-methyl-N$^3$-propylisophthalamide hydrochloride

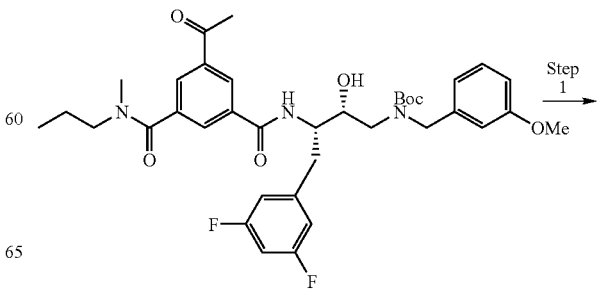

-continued

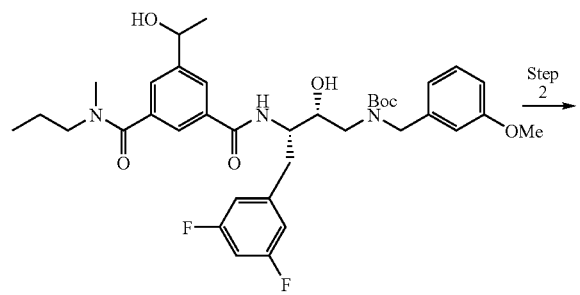

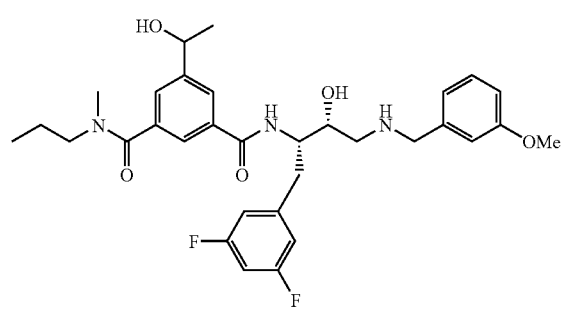

Step 1: Preparation of tert-butyl 3-methoxybenzyl((2R, 3S)-3-(3-(benzamido)-5-(1-(hydroxyethyl)benzamido)-4-(3,5-difluorophenyl)-2-hydroxybutyl)carbamate. tert-butyl 3-methoxybenzyl((2R,3S)-3-(3-acetyl-5-(benzamido)benzamido)-4-(3,5-difluorophenyl)-2-hydroxybutyl)carbamate (12 mg, 0.0176 mmol) in methanol (0.2 ml) was treated with sodium borohydride (0.9 mg, 0.024 mmol), the reaction mixture was stirred at room temperature for 2 h. then concentrated. After partitioning between ethyl acetate and water, the organic layer was separated and concentrated, the resulting product was used as is in the next step: HPLC retention time: 2.14 min (method A). MS (ESI) (M+H)+ 684.34.

Step 2: Preparation of $N^1$-((2S,3R)-4-(3-methoxybenzylamino)-1-(3,5-difluorophenyl)-3-hydroxybutan-2-yl)-5-((E)-1-(allyloxyimino)ethyl)-$N^3$-methyl-$N^3$-propylisophthalamide. tert-Butyl 3-methoxybenzyl((2R,3S)-3-(3-(benzamido)-5-(1-(hydroxyethyl)benzamido)-4-(3,5-difluorophenyl)-2-hydroxybutyl)carbamate (from step 1, 0.0176 mmol) in methanol (0.1 ml) was treated with HCl (1 M solution in ether, 0.1 mL) and the mixture was stirred at room temperature overnight. The reaction mixture was concentrated and purified by reverse phase prep HPLC to give the title compound (9 mg, 87.8% yield). $^1$H NMR (CD$_3$OD, 500 MHz) δ ppm 0.7-1.1 (m, 3H), 1.46 (m, 3H), 1.5-1.8 (m, 2H), 2.8-3.57 (m, 9H), 3.82 (s, 3H), 3.9-4.3 (m, 4H), 4.8-4.95 (m, 2H), 6.7-7.4 (m, 7H), 7.48 (s, 1H), 7.55 (s, 1H), 7.72 (s, 1H). HPLC retention time: 1.673 min (method A). MS (ESI) (M+H)+ 584.33.

EXAMPLE 16

$N^1$-((2S,3R)-4-(3-methoxybenzylamino)-1-(3,5-difluorophenyl)-3-hydroxybutan-2-yl)-3-acetyl-5-(methylsulfonyl)benzamide TFA salt

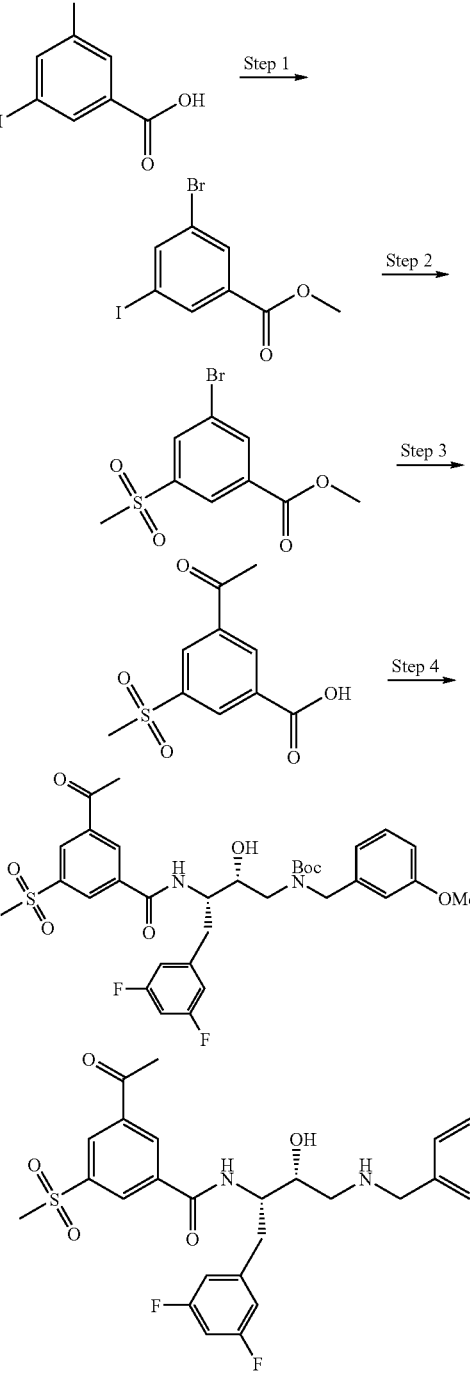

Step 1: Preparation of methyl 3-bromo-5-iodobenzoate. A stirred, cloudy solution of 3-bromo-5-iodobenzoic acid (10 g, 30.59 mmol) and concentrated sulfuric acid (0.60 mL) in MeOH (65 mL) was heated under reflux for 15 h. The resulting clear, light yellow solution was then allowed to cool to room temperature and was concentrated under vacuum. The residual yellow solid was dissolved in ethyl acetate (100 mL), washed with saturated sodium bicarbonate, dried over sodium sulfate, filtered and concentrated in vacuo to give the title compound (10 g, 96% yield) as a light yellow solid: $^1$H NMR (CD$_3$OD, 500 MHz) δ ppm 3.93 (3H, s), 8.12 (1H, m), 8.15 (1H, m), 8.29 (1H, m). HPLC retention time: 2.335 min (method A). MS (ESI) (M+H)$^+$ 340.00.

Step 2: Preparation of methyl 3-bromo-5-(methylsulfonyl) benzoate. To a sealable tube equipped with a stir bar were added (CuOTf)$_2$·PhH (164 mg, 0.29 mmol), sodium methanesulfinate (847.8 mg, 7.06 mmol) and 3-bromo-5-iodobenzoate (2.0 g, 5.88 mmol). The tube was then covered with a rubber septa and a nitrogen atmosphere was established. N,N'-dimethylethylenediamine (54.6 mg, 0.07 mL, 0.588 mmol) and anhydrous DMSO (5.88 mL) were added via syringe and the septa was replaced by a Teflon-coated screw cap and the reaction vessel was placed in a 110° C. oil bath. After stirred for 20 h, the reaction mixture was allowed to cool to room temperature, diluted with ethyl acetate (60 mL) and filtered through a pad of silica gel. The filtrate was washed with H$_2$O (100 mL) twice, brine (100 mL), dried over sodium sulfate, filtered and concentrated under vacuum. The crude mixture was purified by reverse phase prep HPLC to give the title compound (760 mg): $^1$H NMR (CD$_3$OD, 500 MHz) δ ppm 3.21 (3H, s), 3.99 (3H, s), 8.36 (1H, m), 8.46 (1H, m), 8.50 (1H, m). HPLC retention time: 1.578 min (method A). MS (ESI) (M+H)$^+$ 292.00.

Step 3: Preparation of methyl 3-acetyl-5-(methylsulfonyl) benzoic acid. A mixture of methyl 3-bromo-5-(methylsulfonyl)benzoate (66 mg, 0.226 mmol), 1-(vinyloxy)butane (45.3 mg, 0.06 mL, 0.452 mmol), palladium acetate (1.5 mg, 0.0068 mmol), DPPP (6.1 mg, 0.015 mmol) and potassium carbonate (37.5 mg, 0.27 mmol) in DMF (0.6 mL) and H$_2$O (0.07 mL) in a Smith process vial was heated at 122° C. in microwave for 3 h. The reaction mixture was cooled down to room temperature and hydrolyzed by addition of 5% HCl (1 mL) slowly. The reaction mixture was worked up by extraction with ethyl acetate and concentration under vacuum. The crude mixture was purified by reverse phase prep HPLC to give the title compound (16 mg): $^1$H NMR (CD$_3$OD, 500 MHz) δ ppm 2.74 (3H, s), 3.24 (3H, s), 8.70 (1H, m), 8.75 (1H, m), 8.87 (1H, m). HPLC retention time: 1.037 min (method A). MS (ESI) (M+H)$^+$ 243.10.

Step 4: Preparation of tert-butyl 3-methoxybenzyl((2R,3S)-3-(3-acetyl-5-(methylsulfonyl)benzamido)-4-(3,5-difluorophenyl)-2-hydroxybutyl)carbamate. A mixture of methyl 3-acetyl-5-(methylsulfonyl)benzoic acid (52 mg, 0.215 mmol), HATU (98 mg, 0.258 mmol) and Hunig's base (111.1 mg, 0.15 mL, 0.86 mmol) in DMF (1.0 mL) was stirred for 10 min and then tert-butyl 3-methoxybenzyl((2R,3S)-3-amino-4-(3,5-difluorophenyl)-2-hydroxybutyl)-carbamate (94 mg, 0.215 mmol) was added. The reaction mixture was stirred at room temperature overnight. The reaction mixture was diluted with ethyl acetate, washed with H$_2$O 3 times and concentrated under vacuum. The crude mixture was purified by reverse phase prep HPLC to give the title compound (70 mg): $^1$H NMR (CD$_3$OD, 500 MHz) δ ppm 1.48 (9H, s), 2.70 (3H, s), 2.87-2.90 (1H, m), 3.11-3.15 (2H, m), 3.20 (3H, s), 3.37 (1H, m), 3.76 (3H, s), 3.79-3.80 (1H, m), 3.99 (1H, m), 4.33-4.39 (1H, m), 4.43-4.47 (1H, m), 6.73 (1H, m), 6.80-6.83 (3H, m), 6.91 (2H, m), 7.21-7.25 (1H, m), 8.45 (1H, m), 8.54 (1H, m), 8.61 (1H, m). HPLC retention time: 2.022 min (method B). MS (ESI) (M+H)$^+$ 661.14.

Step 5: Preparation of N$^1$-((2S,3R)-4-(3-methoxybenzylamino)-1-(3,5-difluorophenyl)-3-hydroxybutan-2-yl)-3-acetyl-5-(methylsulfonyl)benzamide TFA salt. Tert-butyl 3-methoxybenzyl((2R,3S)-3-(3-acetyl-5-(methylsulfonyl) benzamido)-4-(3,5-difluorophenyl)-2-hydroxybutyl)carbamate (6.0 mg) was dissolved in MeOH (0.2 mL) and treated with HCl (1.0 M solution in ether, 0.2 mL) and the mixture was stirred at room temperature overnight. The reaction mixture was concentrated and purified by reverse phase prep HPLC to give the title compound (4 mg): $^1$H NMR (CD$_3$OD, 500 MHz) δ ppm 2.62-2.70 (1H, m), 2.71 (3H, s), 2.89 (1H, m), 3.08 (1H, m), 3.21 (3H, s), 3.39 (1H, dd, J=5, 15 Hz), 3.80 (3H, s), 4.01 (1H, m), 4.24 (2H, m), 4.28-4.33 (1H, m), 6.77 (1H, m), 6.91-6.92 (2H, m), 6.96 (1H, m), 7.05-7.08 (2H, m), 7.35 (1H, m), 8.40 (1H, m), 8.48 (1H, m), 8.64 (1H, m). HPLC retention time: 1.562 min (method A). MS (ESI) (M+H)$^+$ 561.22.

EXAMPLE 17

N-((2S,3R)-4-(3-methoxybenzylamino)-1-(3,5-difluorophenyl)-3-hydroxybutan-2-yl)-3-((E)-1-(methoxyimino)ethyl)-5-(methylsulfonyl)benzamide TFA salt

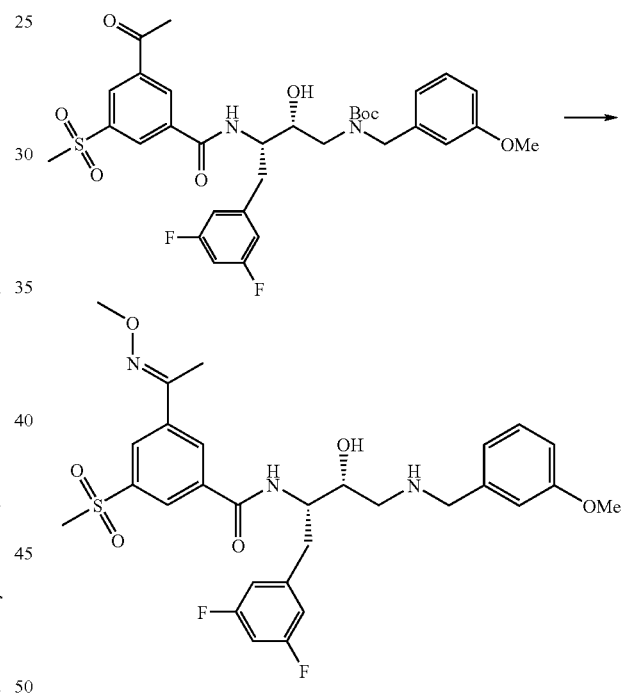

A mixture of tert-butyl 3-methoxybenzyl((2R,3S)-3-(3-acetyl-5-(methylsulfonyl)benzamido)-4-(3,5-difluorophenyl)-2-hydroxybutyl)carbamate (6.0 mg, 0.0091 mmol) and methoxyamine hydrochloride (1.5 mg, 0.018 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (3 mg): $^1$H NMR (CD$_3$OD, 500 MHz) δ ppm 2.29 (3H, s), 2.88 (1H, m), 3.08 (1H, m), 3.18 (3H, s), 3.22 (1H, m), 3.39 (1H, dd, J=5, 15 Hz), 3.80 (3H, s), 3.99 (1H, m), 4.06 (3H, s), 4.20-4.30 (3H, m), 6.78 (1H, m), 6.91-6.94 (2H, m), 6.97 (1H, m), 7.05-7.08 (2H, m), 7.35 (1H, m), 8.17 (1H, m), 8.19 (1H, m), 8.38 (1H, m). HPLC retention time: 1.683 min (method B). MS (ESI) (M+H)$^+$ 590.31.

EXAMPLE 18

N-((2S,3R)-4-(3-methoxybenzylamino)-1-(3,5-difluorophenyl)-3-hydroxybutan-2-yl)-3-((E)-1-(benzyloxyimino)ethyl)-5-(methylsulfonyl)benzamide TFA salt

EXAMPLE 19

N-((2S,3R)-4-(3-methoxybenzylamino)-1-(3,5-difluorophenyl)-3-hydroxybutan-2-yl)-3-(methylsulfonyl)-5-((E)-1-(propoxyimino)ethyl)benzamide TFA salt

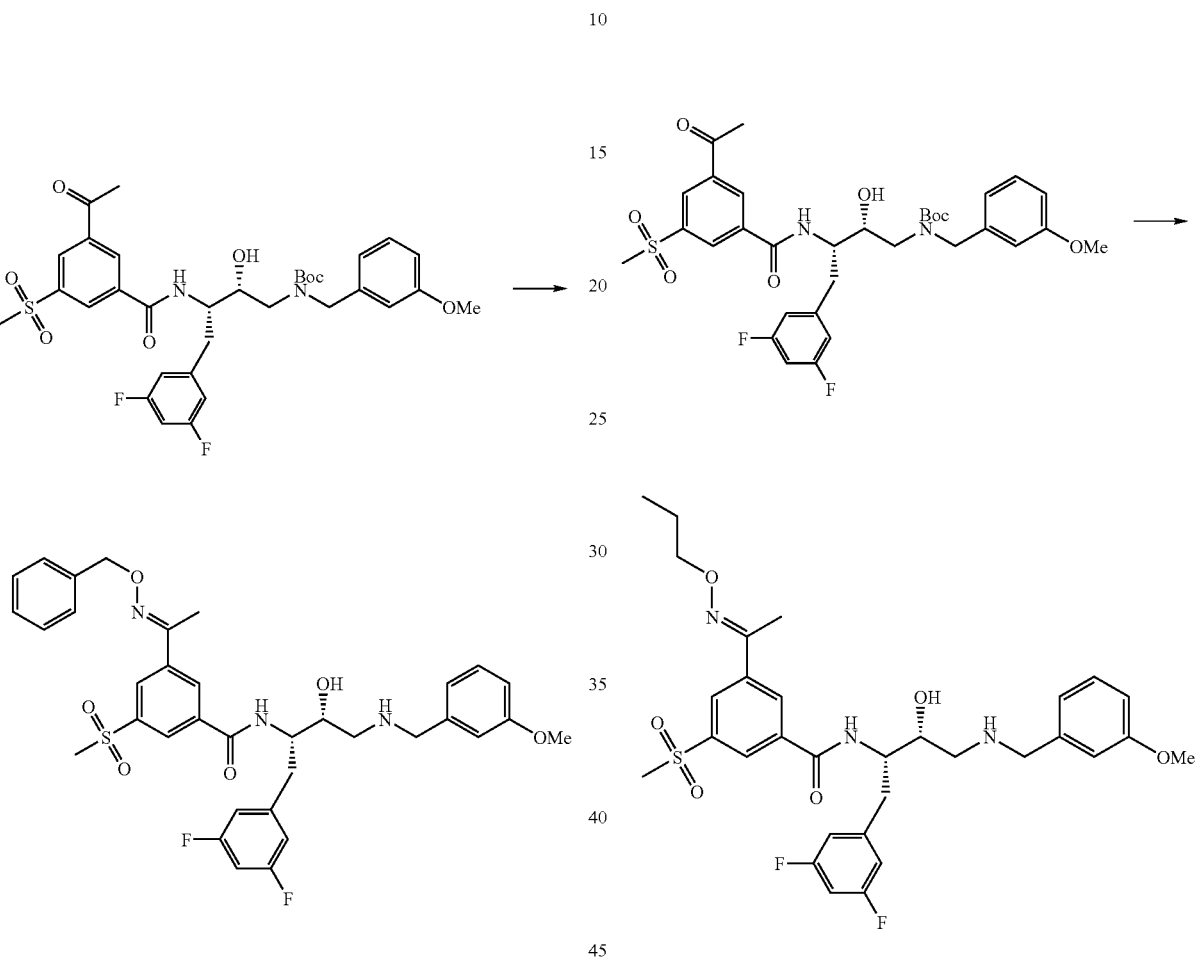

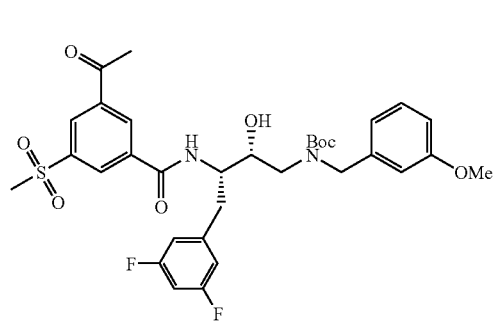

A mixture of tert-butyl 3-methoxybenzyl((2R,3S)-3-(3-acetyl-5-(methylsulfonyl)benzamido)-4-(3,5-difluorophenyl)-2-hydroxybutyl)carbamate (6.0 mg, 0.0091 mmol) and benzoxyamine hydrochloride (2.9 mg, 0.018 mmol) in ethanol (0.1 mL) was heated at 80° C. for 3 h. The reaction mixture was cooled down to room temperature, treated with HCl (1.0 M solution in ether, 0.1 mL) and stirred overnight. The mixture was concentrated and purified by reverse phase prep HPLC to give the title compound (6.1 mg): $^1$H NMR (CD$_3$OD, 500 MHz) δ ppm 2.34 (3H, s), 2.84 (1H, m), 3.08 (1H, m), 3.17 (3H, s), 3.21 (1H, m), 3.38 (1H, m), 3.78 (3H, s), 3.98 (1H, m), 4.20-4.30 (3H, m), 5.31 (2H, s), 6.78 (1H, m), 6.90-6.92 (2H, m), 6.95 (1H, m), 7.05-7.07 (2H, m), 7.30-7.34 (2H, m), 7.38 (2H, m), 7.42-7.44 (2H, m), 8.16 (1H, m), 8.18 (1H, m), 8.38 (1H, m). HPLC retention time: 1.902 min (method B). MS (ESI) (M+H)$^+$ 666.29.

A mixture of tert-butyl 3-methoxybenzyl((2R,3S)-3-(3-acetyl-5-(methylsulfonyl)benzamido)-4-(3,5-difluorophenyl)-2-hydroxybutyl)carbamate (6.0 mg, 0.0091 mmol) and propyloxyamine hydrochloride (2.0 mg, 0.018 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (5 mg): $^1$H NMR (CD$_3$OD, 500 MHz) δ ppm 0.99 (3H, m), 1.75 (2H, m), 2.27 (3H, s), 2.84 (1H, dd, J=15, 20 Hz), 3.04 (1H, m), 3.14 (3H, s), 3.18 (1H, dd, J=5, 15 Hz), 3.35 (1H, dd, J=5, 15 Hz), 3.76 (3H, s), 3.95 (1H, m), 4.16-4.27 (5H, m), 6.74 (1H, m), 6.86-6.90 (2H, m), 6.93 (1H, m), 7.01-7.04 (2H, m), 7.31 (1H, t, J=10 Hz), 8.13 (1H, m), 8.15 (1H, m), 8.34 (1H, m). HPLC retention time: 1.903 min (method A). MS (ESI) (M+H)$^+$ 618.23.

EXAMPLE 20

N-((2S,3R)-4-(3-methoxybenzylamino)-1-(3,5-difluorophenyl)-3-hydroxybutan-2-yl)-3-((E)-1-(isobutoxyimino)ethyl)-5-(methylsulfonyl)benzamide TFA salt

EXAMPLE 21

N-((2S,3R)-4-(3-methoxybenzylamino)-1-(3,5-difluorophenyl)-3-hydroxybutan-2-yl)-3-((E)-1-(allyloxyimino)ethyl)-5-(methylsulfonyl)benzamide TFA salt

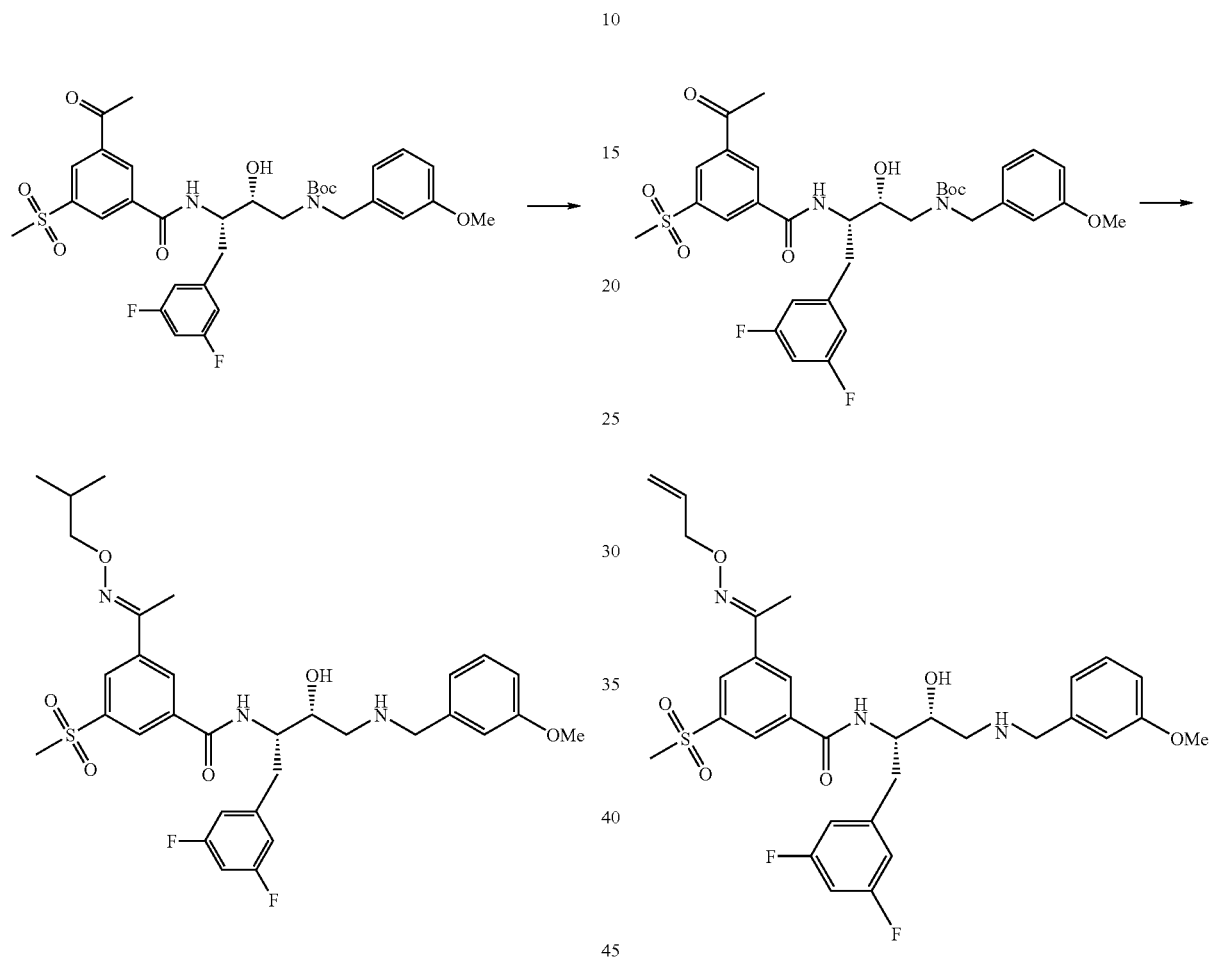

A mixture of tert-butyl 3-methoxybenzyl((2R,3S)-3-(3-acetyl-5-(methylsulfonyl)benzamido)-4-(3,5-difluorophenyl)-2-hydroxybutyl)carbamate (6.0 mg, 0.0091 mmol) and isobutylhydroxylamine hydrochloride (2.3 mg, 0.018 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (4.9 mg): $^1$H NMR (CD$_3$OD, 500 MHz) δ ppm 0.97 (6H, d, J=10 Hz), 2.05 (1H, m), 2.28 (3H, s), 2.84 (1H, dd, J=15, 20 Hz), 3.04 (1H, dd, J=10, 15 Hz), 3.14 (3H, s), 3.18 (1H, dd, J=5, 15 Hz), 3.36 (1H, m), 3.76 (3H, s), 3.94 (1H, dt, J=5, 10 Hz), 4.02 (2H, d, J=5 Hz), 4.16-4.27 (3H, m), 6.74 (1H, m), 6.88-6.90 (2H, m), 6.93 (1H, m), 7.02-7.04 (2H, m), 7.31 (1H, t, J=10 Hz), 8.13 (1H, m), 8.15 (1H, m), 8.33 (1H, m). HPLC retention time: 1.980 min (method A). MS (ESI) (M+H)$^+$ 632.26.

A mixture of tert-butyl 3-methoxybenzyl((2R,3S)-3-(3-acetyl-5-(methylsulfonyl)benzamido)-4-(3,5-difluorophenyl)-2-hydroxybutyl)carbamate (6.0 mg, 0.0091 mmol) and allylhydroxylamine hydrochloride (2.0 mg, 0.018 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (4.7 mg): $^1$H NMR (CD$_3$OD, 500 MHz) δ ppm 2.29 (3H, s), 2.84 (1H, dd, J=15, 20 Hz), 3.04 (1H, dd, J=10, 15 Hz), 3.14 (3H, s), 3.18 (1H, dd, J=5, 15 Hz), 3.35 (1H, dd, J=5, 15 Hz), 3.76 (3H, s), 3.94 (1H, dt, J=5, 10 Hz), 4.16-4.27 (3H, m), 4.74 (2H, m), 5.22 (1H, m), 5.32 (1H, m), 6.06 (1H, m), 6.75 (1H, m), 6.86-6.90 (2H, m), 6.93 (1H, m), 7.01-7.04 (2H, m), 7.31 (1H, t, J=10 Hz), 8.13 (1H, m), 8.15 (1H, m), 8.34 (1H, m). HPLC retention time: 1.842 min (method A). MS (ESI) (M+H)$^+$ 616.23.

EXAMPLE 22

N-[(1S,2R)-1-(3,5-difluoro-benzyl)-2-hydroxy-3-(3-methoxy-benzylamino)-propyl]-3-(1,1-dioxo-1$\lambda^6$-[1,2]thiazinan-2-yl)-5-acetyl-benzamide TFA salt

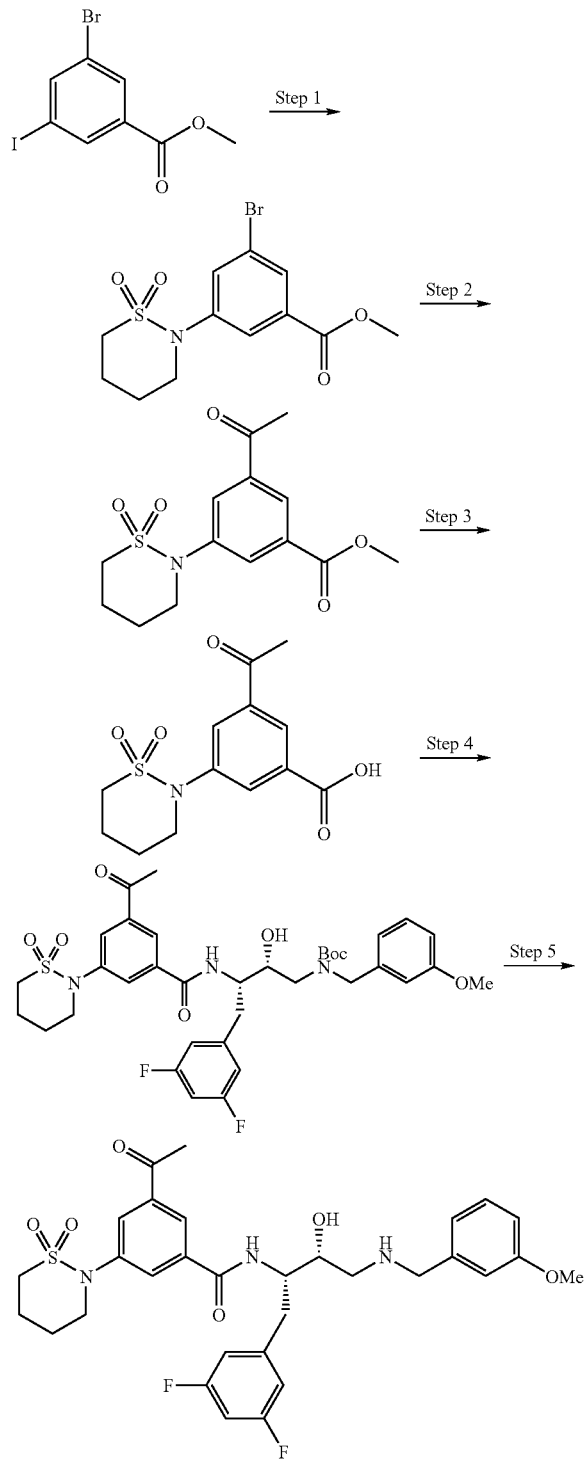

Step 1: Preparation of 3-bromo-5-(1,1-dioxo-1$\lambda^6$-[1,2]thiazinan-2-yl)-benzoic acid methyl ester. To a sealable tube equipped with a stir bar were added 3-bromo-5-iodobenzoate (2.0 g, 5.88 mmol), cesium carbonate (2.85 g, 8.82 mmol), tris(dibenzylideneacetone)dipalladium (0) (27.1 mg, 0.029 mmol) and xant phos (51 mg, 0.088 mmol) in toluene (45 mL) followed by [1,2]thiazinane 1,1-dioxide (902 mg, 6.47 mmol). The resulting mixture was stirred at 10° C. for 16 h, cooled to room temperature and diluted with ethyl acetate. The organic phase was washed with saturated sodium bicarbonate solution, dried over magnesium sulfate, filtered and concentrated under vacuum. The crude mixture was purified by reverse phase prep HPLC to give the title compound (1.7 g, 84% yield): $^1$H NMR (CD$_3$OD, 500 MHz) δ ppm 1.93-1.97 (2H, m), 2.30-2.35 (2H, m), 3.30 (2H, t, J=5 Hz), 3.78 (2H, t, J=5 Hz), 3.94 (3H, s), 7.76 (1H, m), 7.93 (1H, m), 8.06 (1H, m). HPLC retention time: 1.772 min (method A). MS (ESI) (M+H)$^+$ 348.06.

Step 2: Preparation of 3-acetyl-5-(1,1-dioxo-1$\lambda^6$-[1,2]thiazinan-2-yl)-benzoic acid methyl ester. A mixture of 3-bromo-5-(1,1-dioxo-1$\lambda^6$-[1,2]thiazinan-2-yl)-benzoic acid methyl ester (500 mg, 1.44 mmol), 1-(vinyloxy)butane (288.6 mg, 0.37 mL, 2.88 mmol), palladium acetate (9.6 mg, 0.043 mmol), DPPP (39.2 mg, 0.095 mmol) and potassium carbonate (238.5 mg, 1.73 mmol) in DMF (3.8 mL) and H$_2$O (0.45 mL) in a Smith process vial was heated at 122° C. in microwave for 3 h. The reaction mixture was cooled down to room temperature and hydrolyzed by addition of 5% HCl (6 mL) slowly. The reaction mixture was worked up by extraction with ethyl acetate and concentration under vacuum. The crude mixture was purified by reverse phase prep HPLC to give the title compound (200 mg): $^1$H NMR (CD$_3$OD, 500 MHz) δ ppm 1.93-2.01 (2H, m), 2.31-2.37 (2H, m), 2.67 (3H, s), 3.27-3.30 (2H, m), 3.83 (2H, t, J=5 Hz), 3.98 (3H, s), 8.14 (1H, m), 8.19 (1H, m), 8.51 (1H, m). HPLC retention time: 1.448 min (method A). MS (ESI) (M+H)$^+$ 312.13.

Step 3: Preparation of 3-acetyl-5-(1,1-dioxo-1$\lambda^6$-[1,2]thiazinan-2-yl)-benzoic acid. To a solution of 3-acetyl-5-(1,1-dioxo-1$\lambda^6$-[1,2]thiazinan-2-yl)-benzoic acid methyl ester (100 mg, 0.32 mmol) in a mixture of THF (0.3 mL), MeOH (0.6 mL) and H$_2$O (1.5 mL) was added LiOH (23.1 mg, 0.96 mmol) and the mixture was stirred at room temperature for 1 h. The mixture was concentrated and partitioned between ethyl acetate and H$_2$O. The aqueous layer was washed with ethyl acetate twice and acidified with 1N HCl solution to pH around 2~3. The aqueous layer was extracted with ethyl acetate 3 times and the combined organic layers were dried over sodium sulfate and concentrated under vacuum to give the title compound (93 mg): $^1$H NMR (CD$_3$OD, 500 MHz) δ ppm 1.93-1.99 (2H, m), 2.31-2.37 (2H, m), 2.67 (3H, s), 3.27-3.30 (2H, m), 3.83 (2H, t, J=5 Hz), 8.13 (1H, m), 8.20 (1H, m), 8.52 (1H, m). HPLC retention time: 1.292 min (method A). MS (ESI) (M+Na)+ 320.14.

Step 4: Preparation of [(2R,3S)-3-[3-acetyl-5-(1,1-dioxo-1$\lambda^6$-[1,2]thiazinan-2-yl)-benzoylamino]-4-(3,5-difluoro-phenyl)-2-hydroxy-butyl]-(3-methoxy-benzyl)-carbamic acid tert-butyl ester. A mixture of 3-acetyl-5-(1,1-dioxo-1$\lambda^6$-[1,2]thiazinan-2-yl)-benzoic acid (68.1 mg, 0.23 mmol), HATU (104.6 mg, 0.275 mmol) and Hunig's base (118.5 mg, 0.16 mL, 0.917 mmol) in DMF (1.1 mL) was stirred for 10 min and then tert-butyl 3-methoxybenzyl((2R,3S)-3-amino-4-(3,5-difluorophenyl)-2-hydroxybutyl)carbamate (100 mg, 0.23 mmol) was added. The reaction mixture was stirred at room temperature for 2 h. The reaction mixture was diluted with ethyl acetate, washed with H$_2$O 3 times and concentrated under vacuum to give the title compound (164 mg): $^1$H NMR (CD$_3$OD, 500 MHz) δ ppm 1.48 (9H, s), 1.93-2.00 (2H, m), 2.32-2.38 (2H, m), 2.64 (3H, s), 2.88 (1H, dd, J=10, 15 Hz), 3.08-3.15 (1H, m), 3.20-3.23 (1H, m), 3.27-3.39 (2H, m), 3.38 (1H, m), 3.74-3.82 (6H, m), 3.96-4.00 (1H, m), 4.20-4.29 (2H, m), 6.76 (1H, m), 6.91-6.92 (3H, m), 7.05-7.08 (2H, m), 7.35 (1H, m), 8.04 (1H, m), 8.07 (1H, m), 8.11 (1H, m). HPLC retention time: 2.112 min (method A). MS (ESI) (M+Na)$^+$ 738.28.

Step 5: Preparation of N-[(1S,2R)-1-(3,5-difluoro-benzyl)-2-hydroxy-3-(3-methoxy-benzylamino)-propyl]-3-(1,1-dioxo-1λ⁶-[1,2]thiazinan-2-yl)-5-acetyl-benzamide TFA salt. [(2R,3S)-3-[3-acetyl-5-(1,1-dioxo-1λ⁶-[1,2]thiazinan-2-yl)-benzoylamino]-4-(3,5-difluoro-phenyl)-2-hydroxy-butyl]-(3-methoxy-benzyl)-carbamic acid tert-butyl ester (15 mg) was treated with HCl (1 M solution in ether, 0.20 mL) and the mixture was stirred at room temperature for overnight. The reaction mixture was concentrated under vacuum and purified by reverse phase prep HPLC to give the title compound (15 mg): ¹H NMR (CD₃OD, 500 MHz) δ ppm 1.96-1.98 (2H, m), 2.34-2.36 (2H, m), 2.64 (3H, s), 2.85-2.90 (1H, dd, J=13.0, 8.0 Hz), 3.06-3.10 (1H, dd, J=13.0, 8.0 Hz), 3.20-3.23 (1H, m), 3.37-3.40 (1H, m), 3.78-3.80 (5H, m), 3.97-4.01 (3H, m), 4.21-4.29 (3H, m), 6.75-6.79 (1H, m), 7.05-7.08 (2H, m), 7.33-7.36 (1H, m), 7.80 (1H, m), 8.07 (1H, m), and 8.11 (1H, m). HPLC retention time: 1.62 min (method B). MS (ESI) (M+H)⁺ 616.23.

EXAMPLE 23

N-[(1S,2R)-1-(3,5-difluoro-benzyl)-2-hydroxy-3-(3-methoxy-benzylamino)-propyl]-3-(1,1-dioxo-1λ⁶-[1,2]thiazinan-2-yl)-5-(1-hydroxy-ethyl)-benzamide TFA salt

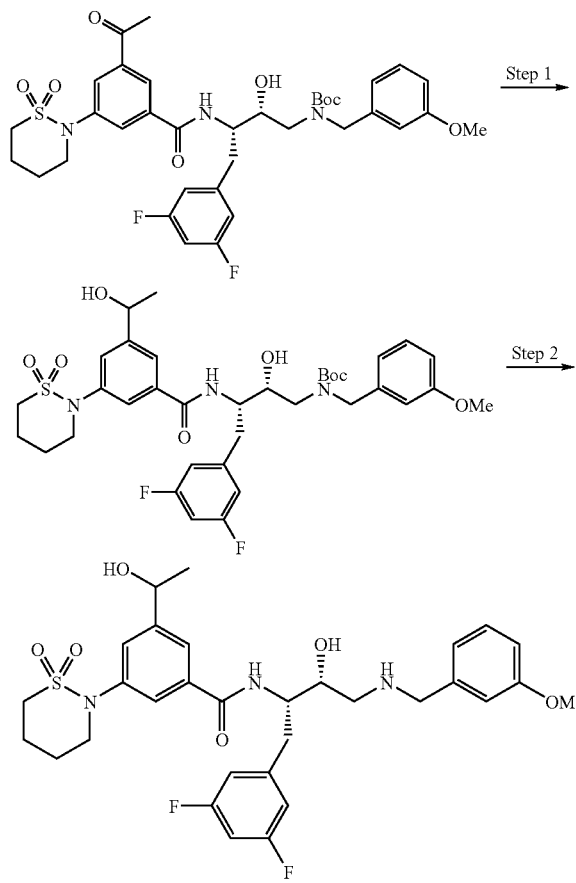

Step 1: Preparation of {(2R,3S)-4-(3,5-difluoro-phenyl)-3-[3-(1,1-dioxo-1λ⁶-[1,2]thiazinan-2-yl)-5-(1-hydroxy-ethyl)-benzoylamino]-2-hydroxy-butyl}-(3-methoxy-benzyl)-carbamic acid tert-butyl ester. [(2R,3S)-3-[3-Acetyl-5-(1,1-dioxo-1λ⁶-[1,2]thiazinan-2-yl)-benzoylamino]-4-(3,5-difluoro-phenyl)-2-hydroxy-butyl]-(3-methoxy-benzyl)-carbamic acid tert-butyl ester (16 mg, 0.022 mmol) was dissolved in MeOH (0.2 mL) and sodium borohydride (1.13 mg, 0.03 mmol) was added. The reaction mixture was stirred at room temperature for 2 h. The mixture was concentrated and partitioned between ethyl acetate and H₂O. The organic layer was separated and concentrated to give the title compound which was used in the next step without further purification: HPLC retention time: 2.073 min (method A). MS (ESI) (M+H)⁺ 718.30.

Step 2: Preparation of N-[(1S,2R)-1-(3,5-difluoro-benzyl)-2-hydroxy-3-(3-methoxy-benzylamino)-propyl]-3-(1,1-dioxo-1λ⁶-[1,2]thiazinan-2-yl)-5-(1-hydroxy-ethyl)-benzamide TFA salt. {(2R,3S)-4-(3,5-Difluoro-phenyl)-3-[3-(1,1-dioxo-1λ⁶-[1,2]thiazinan-2-yl)-5-(1-hydroxy-ethyl)-benzoylamino]-2-hydroxy-butyl}-(3-methoxy-benzyl)-carbamic acid tert-butyl ester (about 0.022 mmol) was dissolved in MeOH (0.2 mL) and treated with HCl (1.0 M solution in ether, 0.2 mL) and the mixture was stirred at room temperature overnight. The reaction mixture was concentrated and purified by reverse phase prep HPLC to give the title compound (8 mg): ¹H NMR (CD₃OD, 500 MHz) δ ppm 1.44 (3H, m), 1.92-1.97 (2H, m), 2.31-2.36 (2H, m), 2.87 (1H, m), 3.08 (1H, m), 3.21 (1H, m), 3.29 (2H, m), 3.38 (1H, dd, J=5, 15 Hz), 3.74 (2H, t, J=5 Hz), 3.82 (3H, s), 3.96 (1H, m), 4.20-4.27 (3H, m), 4.78-4.90 (1H, m), 6.77 (1H, m), 6.90-6.93 (2H, m), 7.00 (1H, m), 7.06-7.10 (2H, m), 7.36 (1H, m), 7.44 (1H, m), 7.54-7.55 (2H, m). HPLC retention time: 1.567 min (method A). MS (ESI) (M+H)⁺ 618.29.

EXAMPLE 24

N-[(1S,2R)-1-(3,5-difluoro-benzyl)-2-hydroxy-3-(3-methoxy-benzylamino)-propyl]-3-(1,1-dioxo-1λ⁶-[1,2]thiazinan-2-yl)-5-{1-[(E)-methoxyimino]-ethyl}-benzamide TFA salt

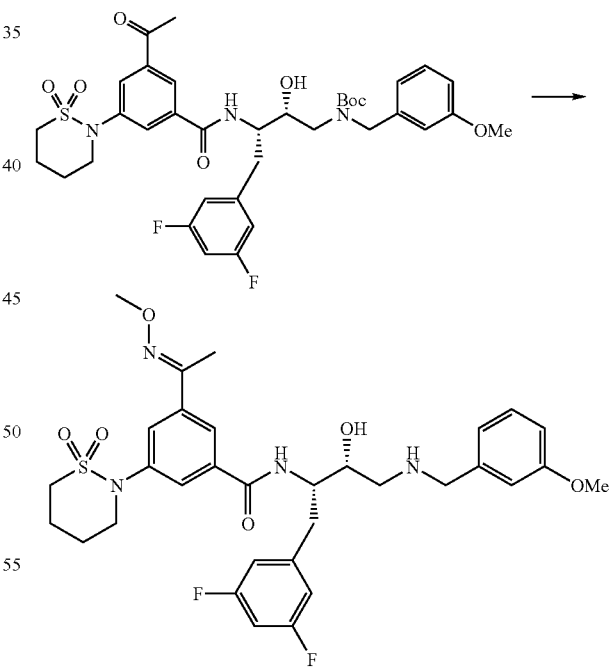

A mixture of [(2R,3S)-3-[3-acetyl-5-(1,1-dioxo-1λ⁶-[1,2]thiazinan-2-yl)-benzoylamino]-4-(3,5-difluoro-phenyl)-2-hydroxy-butyl]-(3-methoxy-benzyl)-carbamic acid tert-butyl ester (6.0 mg, 0.00839 mmol) and methoxyamine hydrochloride (0.0168 mmol) in ethanol (0.1 mL) was heated at 80° C. for 3 h. The reaction mixture was cooled down to room temperature, treated with HCl (1.0 M solution in ether, 0.1 mL) and stirred overnight. The mixture was concentrated and purified by reverse phase prep HPLC to give the title compound (4 mg): ¹H NMR (CD₃OD, 500 MHz) δ ppm 1.94-1.98 (2H, m), 2.23 (3H, s), 2.32-2.37 (2H, m), 2.87 (1H, m), 3.08 (1H, dd, J=10, 15 Hz), 3.21 (1H, m), 3.38 (2H, m), 3.75 (2H, t, J=5 Hz), 3.81 (3H, s), 3.96 (1H, m), 4.00 (1H, m), 4.02 (3H, s), 4.20-4.27 (3H, m), 6.78 (1H, m), 6.91-6.94 (2H, m), 6.98 (1H, m), 7.05-7.09 (2H, m), 7.36 (1H, m), 7.56 (1H, m), 7.79 (1H, m), 7.81 (1H, m). HPLC retention time: 1.823 min (method A). MS (ESI) (M+H)⁺ 645.25.

EXAMPLE 25

N-[(1S,2R)-1-(3,5-difluoro-benzyl)-2-hydroxy-3-(3-methoxy-benzylamino)-propyl]-3-(1,1-dioxo-1λ⁶-[1,2]thiazinan-2-yl)-5-{1-[(E)-benzyloxyimino]-ethyl}-benzamide TFA salt

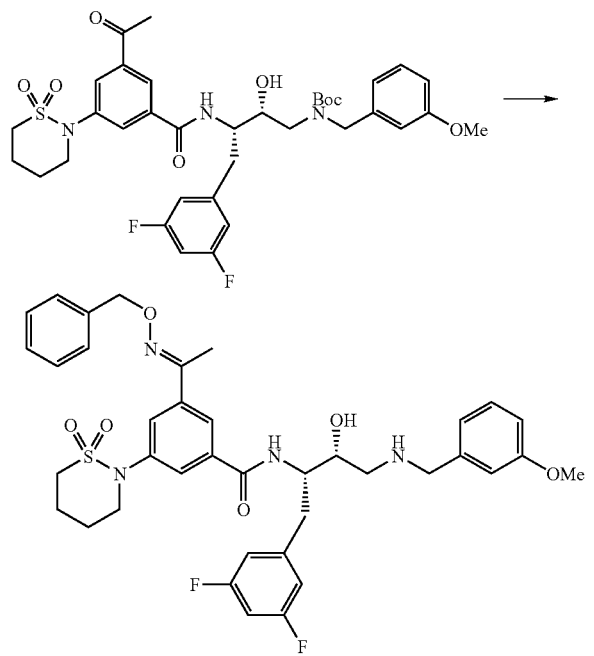

A mixture of [(2R,3S)-3-[3-acetyl-5-(1,1-dioxo-1λ⁶-[1,2]thiazinan-2-yl)-benzoylamino]-4-(3,5-difluoro-phenyl)-2-hydroxy-butyl]-(3-methoxy-benzyl)-carbamic acid tert-butyl ester (6.0 mg, 0.00839 mmol) and benzoxyamine hydrochloride (2.7 mg, 0.0168 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (4.0 mg): ¹H NMR (CD₃OD, 500 MHz) δ ppm 1.91-1.95 (2H, m), 2.26 (3H, s), 2.30-2.34 (2H, m), 2.84 (1H, m), 3.04 (1H, dd, J=10, 15 Hz), 3.18 (1H, m), 3.27-3.29 (1H, m), 3.36 (1H, dd, J=5, 15 Hz), 3.73 (2H, m), 3.76 (3H, s), 3.94 (1H, m), 3.98 (1H, m), 4.18-4.24 (3H, m), 5.25 (2H, s), 6.76 (1H, m), 6.89-6.90 (2H, m), 6.94 (1H, m), 7.02-7.05 (2H, m), 7.27-7.36 (4H, m), 7.39-7.41 (2H, m), 7.51 (1H, m), 7.78 (2H, m). HPLC retention time: 2.013 min (method A). MS (ESI) (M+H)⁺ 721.29.

EXAMPLE 26

N-[(1S,2R)-1-(3,5-difluoro-benzyl)-2-hydroxy-3-(3-methoxy-benzylamino)-propyl]-3-(1,1-dioxo-1λ⁶-[1,2]thiazinan-2-yl)-5-{1-[(E)-propoxyimino]-ethyl}-benzamide TFA salt

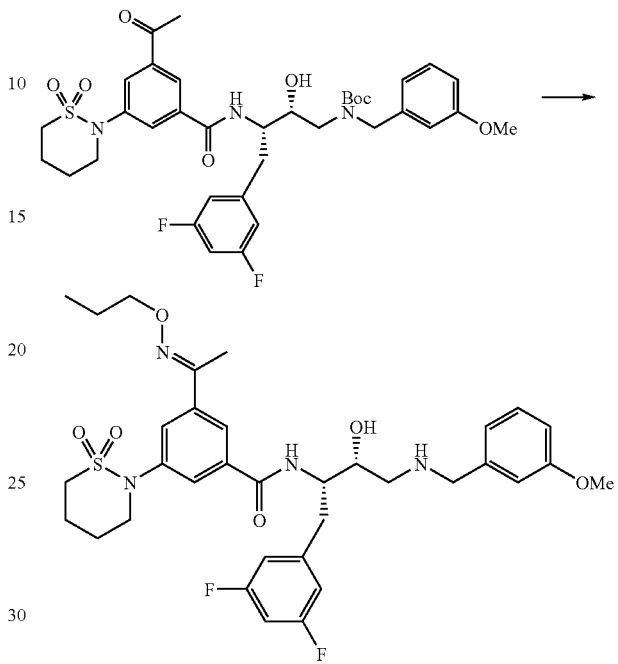

A mixture of [(2R,3S)-3-[3-acetyl-5-(1,1-dioxo-1λ⁶-[1,2]thiazinan-2-yl)-benzoylamino]-4-(3,5-difluoro-phenyl)-2-hydroxy-butyl]-(3-methoxy-benzyl)-carbamic acid tert-butyl ester (6.0 mg, 0.00839 mmol) and propyloxyamine hydrochloride (1.9 mg, 0.0168 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (4.5 mg): ¹H NMR (CD₃OD, 500 MHz) δ ppm 1.02 (3H, m), 1.77 (2H, m), 1.91-1.98 (2H, m), 2.25 (3H, s), 2.32-2.37 (2H, m), 2.87 (1H, m), 3.08 (1H, dd, J=10, 15 Hz), 3.18 (1H, m), 3.21 (1H, m), 3.29 (2H, m), 3.38 (1H, m), 3.75 (2H, t, J=5 Hz), 3.80 (3H, s), 3.96 (1H, m), 4.19 (2H, t, J=5 Hz), 4.22-4.27 (3H, m), 6.78 (1H, m), 6.91-6.94 (2H, m), 6.98 (1H, m), 7.05-7.09 (2H, m), 7.35 (1H, m), 7.55 (1H, m), 7.79 (1H, m), 7.81 (1H, m). HPLC retention time: 1.953 min (method A). MS (ESI) (M+H)⁺ 673.30.

EXAMPLE 27

N-[(1S,2R)-1-(3,5-difluoro-benzyl)-2-hydroxy-3-(3-methoxy-benzylamino)-propyl]-3-(1,1-dioxo-1λ⁶-[1,2]thiazinan-2-yl)-5-{1-[(E)-isobutoxyimino]-ethyl}-benzamide TFA salt

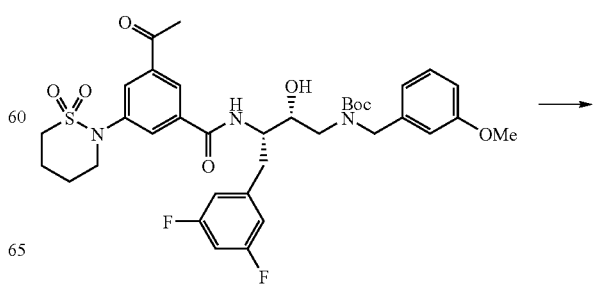

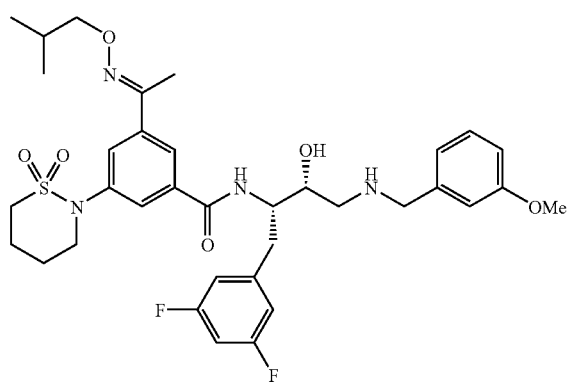

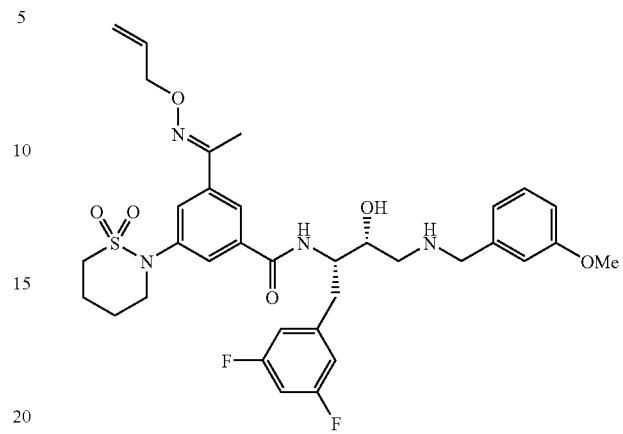

A mixture of [(2R,3S)-3-[3-acetyl-5-(1,1-dioxo-1λ⁶-[1,2] thiazinan-2-yl)-benzoylamino]-4-(3,5-difluoro-phenyl)-2-hydroxy-butyl]-(3-methoxy-benzyl)-carbamic acid tert-butyl ester (6.0 mg, 0.00839 mmol) and isobutylhydroxylamine hydrochloride (2.1 mg, 0.0168 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (4.7 mg): ¹H NMR (CD₃OD, 500 MHz) δ ppm 1.00 (6H, d, J=10 Hz), 1.94-1.98 (2H, m), 2.03-2.11 (1H, m), 2.26 (3H, s), 2.32-2.37 (2H, m), 2.87 (1H, m), 3.08 (1H, dd, J=10, 15 Hz), 3.21 (1H, m), 3.29 (2H, m), 3.38 (1H, m), 3.75 (2H, t, J=5 Hz), 3.80 (3H, s), 3.96 (1H, m), 4.01 (2H, d, J=10 Hz), 4.20-4.27 (3H, m), 6.78 (1H, m), 6.91-6.93 (2H, m), 6.98 (1H, m), 7.05-7.09 (2H, m), 7.35 (1H, m), 7.55 (1H, m), 7.79 (1H, m), 7.81 (1H, m). HPLC retention time: 2.037 min (method A). MS (ESI) (M+H)⁺ 687.33.

A mixture of [(2R,3S)-3-[3-acetyl-5-(1,1-dioxo-1λ⁶-[1,2] thiazinan-2-yl)-benzoylamino]-4-(3,5-difluoro-phenyl)-2-hydroxy-butyl]-(3-methoxy-benzyl)-carbamic acid tert-butyl ester (6.0 mg, 0.00839 mmol) and allylhydroxylamine hydrochloride (1.8 mg, 0.01678 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (5.0 mg): ¹H NMR (CD₃OD, 500 MHz) δ ppm 1.94-1.98 (2H, m), 2.27 (3H, s), 2.86 (1H, dd, J=10, 15 Hz), 3.08 (1H, dd, J=10, 15 Hz), 3.21 (1H, m), 3.29 (2H, m), 3.38 (1H, m), 3.75 (2H, t, m), 3.80 (3H, s), 3.96 (1H, m), 4.20-4.27 (3H, m), 4.74 (2H, m), 5.24 (1H, m), 5.34 (1H, m), 6.08 (1H, m), 6.78 (1H, m), 6.91-6.93 (2H, m), 6.98 (1H, m), 7.05-7.08 (2H, m), 7.35 (1H, m), 7.56 (1H, m), 7.79 (1H, m), 7.81 (1H, m). HPLC retention time: 1.915 min (method A). MS (ESI) (M+H)⁺ 671.29.

EXAMPLE 28

N-[(1S,2R)-1-(3,5-difluoro-benzyl)-2-hydroxy-3-(3-methoxy-benzylamino)-propyl]-3-(1,1-dioxo-1λ⁶-[1,2]thiazinan-2-yl)-5-{1-[(E)-allyloxyimino]-ethyl}-benzamide TFA salt

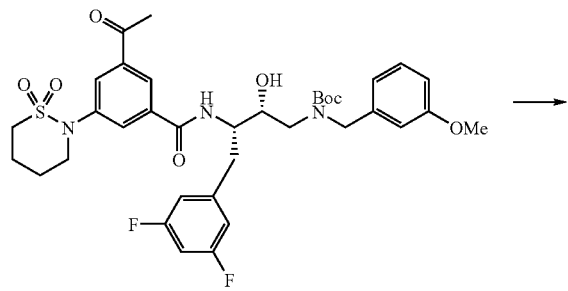

EXAMPLE 29 tert-butyl 3-methoxybenzyl((2R,3S)-3-(3-acetyl-5-(N-methylmethan-2-ylsulfonamido)benzamido)-4-(3,5-difluorophenyl)-2-hydroxybutyl)carbamate

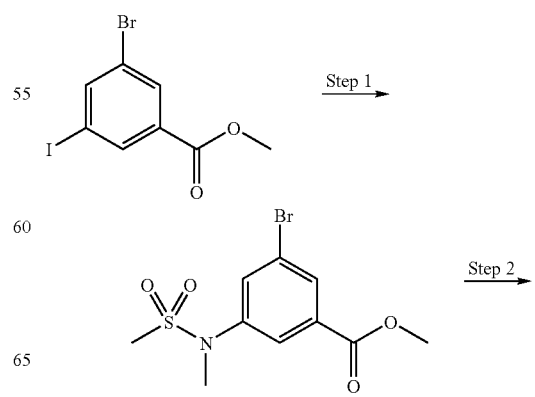

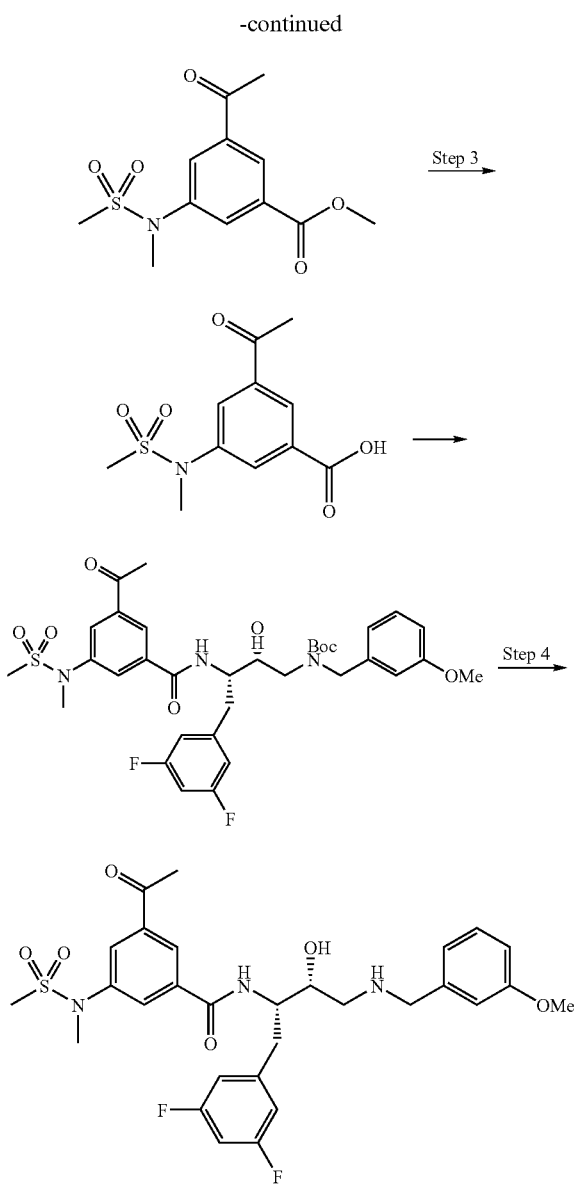

Step 1: Preparation of methyl 3-bromo-5-(N-methylmethan-2-ylsulfonamido)benzoate. To a sealable tube equipped with a stir bar were added 3-bromo-5-iodobenzoate (1.56 g, 4.59 mmol), cesium carbonate (2.22 g, 6.88 mmol), tris(dibenzylideneacetone)dipalladium (0) (21.2 mg, 0.023 mmol) and xant phos (41.2 mg, 0.069 mmol) in toluene (35 mL) followed by N-methylmethanesulfonamide (500 mg, 4.59 mmol). The resulting mixture was stirred at 100° C. for 27 h, cooled to room temperature and diluted with ethyl acetate. The organic phase was washed with saturated sodium bicarbonate solution, dried over sodium sulfate, filtered and concentrated under vacuum. The crude mixture was purified by reverse phase prep HPLC to give the title compound (1.0 g, 68% yield): $^1$H NMR (CD$_3$OD, 500 MHz) δ ppm 2.96 (3H, s), 3.36 (3H, s), 3.95 (3H, s), 7.89 (1H, m), 8.06 (1H, m), 8.07 (1H, m). HPLC retention time: 1.700 min (method A). MS (ESI) (M+H)$^+$ 322.07.

Step 2: Preparation of methyl 3-acetyl-5-(N-methylmethan-2-ylsulfonamido)benzoate. A mixture of methyl 3-bromo-5-(N-methylmethan-2-ylsulfonamido)benzoate (462 mg, 1.44 mmol), 1-(vinyloxy)butane (288.6 mg, 0.37 mL, 2.88 mmol), palladium acetate (9.6 mg, 0.043 mmol), DPPP (39.2 mg, 0.095 mmol) and potassium carbonate (238.5 mg, 1.73 mmol) in DMF (3.8 mL) and H$_2$O (0.45 mL) in a Smith process vial was heated at 122° C. in microwave for 3 h. The reaction mixture was cooled down to room temperature and hydrolyzed by addition of 5% HCl (6 mL) slowly. The reaction mixture was worked up by extraction with ethyl acetate and concentration under vacuum. The crude mixture was purified by reverse phase prep HPLC to give the title compound (173 mg): $^1$H NMR (CD$_3$OD, 500 MHz) δ ppm 2.68 (3H, s), 2.96 (3H, s), 3.41 (3H, s), 3.98 (3H, s), 8.24 (1H, m), 8.28 (1H, m), 8.52 (1H, m). HPLC retention time: 1.367 min (method A). MS (ESI) (M+H)$^+$ 286.15.

Step 3: Preparation of 3-acetyl-5-(N-methylmethan-2-ylsulfonamido)benzoic acid. Methyl 3-acetyl-5-(N-methylmethan-2-ylsulfonamido)benzoate (110 mg, 0.386 mmol) was dissolved in a mixture of THF (0.4 mL), MeOH (0.8 mL) and H$_2$O (2.0 mL), treated with LiOH (27.7 mg, 1.16 mmol) and the mixture was stirred at room temperature for 2 h. The mixture was concentrated and partitioned between ethyl acetate and H$_2$O. The aqueous layer was washed with ethyl acetate twice and acidified with 1N HCl solution to pH around 2~3. The aqueous layer was extracted with ethyl acetate 3 times and the combined organic layers were dried over sodium sulfate and concentrated under vacuum to give the title compound (100 mg): $^1$H NMR (CD$_3$OD, 500 MHz) δ ppm 2.64 (3H, s), 2.93 (3H, s), 3.37 (3H, s), 8.20 (1H, m), 8.25 (1H, m), 8.49 (1H, m). HPLC retention time: 1.223 min (method A). MS (ESI) (M+Na)$^+$ 272.13.

Step 4: Preparation of tert-butyl 3-methoxybenzyl((2R,3S)-3-(3-acetyl-5-(N-methylmethan-2-ylsulfonamido)benzamido)-4-(3,5-difluorophenyl)-2-hydroxybutyl)carbamate. A mixture of 3-acetyl-5-(N-methylmethan-2-ylsulfonamido)benzoic acid (100 mg, 0.369 mmol), HATU (168.4 mg, 0.443 mmol) and Hunig's base (190.6 mg, 0.26 mL, 1.48 mmol) in DMF (2.0 mL) was stirred for 10 min and then tert-butyl 3-methoxybenzyl((2R,3S)-3-amino-4-(3,5-difluorophenyl)-2-hydroxybutyl)carbamate (160 mg, 0.369 mmol) was added. The reaction mixture was stirred at room temperature for 2 h. The reaction mixture was diluted with ethyl acetate, washed with H$_2$O 3 times and concentrated under vacuum to give the title compound (249 mg): HPLC retention time: 2.092 min (method A). MS (ESI) (M+Na)$^+$ 690.30.

Step 5: Preparation of N-((2S,3R)-4-(3-methoxybenzylamino)-1-(3,5-difluorophenyl)-3-hydroxybutan-2-yl)-3-acetyl-5-(N-methylmethan-2-ylsulfonamido)benzamide TFA salt. Tert-butyl 3-methoxybenzyl((2R,3S)-3-(3-acetyl-5-(N-methylmethan-2-ylsulfonamido)benzamido)-4-(3,5-difluorophenyl)-2-hydroxybutyl)carbamate (10 mg, 0.0145 mmol) was dissolved in MeOH (0.1 mL) and treated with HCl (1.0 M solution in ether, 0.1 mL) and the mixture was stirred at room temperature overnight. The reaction mixture was concentrated and purified by reverse phase prep HPLC to give the title compound (7 mg): $^1$H NMR (CD$_3$OD, 500 MHz) δ ppm 2.65 (3H, s), 2.88 (1H, dd, J=10, 15 Hz), 2.97 (3H, s), 3.08 (1H, m), 3.23 (1H, m), 3.38 (1H, dd, J=5, 15 Hz), 3.38 (3H, s), 3.81 (3H, s), 3.99 (1H, m), 4.21-4.30 (3H, m), 6.77 (1H, m), 6.91-6.93 (2H, m), 6.98 (1H, m), 7.06-7.09 (2H, m), 7.35 (1H, m), 7.89 (1H, m), 8.13 (1H, m), 8.17 (1H, m). HPLC retention time: 1.590 min (method A). MS (ESI) (M+H)$^+$ 590.24.

EXAMPLE 30

N-((2S,3R)-4-(3-methoxybenzylamino)-1-(3,5-difluorophenyl)-3-hydroxybutan-2-yl)-3-((E)-1-(methoxyimino)ethyl)-5-(N-methylmethan-2-ylsulfonamido)benzamide TFA salt

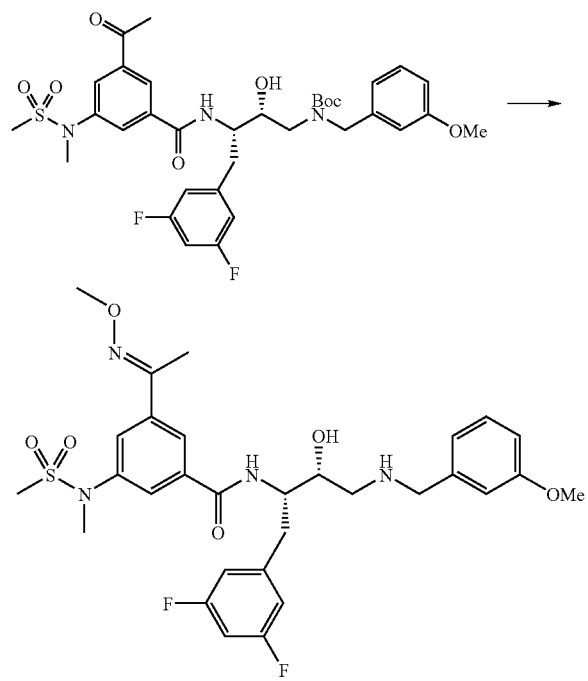

A mixture of tert-butyl 3-methoxybenzyl((2R,3S)-3-(3-acetyl-5-(N-methylmethan-2-ylsulfonamido)benzamido)-4-(3,5-difluorophenyl)-2-hydroxybutyl)carbamate (8.0 mg, 0.0116 mmol) and methoxyamine hydrochloride (1.9 mg, 0.0232 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (5.0 mg): $^1$H NMR (CD$_3$OD, 500 MHz) δ ppm 2.24 (3H, s), 2.87 (1H, m), 2.95 (3H, s), 3.08 (1H, m), 3.22 (1H, m), 3.35 (3H, s), 3.38 (1H, dd, J=5, 15 Hz), 3.81 (3H, s), 3.98 (1H, m), 4.02 (3H, s), 4.21-4.27 (3H, m), 6.78 (1H, m), 6.91-6.94 (2H, m), 6.99 (1H, m), 7.06-7.09 (2H, m), 7.35 (1H, m), 7.65 (1H, m), 7.83 (1H, m), 7.88 (1H, m). HPLC retention time: 1.763 min (method A). MS (ESI) (M+H)$^+$ 619.26.

EXAMPLE 31

N-((2S,3R)-4-(3-methoxybenzylamino)-1-(3,5-difluorophenyl)-3-hydroxybutan-2-yl)-3-((E)-1-(benzyloxyimino)ethyl)-5-(N-methylmethan-2-ylsulfonamido)benzamide TFA salt

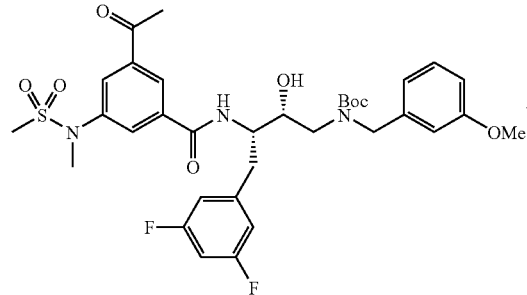

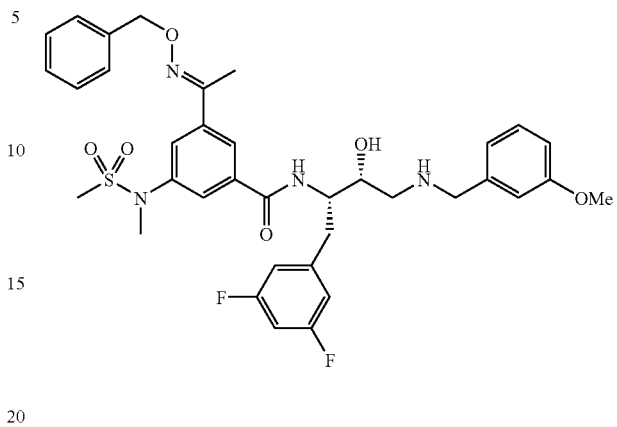

A mixture of tert-butyl 3-methoxybenzyl((2R,3S)-3-(3-acetyl-5-(N-methylmethan-2-ylsulfonamido)benzamido)-4-(3,5-difluorophenyl)-2-hydroxybutyl)carbamate (8.0 mg, 0.0116 mmol) and benzoxyamine hydrochloride (3.7 mg, 0.0232 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (5.5 mg): $^1$H NMR (CD$_3$OD, 500 MHz) δ ppm 2.29 (3H, s), 2.86 (1H, m), 2.94 (3H, s), 3.06 (1H, m), 3.21 (1H, m), 3.34 (3H, s), 3.38 (1H, m), 3.78 (3H, s), 3.97 (1H, m), 4.20-4.27 (3H, m), 5.27 (2H, s), 6.77 (1H, m), 6.90-6.92 (2H, m), 6.96 (1H, m), 7.05-7.08 (2H, m), 7.29-7.38 (4H, m), 7.41-7.43 (2H, m), 7.64 (1H, m), 7.81 (1H, m), 7.87 (1H, m). HPLC retention time: 1.977 min (method A). MS (ESI) (M+H)$^+$ 695.26.

EXAMPLE 32

N-((2S,3R)-4-(3-methoxybenzylamino)-1-(3,5-difluorophenyl)-3-hydroxybutan-2-yl)-3-((E)-1-(propoxyimino)ethyl)-5-(N-methylmethan-2-ylsulfonamido)benzamide TFA salt

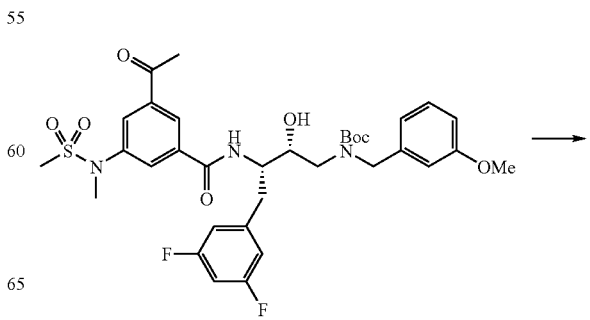

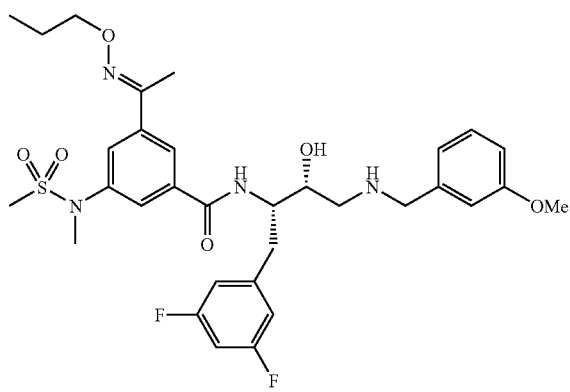

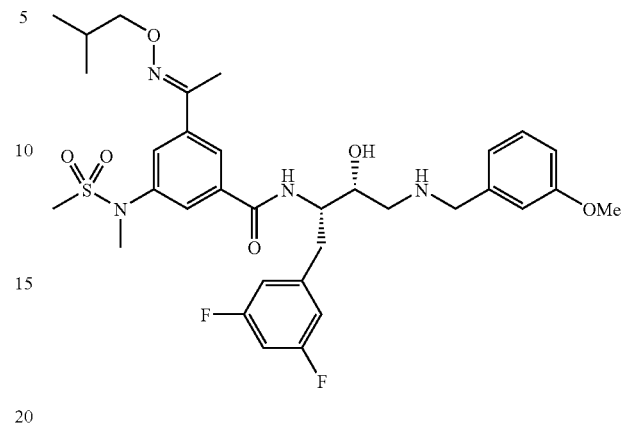

A mixture of tert-butyl 3-methoxybenzyl((2R,3S)-3-(3-acetyl-5-(N-methylmethan-2-ylsulfonamido)benzamido)-4-(3,5-difluorophenyl)-2-hydroxybutyl)carbamate (8.0 mg, 0.0116 mmol) and propyloxyamine hydrochloride (2.6 mg, 0.0232 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (5.2 mg): $^1$H NMR (CD$_3$OD, 500 MHz) δ ppm 1.02 (3H, m), 1.77 (2H, m), 2.26 (3H, s), 2.87 (1H, m), 2.95 (3H, s), 3.08 (1H, m), 3.22 (1H, dd, J=5, 15 Hz), 3.35 (3H, s), 3.38 (1H, dd, J=5, 15 Hz), 3.81 (3H, s), 3.98 (1H, dd, J=5, 10 Hz), 4.19 (2H, m), 4.23-4.27 (3H, m), 6.77 (1H, m), 6.91-6.94 (2H, m), 6.98 (1H, m), 7.06-7.09 (2H, m), 7.35 (1H, t, J=10 Hz), 7.65 (1H, m), 7.83 (1H, m), 7.87 (1H, m). HPLC retention time: 1.927 min (method A). MS (ESI) (M+H)$^+$ 647.25.

A mixture of tert-butyl 3-methoxybenzyl((2R,3S)-3-(3-acetyl-5-(N-methylmethan-2-ylsulfonamido)benzamido)-4-(3,5-difluorophenyl)-2-hydroxybutyl)carbamate (8.0 mg, 0.0116 mmol) and isobutylhydroxylamine hydrochloride (2.9 mg, 0.0232 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (5.1 mg): $^1$H NMR (CD$_3$OD, 500 MHz) δ ppm 1.01 (6H, d, J=5 Hz), 2.07 (1H, m), 2.27 (3H, s), 2.87 (1H, m), 2.95 (3H, s), 3.08 (1H, m), 3.22 (1H, m), 3.35 (3H, s), 3.38 (1H, dd, J=5, 15 Hz), 3.81 (3H, s), 3.98 (1H, dd, J=5, 10 Hz), 4.02 (2H, d, J=5 Hz), 4.21-4.27 (3H, m), 6.77 (1H, m), 6.91-6.94 (2H, m), 6.98 (1H, m), 7.06-7.09 (2H, m), 7.35 (1H, m), 7.65 (1H, m), 7.82 (1H, m), 7.87 (1H, m). HPLC retention time: 1.997 min (method A). MS (ESI) (M+H)$^+$ 661.28.

EXAMPLE 33

N-((2S,3R)-4-(3-methoxybenzylamino)-1-(3,5-difluorophenyl)-3-hydroxybutan-2-yl)-3-((E)-1-(isobutoxyimino)ethyl)-5-(N-methylmethan-2-ylsulfonamido)benzamide TFA salt

EXAMPLE 34

N-((2S,3R)-4-(3-methoxybenzylamino)-1-(3,5-difluorophenyl)-3-hydroxybutan-2-yl)-3-((E)-1-(allyloxyimino)ethyl)-5-(N-methylmethan-2-ylsulfonamido)benzamide TFA salt

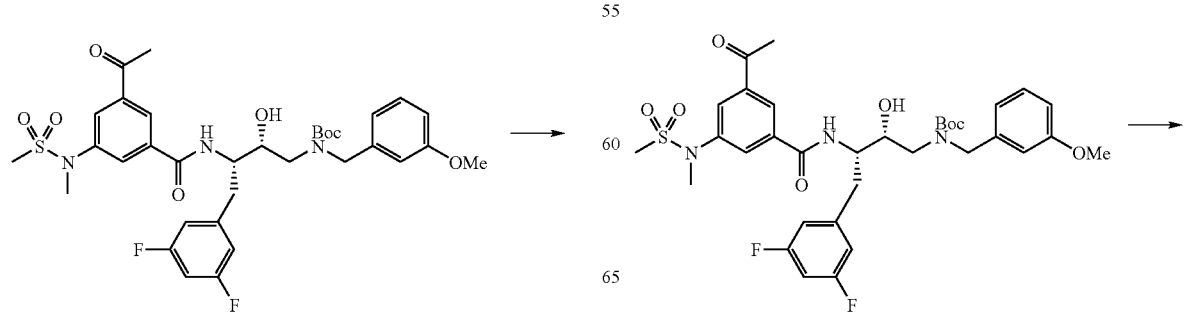

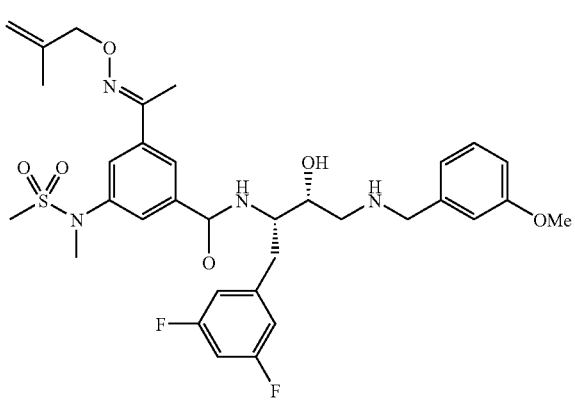

A mixture of tert-butyl 3-methoxybenzyl((2R,3S)-3-(3-acetyl-5-(N-methylmethan-2-ylsulfonamido)benzamido)-4-(3,5-difluorophenyl)-2-hydroxybutyl)carbamate (8.0 mg, 0.0116 mmol) and allylhydroxylamine hydrochloride (2.5 mg, 0.0232 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (5.3 mg): $^1$H NMR (CD$_3$OD, 500 MHz) δ ppm 2.28 (3H, s), 2.86 (1H, dd, J=10, 15 Hz), 2.95 (3H, s), 3.08 (1H, dd, J=10, 15 Hz), 3.22 (1H, m), 3.35 (3H, s), 3.38 (1H, dd, J=5, 15 Hz), 3.80 (3H, s), 3.98 (1H, m), 4.21-4.27 (3H, m), 4.74 (2H, m), 5.24 (1H, m), 5.34 (1H, m), 6.08 (1H, m), 6.78 (1H, m), 6.91-6.94 (2H, m), 6.98 (1H, m), 7.06-7.09 (2H, m), 7.35 (1H, t, J=10 Hz), 7.65 (1H, m), 7.83 (1H, m), 7.88 (1H, m). HPLC retention time: 1.877 min (method A). MS (ESI) (M+H)$^+$ 645.25.

EXAMPLE 35

N-((2S,3R)-4-(3-methoxybenzylamino)-1-(3,5-difluorophenyl)-3-hydroxybutan-2-yl)-3-(1-hydroxyethyl)-5-(N-methylmethan-2-ylsulfonamido)benzamide TFA salt

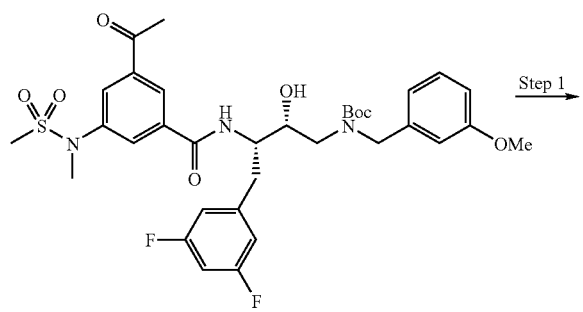

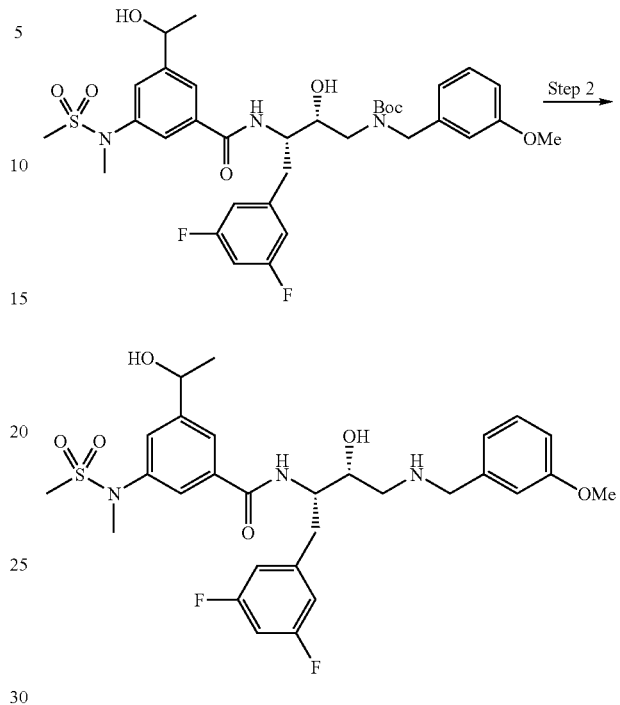

Step 1: Preparation of tert-butyl 3-methoxybenzyl((2R,3S)-4-(3,5-difluorophenyl)-2-hydroxy-3-(3-(1-hydroxyethyl)-5-(N-methylmethan-2-ylsulfonamido)benzamido)butyl)carbamate. Tert-butyl 3-methoxybenzyl-((2R,3S)-3-(3-acetyl-5-(N-methylmethan-2-ylsulfonamido)benzamido)-4-(3,5-difluorophenyl)-2-hydroxybutyl)carbamate (16 mg, 0.023 mmol) was dissolved in MeOH (0.2 mL) and sodium borohydride (1.2 mg, 0.031 mmol) was added. The reaction mixture was stirred at room temperature for 2 h. The mixture was concentrated and partitioned between ethyl acetate and H$_2$O. The organic layer was separated, concentrated and purified by reverse phase pre HPLC to give the title compound (12 mg): HPLC retention time: 2.057 min (method A). MS (ESI) (M+H)$^+$ 692.31.

Step 2: Preparation of N-((2S,3R)-4-(3-methoxybenzylamino)-1-(3,5-difluorophenyl)-3-hydroxybutan-2-yl)-3-(1-hydroxyethyl)-5-(N-methylmethan-2-ylsulfonamido)benzamide TFA salt. tert-butyl 3-methoxybenzyl((2R,3S)-4-(3,5-difluorophenyl)-2-hydroxy-3-(3-(1-hydroxyethyl)-5-(N-methylmethan-2-ylsulfonamido)benzamido)butyl)-carbamate (6.0 mg) was dissolved in MeOH (0.1 mL) and treated with HCl (1.0 M solution in ether, 0.1 mL) and the mixture was stirred at room temperature overnight. The reaction mixture was concentrated and purified by reverse phase prep HPLC to give the title compound (5 mg): $^1$H NMR (CD$_3$OD, 500 MHz) δ ppm 1.46 (3H, m), 1.92-1.97 (2H, m), 2.87 (1H, m), 2.94 (3H, s), 3.08 (1H, dd, J=10, 15 Hz), 3.22 (1H, dd, J=5, 15 Hz), 3.33 (3H, s), 3.38 (1H, m), 3.82 (3H, s), 3.98 (1H, m), 4.20-4.27 (3H, m), 4.85-4.89 (1H, m), 6.77 (1H, m), 6.90-6.92 (2H, m), 7.00 (1H, m), 7.06-7.10 (2H, m), 7.36 (1H, t, J=10 Hz), 7.53 (1H, m), 7.56 (1H, m), 7.62 (1H, m). HPLC retention time: 1.548 min (method A). MS (ESI) (M+H)$^+$ 592.25.

EXAMPLE 36

N-((2S,3R)-4-(3-methoxybenzylamino)-1-(3,5-difluorophenyl)-3-hydroxybutan-2-yl)-3-acetyl-5-(N-phenylmethan-10-ylsulfonamido)benzamide TFA salt

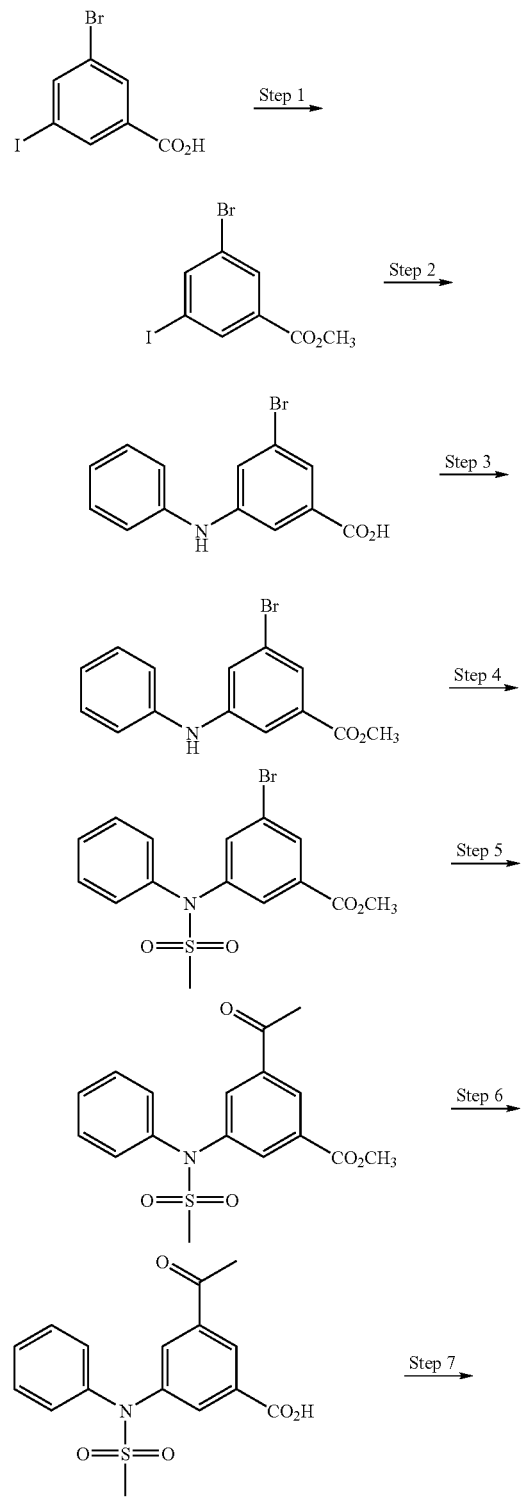

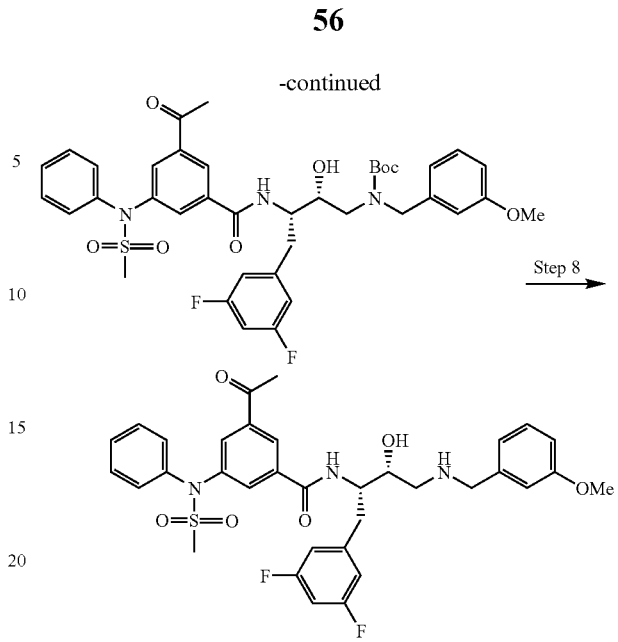

Step 1: Preparation of methyl 3-bromo-5-iodobenzoate. A solution of 3-bromo-5-iodobenzoic acid (10 g, 30.59 mmol) and concentrated sulfuric acid (0.6 ml) in methanol (65 mL) was heated under reflux for 15 hours under nitrogen atmosphere. The resulting clear, light yellow solution was cooled to room temperature and concentrated under vacuum. The yellow solid residue was then dissolved in ethyl acetate (100 ml) and washed with saturated aqueous sodium bicarbonate, dried over sodium sulfate, filtered and concentrated to give the methyl ester as a light yellow solid (10 g, 96% yield): HPLC retention time: 2.333 min (method A). MS (ESI) (M+H)$^+$ 340.86.

Step 2: Preparation of 3-bromo-5-(phenylamino)benzoic acid. A solution of palladium(II) acetate (1.1 mg, 0.005 mmol) and xantphos (8.9 mg, 0.015 mmol) in toluene (8 ml) was stirred at room temperature for 5 min in a sealable tube purged with nitrogen, methyl 3-bromo-5-iodobenzoate (340 mg, 1.0 mmol) and aniline (111.8 mg, 1.2 mmol) were added and let stir for 5 more min, Sodium tert-butoxide (134.6 mg, 1.4 mmol) was then added and the mixture was stirred at room temperature for 5 min before heated up to 80° C. for 3 h. The reaction mixture was cooled down to RT and ether (containing 1% triethylamine) was added, passed through a celite column, dried over sodium sulfate and concentrated under vacuum to give the crude product which was used directly in the next reaction without further purification: HPLC retention time: 2.123 min (method A). MS (ESI) (M+H)$^+$ 292.07.

Step 3: Preparation of methyl 3-bromo-5-(phenylamino) benzoate. The title compound was prepared using the procedures described in Step 1 of Example 36. The crude product was purified by reverse phase prep HPLC to give the title compound. HPLC retention time: 2.305 min (method A). MS (ESI) (M+H)$^+$ 306.11.

Step 4: Preparation of methyl 3-bromo-5-(N-phenylmethan-10-ylsulfonamido)benzoate. Methyl 3-bromo-5-(phenylamino)benzoate (210 mg, 0.686 mmol) in THF (4 ml) was cooled to −78° C. and LDA (0.95 ml, 1.716 mmol) was added dropwise, the resulting mixture was stirred at this temperature for 5 min. Methanesulfonyl chloride (0.13 ml, 1.716 mmol) was then added dropwise and the resulting mixture was allowed to warm to room temperature over 30 min. The reaction mixture was diluted with ethyl acetate and the organic layer was washed with 1N HCl solution, 1N NaOH solution, brine, dried over sodium sulfate and concentrated under vacuum. The crude product was purified by reverse phase prep HPLC to give the title compound (65 mg, 25% yield): HPLC retention time: 1.962 min (method A). MS (ESI) (M+H)⁺ 384.00.

Step 5: methyl 3-acetyl-5-(N-phenylmethan-10-ylsulfonamido)benzoate. The title compound was made from methyl 3-bromo-5-(N-phenylmethan-10-ylsulfonamido)benzoate using the procedures described for Step 4 of Example 1. HPLC retention time: 1.67 min (method A). MS (ESI) (M+H)⁺ 348.00.

Step 6: 3-acetyl-5-(N-phenylmethan-10-ylsulfonamido) benzoic acid. The title compound was made from methyl 3-acetyl-5-(N-phenylmethan-10-ylsulfonamido)benzoate using the procedures described for Step 5 of Example 1. HPLC retention time: 1.535 min (method A). MS (ESI) (M+H)⁺ 334.15.

Step 7: tert-butyl 3-methoxybenzyl((2R,3S)-3-(3-acetyl-5-(N-phenylmethan-10-ylsulfonamido)benzamido)-4-(3,5-difluorophenyl)-2-hydroxybutyl)carbamate. The title compound was made from 3-acetyl-5-(N-phenylmethan-10-ylsulfonamido)benzoic acid using the procedures described for Step 6 of Example 1. HPLC retention time: 2.448 min (method A). MS (ESI) (M+Na)⁺ 751.27.

Step 8: N-((2R,3S)-4-(3-methoxybenzylamino)-1-(3,5-difluorophenyl)-3-hydroxybutan-2-yl)-3-acetyl-5-(N-phenylmethan-10-ylsulfonamido)benzamide. The title compound was made from tert-butyl 3-methoxybenzyl((2R,3S)-3-(3-acetyl-5-(N-phenylmethan-10-ylsulfonamido)benzamido)-4-(3,5-difluorophenyl)-2-hydroxybutyl)carbamate using the procedures described for Step 7 of Example 1. ¹H NMR (CD₃OD, 500 MHz) δ ppm 2.62 (s, 3H), 2.8-3.1 (m, 4H), 3.79 (s, 3H), 3.95-4.3 (m, 4H), 6.75-7.55 (m, 12H), 7.87 (s, 1H), 8.10 (s, 1H), 8.14 (s, 1H). HPLC retention time: 1.75 min (method A). MS (ESI) (M+H)⁺ 652.21.

Examples 37-43 were prepared using the procedures described in Example 9.

EXAMPLE 37

N-((2S,3R)-4-(3-methoxybenzylamino)-1-(3,5-difluorophenyl)-3-hydroxybutan-2-yl)-3-((E)-1-(hydroxyimino)ethyl)-5-(N-phenylmethan-10-ylsulfonamido)benzamide

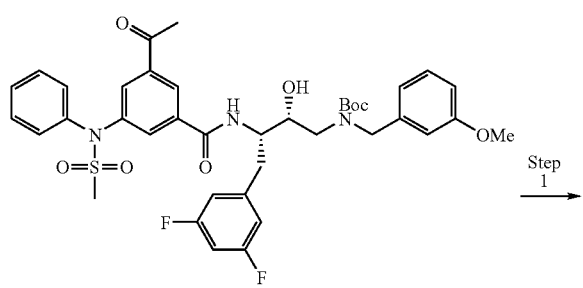

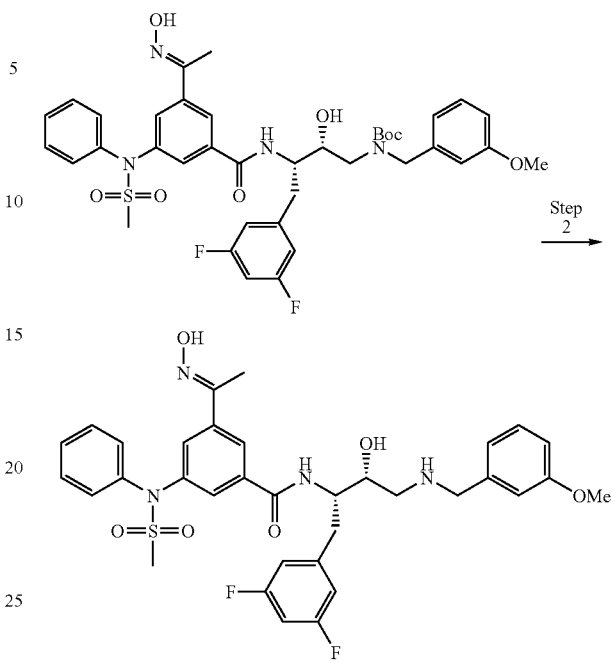

¹H NMR (CD₃OD, 500 MHz) δ ppm 2.62 (s, 3H), 2.8-3.1 (m, 4H), 3.26 (s, 3H), 3.79 (s, 3H), 3.95-4.3 (m, 4H), 6.75-7.5 (m, 12H), 7.87 (s, 1H), 8.11 (s, 1H), 8.14 (s, 1H). HPLC retention time: 1.742 min (method A). MS (ESI) (M+H)⁺ 667.23.

EXAMPLE 38

N-((2S,3R)-4-(3-methoxybenzylamino)-1-(3,5-difluorophenyl)-3-hydroxybutan-2-yl)-3-((E)-1-(methoxyimino)ethyl)-5-(N-phenylmethan-10-ylsulfonamido)benzamide

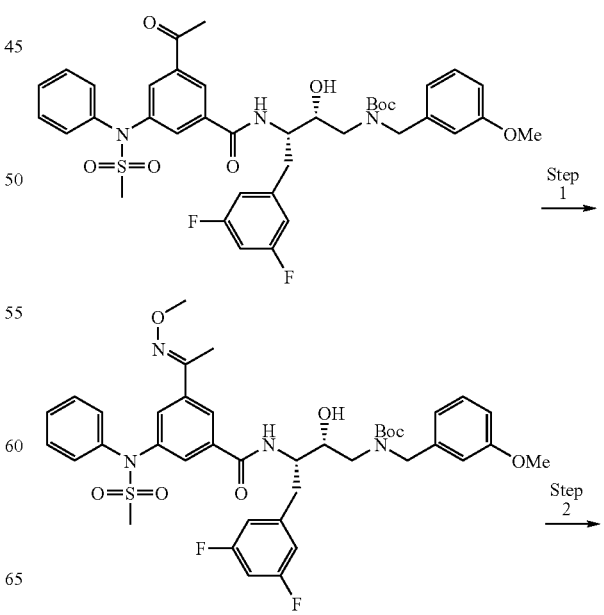

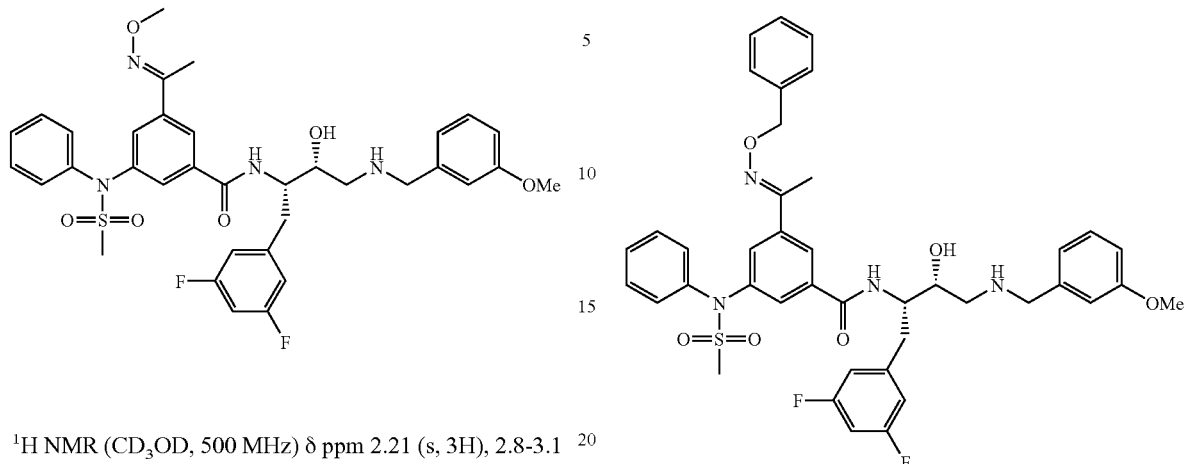

$^1$H NMR (CD$_3$OD, 500 MHz) δ ppm 2.21 (s, 3H), 2.8-3.1 (m, 4H), 3.24 (s, 3H), 3.79 (s, 3H), 3.95-4.0 (m, 1H), 4.01 (s, 3H), 4.15-4.25 (m, 3H), 6.7-7.5 (m, 12H), 7.65 (s, 1H), 7.81 (s, 1H), 7.87 (s, 1H). HPLC retention time: 1.898 min (method A). MS (ESI) (M+H)$^+$ 681.23.

EXAMPLE 39

N-((2S,3R)-4-(3-methoxybenzylamino)-1-(3,5-difluorophenyl)-3-hydroxybutan-2-yl)-3-((E)-1-(benzyloxyimino)ethyl)-5-(N-phenylmethan-10-ylsulfonamido)benzamide

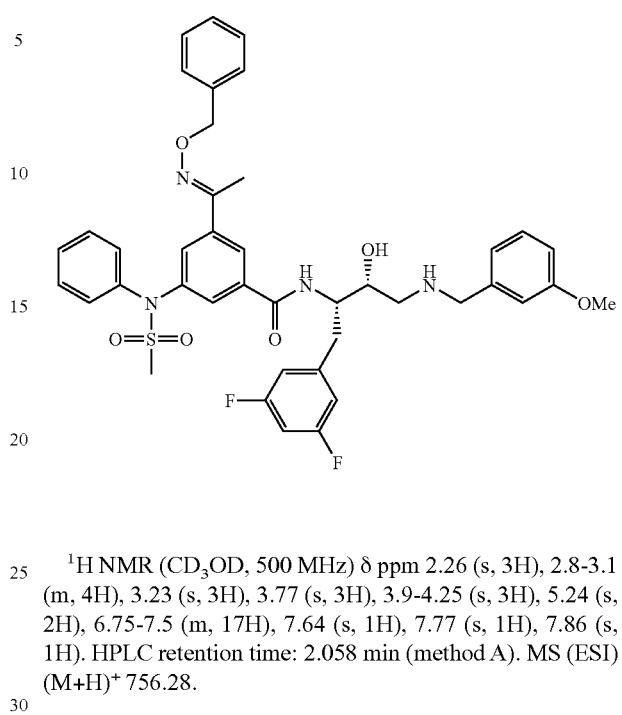

$^1$H NMR (CD$_3$OD, 500 MHz) δ ppm 2.26 (s, 3H), 2.8-3.1 (m, 4H), 3.23 (s, 3H), 3.77 (s, 3H), 3.9-4.25 (s, 3H), 5.24 (s, 2H), 6.75-7.5 (m, 17H), 7.64 (s, 1H), 7.77 (s, 1H), 7.86 (s, 1H). HPLC retention time: 2.058 min (method A). MS (ESI) (M+H)$^+$ 756.28.

EXAMPLE 40

N-((2S,3R)-4-(3-methoxybenzylamino)-1-(3,5-difluorophenyl)-3-hydroxybutan-2-yl)-3-(1-hydroxyethyl)-5-(N-phenylmethan-10-ylsulfonamido)benzamide

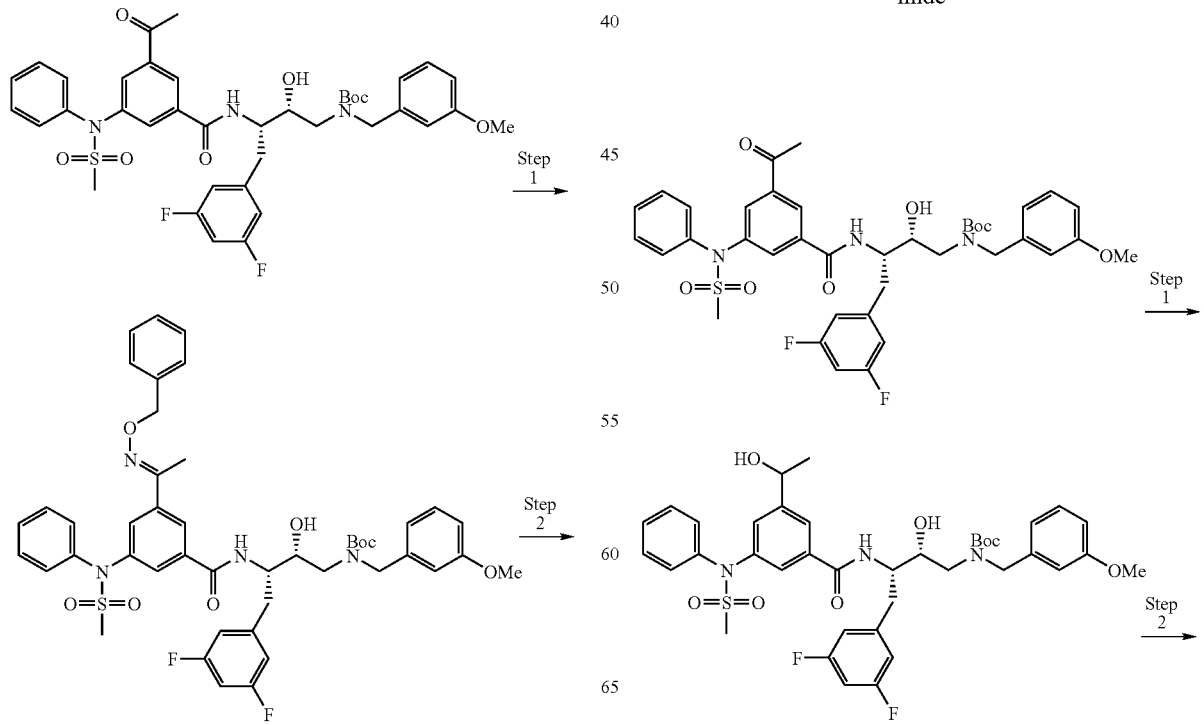

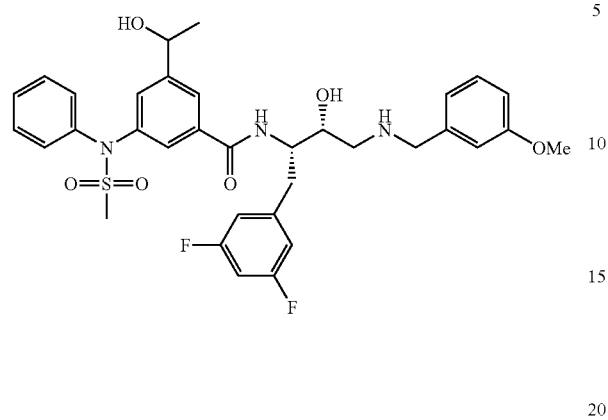

¹H NMR (CD₃OD, 500 MHz) δ ppm 1.43 (d, J=10 Hz, 3H), 2.8-3.1 (m, 4H), 3.23 (s, 3H), 3.81 (s, 3H), 3.95-4.3 (m, 4H), 6.7-7.65 (m, 15H). HPLC retention time: 2.118 min (method A). MS (ESI) (M+H)⁺ 654.21.

EXAMPLE 41

N-((2S,3R)-4-(3-methoxybenzylamino)-1-(3,5-difluorophenyl)-3-hydroxybutan-2-yl)-3-((E)-1-(isobutoxyimino)ethyl)-5-(N-phenylmethan-10-ylsulfonamido)benzamide

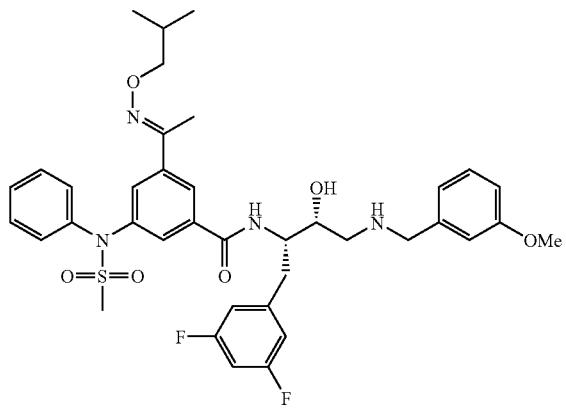

¹H NMR (CD₃OD, 500 MHz) δ ppm 0.99 (d, J=10 Hz, 6H), 2.05 (m, 1H), 2.8-3.1 (m, 4H), 3.24 (s, 3H), 3.79 (s, 3H), 3.9-4.3 (m, 6H), 6.7-7.5 (m, 12H), 7.65 (s, 1H), 7.80 (s, 1H), 7.86 (s, 1H). HPLC retention time: 2.087 min (method A). MS (ESI) (M+H)⁺ 723.32.

EXAMPLE 42

N-((2S,3R)-4-(3-methoxybenzylamino)-1-(3,5-difluorophenyl)-3-hydroxybutan-2-yl)-3-((E)-1-(allyloxyimino)ethyl)-5-(N-phenylmethan-10-ylsulfonamido)benzamide

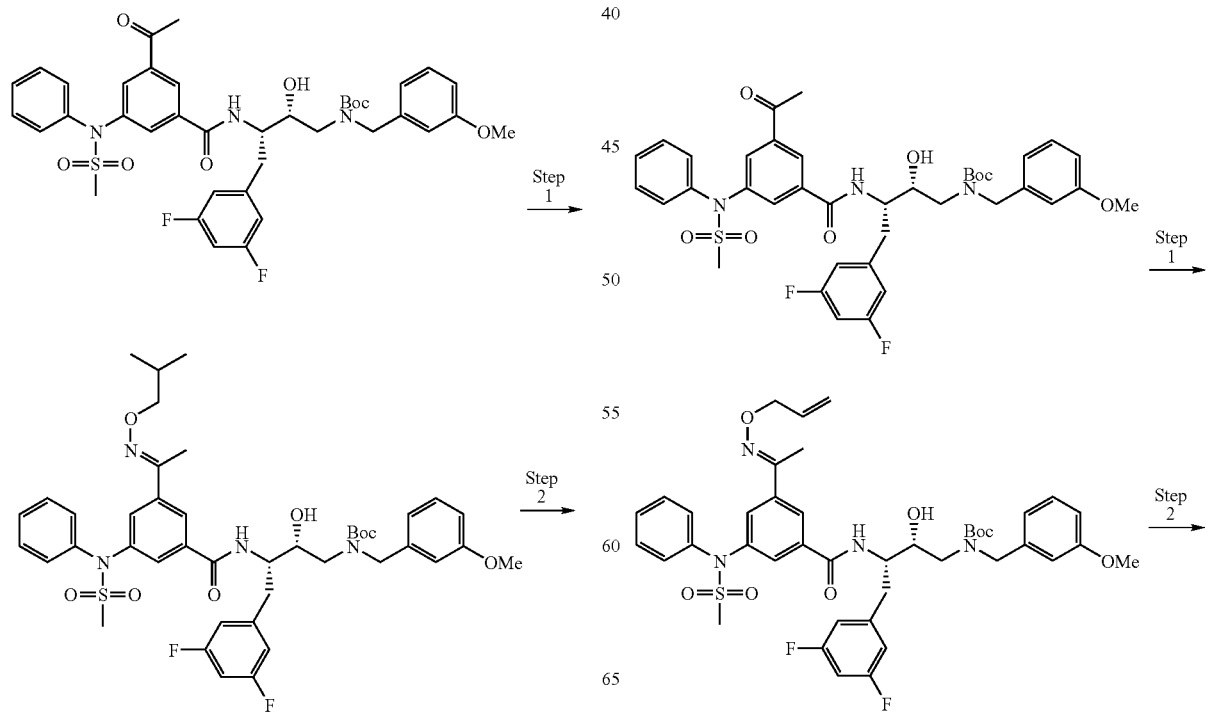

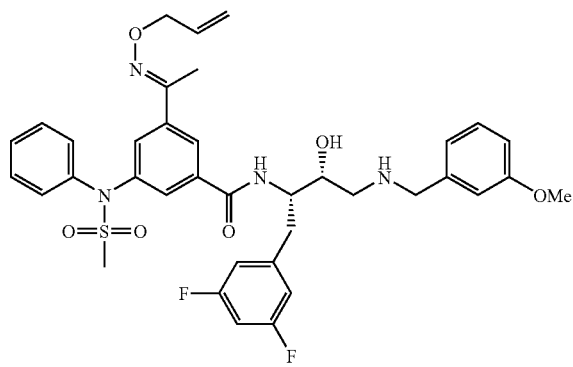

$^1$H NMR (CD$_3$OD, 500 MHz) δ ppm 2.25 (s, 3H), 2.8-3.1 (m, 4H), 3.24 (s, 3H), 3.79 (m, 3H), 3.96 (m, 1H), 4.23 (m, 3H), 4.71 (d, J=5 Hz, 2H), 5.23 (d, J=10 Hz, 1H), 5.33 (d, J=20 Hz, 1H), 6.07 (m, 1H), 6.7-7.5 (m, 12H), 7.65 (s, 1H), 7.80 (s, 1H), 7.87 (s, 1H). HPLC retention time: 1.982 min (method A). MS (ESI) (M+H)$^+$ 707.29.

EXAMPLE 43

N-((2S,3R)-4-(3-methoxybenzylamino)-1-(3,5-difluorophenyl)-3-hydroxybutan-2-yl)-3-(N-phenylmethan-10-ylsulfonamido)-5-((E)-1-(propoxyimino)ethyl)benzamide

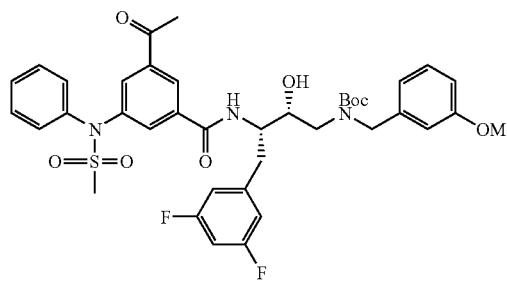

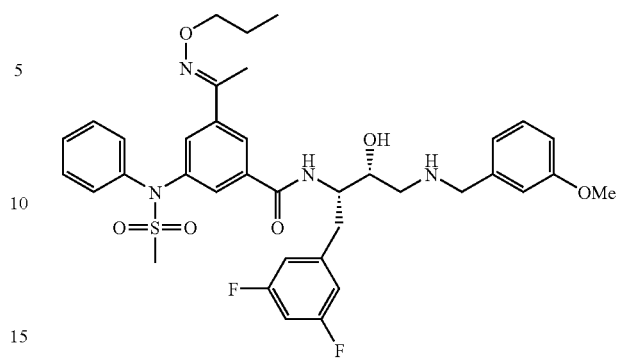

$^1$H NMR (CD$_3$OD, 500 MHz) δ ppm 1.00 (t, J=5 Hz, 3H), 1.76 (q, J=5 Hz, 2H), 2.23 (s, 3H), 2.8-3.1 (m, 4H), 3.79 (s, 3H), 3.97 (m, 1H), 4.15-4.35 (m, 5H), 6.7-7.5 (m, 12H), 7.65 (s, 1H), 7.80 (s, 1H), 7.87 (s, 1H). HPLC retention time: 2.035 min (method A). MS (ESI) (M+H)$^+$ 709.33.

EXAMPLE 44

N$^1$-((2S,3R)-4-(3-methoxybenzylamino)-1-(3,5-difluorophenyl)-3-hydroxybutan-2-yl)-5-acetyl-N$^3$-((R)-1-phenylethyl)isophthalamide TFA salt

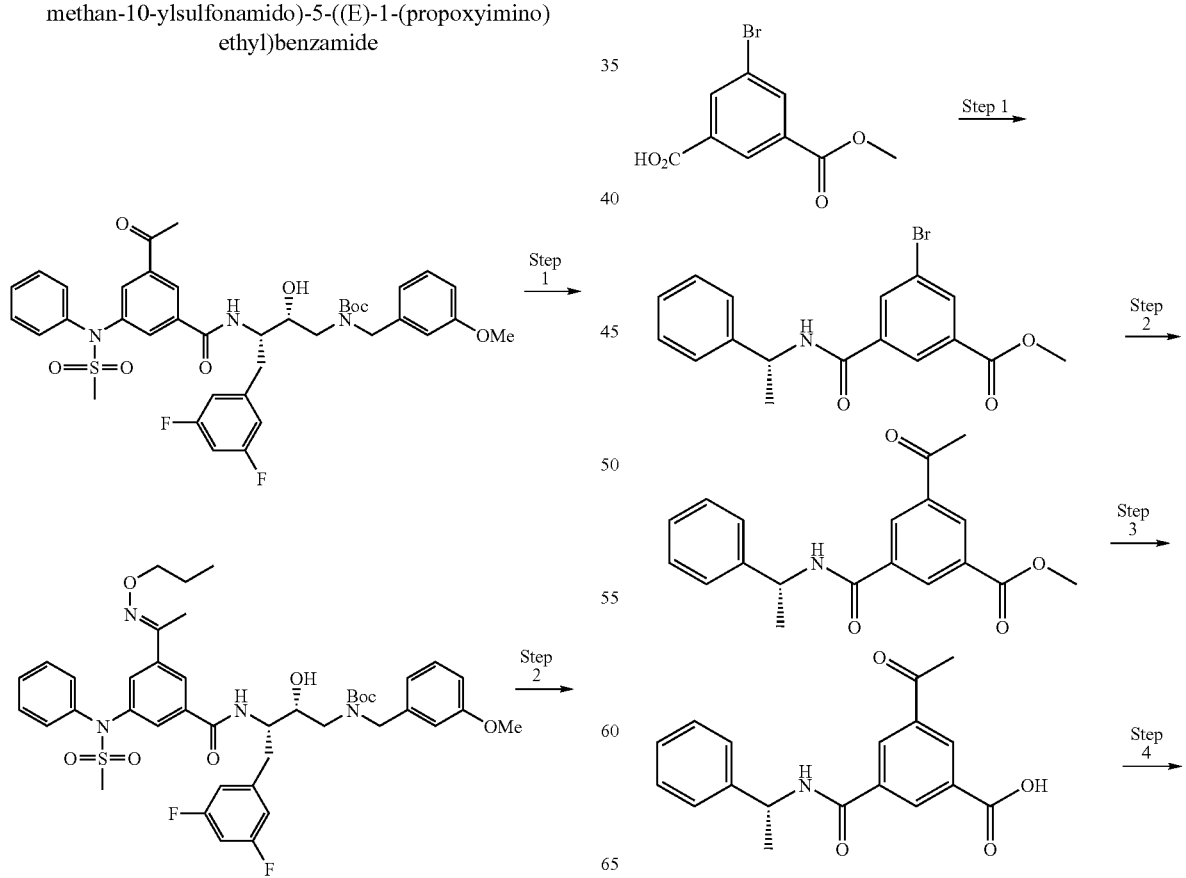

-continued

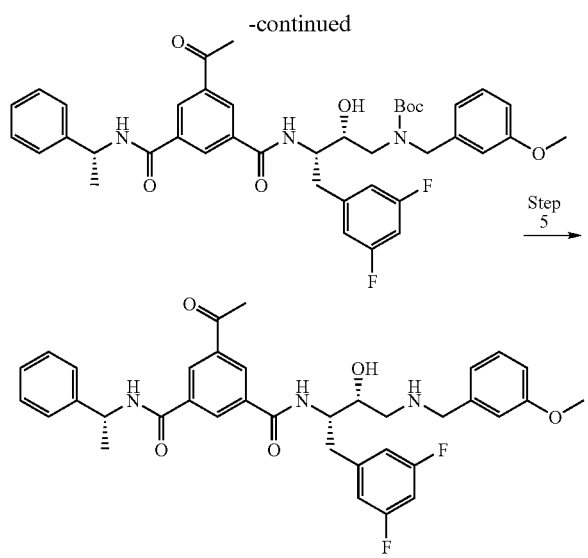

Step 1: Preparation of (R)-methyl 3-bromo-5-((1-phenylethyl)carbamoyl)-benzoate. A mixture of 3-bromo-5-(methoxycarbonyl)benzoic acid (0.60 g, 2.32 mmol) and HATU (1.06 g, 2.78 mmol) in DMF (15 mL) was stirred at room temperature for 10 min. Then (R)-1-phenylethanamine (0.28 g, 0.3 mL, 2.32 mmol) was added and the resulting mixture was stirred at room temperature overnight. The mixture was diluted with ethyl acetate, washed with H$_2$O (3 times) and brine, dried over sodium sulfate, and concentrated under vacuum to give the title compound (0.839 g, 99.9% yield): HPLC retention time: 2.17 min (method A). MS (ESI) (M+H)$^+$ 362/364.

Step 2: Preparation of (R)-methyl 3-acetyl-5-((1-phenylethyl)carbamoyl)benzoate. A mixture of methyl (R)-methyl 3-bromo-5-((1-phenylethyl)carbamoyl)benzoate (839 mg, 2.32 mmol), 1-(vinyloxy)butane (464.7 mg, 0.6 mL, 4.64 mmol), palladium acetate (16.0 mg, 0.070 mmol), DPPP (63.1 mg, 0.0153 mmol) and potassium carbonate (382 mg, 2.78 mmol) in DMF (2.5 mL) and H$_2$O (0.3 mL) in a Smith process vial was heated at 122° C. in microwave for 3 h. The reaction mixture was cooled down to RT and hydrolyzed by addition of 5% HCl slowly. The reaction mixture was worked up by extraction with ethyl acetate and concentration under vacuum. The crude mixture was purified by reverse phase prep HPLC to give the title compound (454 mg, 60% yield): HPLC retention time: 1.83 min (method A). MS (ESI) (M+H)$^+$ 325.00.

Step 3: Preparation of (R)-3-acetyl-5-((1-phenylethyl)carbamoyl)benzoic acid. To a solution of (R)-methyl 3-acetyl-5-((1-phenylethyl)-carbamoyl)benzoate (332 mg, 1.02 mmol) in a mixture of THF (1.4 mL), MeOH (2.8 mL) and H$_2$O (7.0 mL), was added LiOH (73.4 mg, 3.06 mmol) and the mixture was stirred at room temperature for 1 h. The mixture was concentrated and partitioned between ethyl acetate and H$_2$O. The aqueous layer was washed with ethyl acetate twice and acidified with 1N HCl solution to pH around 2~3. The aqueous layer was extracted with ethyl acetate 3 times and the combined organic layers were dried over sodium sulfate and concentrated under vacuum to give the title compound which was ready for next step without further purification (300 mg, 95% yield): HPLC retention time: 1.662 min (method A). MS (ESI) (M+H)$^+$ 311.00.

Step 4: Preparation of tert-butyl 3-methoxybenzyl((2R, 3S)-3-(3-acetyl-5-(benzamido)benzamido)-4-(3,5-difluorophenyl)-2-hydroxybutyl)carbamate. A mixture of (R)-3-acetyl-5-((1-phenylethyl)carbamoyl)benzoic acid (from step 3, 80.0 mg, 0.257 mmol), HATU (117 mg, 0.309 mmol) and Hunig's base (133 mg, 0.2 mL, 1.029 mmol) in DMF (2.0 mL) was stirred for 10 min and then tert-butyl 3-methoxybenzyl((2R,3S)-3-amino-4-(3,5-difluorophenyl)-2-hydroxybutyl)-carbamate (112 mg, 0.257 mmol) was added. The reaction mixture was stirred at room temperature overnight. The reaction mixture was diluted with ethyl acetate and washed with H$_2$O (3 times). The organic layer was dried over sodium sulfate and concentrated under vacuum. The crude product was purified by reverse phase prep HPLC to give the title compound (150 mg): HPLC retention time: 2.350 min (method A). MS (ESI) (M+H)$^+$ 730.40.

Step 5: Preparation of N$^1$-((2S,3R)-4-(3-methoxybenzylamino)-1-(3,5 difluoro-phenyl)-3-hydroxybutan-2-yl)-5-acetyl-N$^3$-((R)-1-phenylethyl)isophthalamide TFA salt. tert-Butyl 3-methoxybenzyl((2R,3S)-3-(3-acetyl-5-(benzamido)-benzamido)-4-(3,5-difluorophenyl)-2-hydroxybutyl)carbamate (12 mg) in MeOH (0.1 ml) was treated with HCl (1 M solution in ether, 0.1 mL) and the mixture was stirred at room temperature overnight. The reaction mixture was concentrated under vacuum and purified by reverse phase prep HPLC to give the title compound (9.5 mg): $^1$H NMR (CD$_3$OD, 500 MHz) δ ppm 1.61 (m, 3H) 2.70 (m, 3H) 2.85 (m, 1H) 3.07 (d, J=10.38 Hz, 1H) 3.19 (m, 1H) 3.41 (m, 1H) 3.78 (m, 3H) 3.99 (m, 1H) 4.26 (m, 3H) 5.28 (dd, J=14.65, 7.32 Hz, 1H) 6.75 (m, 1H) 6.91 (t, J=7.32 Hz, 3H) 7.05 (d, J=9.46 Hz, 2H) 7.35 (m, 6H) 8.33 (d, J=7.63 Hz, 2H) 8.57 (s, 1H). HPLC retention time: 1.853 min (method A). MS (ESI) (M+H)$^+$ 630.30.

EXAMPLE 45

N$^1$-((2S,3R)-4-(3-methoxybenzylamino)-1-(3,5-difluorophenyl)-3-hydroxybutan-2-yl)-5-(1-hydroxyethyl)-N$^3$-((R)-1-phenylethyl)isophthalamide TFA salt

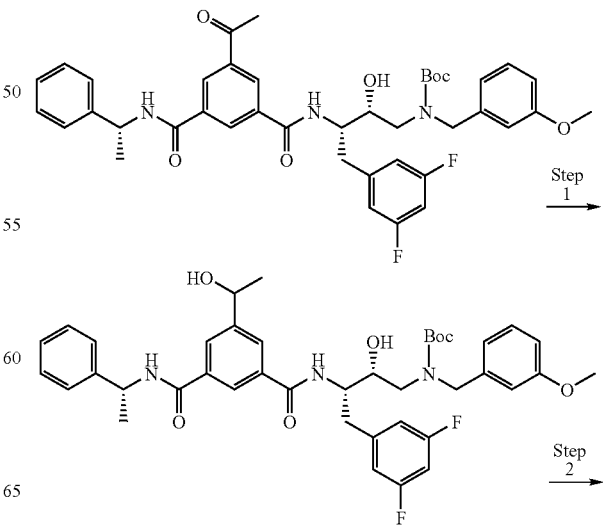

-continued

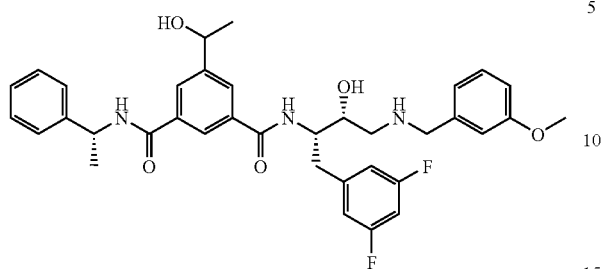

Step 1: Preparation of tert-butyl 3-methoxybenzyl((2R,3S)-3-(3-(benzamido)-5-(1-hydroxyethyl)benzamido)-4-(3,5-difluorophenyl)-2-hydroxybutyl)carbamate. tert-Butyl 3-methoxybenzyl((2R,3S)-3-(3-acetyl-5-(benzamido)-benzamido)-4-(3,5-difluorophenyl)-2-hydroxybutyl)carbamate (15 mg, 0.021 mmol) was dissolved in MeOH (0.1 mL) and sodium borohydride (1.0 mg, 0.028 mmol) was added. The reaction mixture was stirred at room temperature for 2 h. The mixture was concentrated and partitioned between ethyl acetate and H$_2$O. The organic layer was separated and concentrated under vacuum to give the title compound (14 mg): HPLC retention time: 2.267 min (method A). MS (ESI) (M+H)$^+$ 732.39.

Step 2: Preparation of N$^1$-((2S,3R)-4-(3-methoxybenzylamino)-1-(3,5-difluorophenyl)-3-hydroxybutan-2-yl)-5-(1-hydroxyethyl)-N$^3$-((R)-1-phenylethyl)isophthalamide TFA salt. tert-Butyl 3-methoxybenzyl((2R,3S)-3-(3-(benzamido)-5-(1-hydroxy-ethyl)benzamido)-4-(3,5-difluorophenyl)-2-hydroxybutyl)carbamate (12 mg, 0.0164 mmol) in MeOH(0.1 ml) was treated with HCl (1 M solution in ether, 0.1 mL) and the mixture was stirred at room temperature for 12 h. The reaction mixture was concentrated under vacuum and purified by reverse phase prep HPLC to give the title compound (9.5 mg): $^1$H NMR (CD$_3$OD, 500 MHz) δ ppm 1.48 (dd, J=6.41, 1.53 Hz, 2H) 1.60 (m, 3H) 2.87 (m, 1H) 3.07 (s, 1H) 3.20 (s, 1H) 3.36 (m, 1H) 3.78 (d, J=6.71 Hz, 3H) 3.98 (s, 1H) 4.23 (m, 3H) 4.92 (m, 1H) 5.27 (m, 1H) 6.74 (m, 1H) 6.92 (m, 3H) 7.06 (m, 2H) 7.33 (m, 6H) 7.79 (d, J=6.71 Hz, 1H) 7.99 (d, J=4.27 Hz, 2H). HPLC retention time: 1.798 min (method A). MS (ESI) (M+H)$^+$ 632.34.

EXAMPLE 46

N$^1$-((2S,3R)-4-(3-methoxybenzylamino)-1-(3,5-difluorophenyl)-3-hydroxybutan-2-yl)-5-((Z)-1-(allyloxyimino)ethyl)-N$^3$-((R)-1-phenylethyl)isophthalamide TFA salt

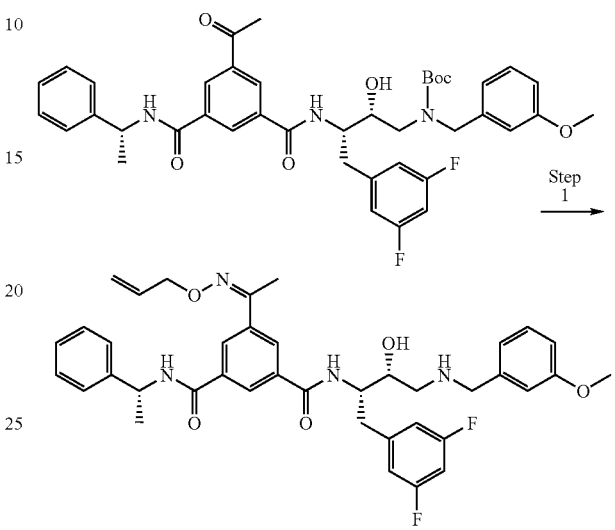

A mixture of tert-butyl 3-methoxybenzyl((2R,3S)-3-(3-acetyl-5-(benzamido)benzamido)-4-(3,5-difluorophenyl)-2-hydroxybutyl)carbamate (9.0 mg, 0.012 mmol) and allylhydroxylamine hydrochloride (2.7 mg, 0.025 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (7.5 mg): $^1$H NMR (CD$_3$OD, 500 MHz) δ ppm 1.60 (m, 3H) 2.31 (s, 3H) 2.88 (m, 1H) 3.07 (m, 1H) 3.20 (m, 1H) 3.37 (m, 1H) 3.76 (d, J=6.71 Hz, 3H) 3.97 (m, 1H) 4.24 (m, 3H) 4.75 (d, J=5.49 Hz, 2H) 5.31 (m, 3H) 6.09 (m, 1H) 6.75 (m, 1H) 6.91 (t, J=6.41 Hz, 3H) 7.06 (m, 2H) 7.33 (m, 6H) 8.06 (d, J=20.14 Hz, 2H) 8.26 (s, 1H). HPLC retention time: 2.062 min (method A). MS (ESI) (M+H)$^+$ 685.34.

EXAMPLE 47

N$^1$-((2S,3R)-4-(3-methoxybenzylamino)-1-(3,5-difluorophenyl)-3-hydroxybutan-2-yl)-5-acetyl-N$^3$-(1-(4-fluorophenyl)ethyl)isophthalamide TFA salt

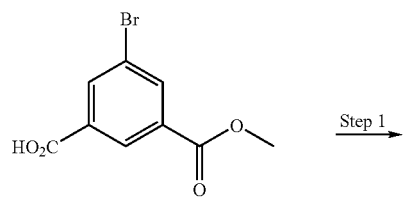

-continued

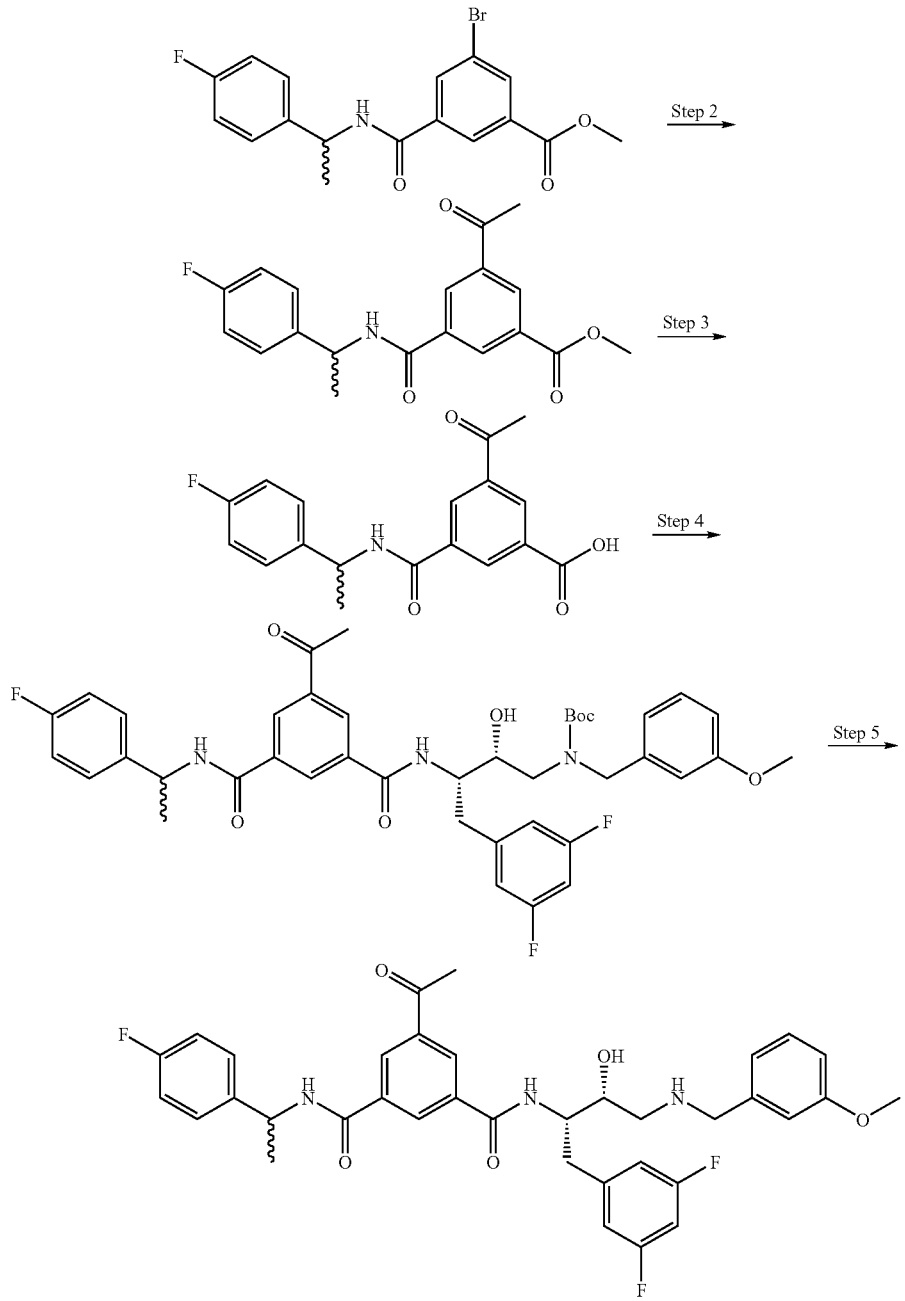

Step 1: Preparation of methyl 3-bromo-5-((1-(4-fluorophenyl)ethyl)-carbamoyl)benzoate. A mixture of 3-bromo-5-(methoxycarbonyl)benzoic acid (0.60 g, 2.32 mmol) and HATU (1.06 g, 2.78 mmol) in DMF (15 mL) was stirred at room temperature for 10 min. Then 1-(4-fluorophenyl)ethanamine (0.323 g, 0.3 mL, 2.32 mmol) was added and the resulting mixture was stirred at room temperature overnight. The mixture was diluted with ethyl acetate, washed with H$_2$O (3 times) and brine, dried over sodium sulfate, and concentrated under vacuum to give the title compound (0.880 g, 99.9% yield): HPLC retention time: 2.098 min (method A). MS (ESD) (M+H)$^+$ 380/382.

Step 2: Preparation of methyl 3-acetyl-5-((1-(4-fluorophenyl)ethyl)-carbamoyl)benzoate. A mixture of methyl 3-bromo-5-((1-(4-fluorophenyl)ethyl)-carbamoyl)benzoate (880 mg, 2.32 mmol), 1-(vinyloxy)butane (464.7 mg, 0.6 mL, 4.64 mmol), palladium acetate (16.0 mg, 0.070 mmol), DPPP (63.1 mg, 0.0153 mmol) and potassium carbonate (382 mg, 2.78 mmol) in DMF (2.5 mL) and H$_2$O (0.3 mL) in a Smith process vial was heated at 122° C. in microwave for 3 h. The reaction mixture was cooled down to RT and hydrolyzed by addition of 5% HCl slowly. The reaction mixture was worked up by extraction with ethyl acetate and concentration under vacuum. The crude mixture was purified by reverse phase prep HPLC to give the title compound (520 mg, 65.4% yield): HPLC retention time: 1.88 min (method A). MS (ESI) (M+H)+ 343.00.

Step 3: Preparation of 3-acetyl-5-((1-(4-fluorophenyl)ethyl)carbamoyl)benzoic acid. To a solution of methyl 3-acetyl-5-((1-(4-fluorophenyl)ethyl)-carbamoyl)benzoate (302 mg, 0.88 mmol) in a mixture of THF (1.2 mL), MeOH (2.4 mL) and H$_2$O (6.0 mL), was added LiOH (63.3 mg, 2.64 mmol) and the mixture was stirred at room temperature for 1 h. The mixture was concentrated and partitioned between ethyl acetate and H$_2$O. The aqueous layer was washed with ethyl acetate twice and acidified with 1N HCl solution to pH around 2~3. The aqueous layer was extracted with ethyl acetate 3 times and the combined organic layers were dried over sodium sulfate and concentrated under vacuum to give the title compound which was ready for next step without further purification (278 mg, 96% yield): HPLC retention time: 1.718 min (method A). MS (ESI) (M+H)+ 329.00.

Step 4: Preparation of [(2R,3S)-3-{3-Acetyl-5-[1-(4-fluoro-phenyl)-ethylcarbamoyl]-benzoylamino}-4-(3,5-difluoro-phenyl)-2-hydroxy-butyl]-(3-methoxy-benzyl)-carbamic acid tert-butyl ester. A mixture of 3-acetyl-5-((1-(4-fluorophenyl)ethyl)carbamoyl)benzoic acid (from step 3, 85.0 mg, 0.257 mmol), HATU (117 mg, 0.309 mmol) and Hunig's base (133 mg, 0.2 mL, 1.029 mmol) in DMF (2.0 mL) was stirred for 10 min and then tert-butyl 3-methoxybenzyl((2R,3S)-3-amino-4-(3,5-difluorophenyl)-2-hydroxybutyl)-carbamate (112 mg, 0.257 mmol) was added. The reaction mixture was stirred at room temperature overnight. The reaction mixture was diluted with ethyl acetate and washed with H$_2$O (3 times). The organic layer was dried over sodium sulfate and concentrated under vacuum. The crude product was purified by reverse phase prep HPLC to give the title compound (150 mg): HPLC retention time: 2.265 min (method A). MS (ESI) (M+H)+ 748.47.

Step 5: Preparation of N$^1$-((2S,3R)-4-(3-methoxybenzylamino)-1-(3,5-difluoro-phenyl)-3-hydroxybutan-2-yl)-5-acetyl-N$^3$-(1-(4-fluorophenyl)ethyl)isophthal-amide TFA salt. tert-Butyl 3-methoxybenzyl((2R,3S)-3-(3-acetyl-5-(benzamido)-benzamido)-4-(3,5-difluorophenyl)-2-hydroxybutyl)carbamate (8.0 mg) in MeOH (0.1 ml) was treated with HCl (1 M solution in ether, 0.1 mL) and the mixture was stirred at room temperature overnight. The reaction mixture was concentrated under vacuum and purified by reverse phase prep HPLC to give the title compound (6.0 mg): $^1$H NMR (CD$_3$OD, 500 MHz) δ ppm 1.61 (dd, J=7.17, 3.20 Hz, 3H) 2.68 (s, 3H) 2.88 (m, 1H) 3.07 (dd, J=12.51, 8.24 Hz, 1H) 3.22 (d, J=12.51 Hz, 1H) 3.37 (dd, J=14.19, 3.20 Hz, 1H) 3.77 (m, 3H) 4.00 (m, 1H) 4.26 (m, 3H) 5.28 (m, 1H) 6.75 (m, 1H) 6.91 (d, J=7.02 Hz, 3H) 7.07 (m, 4H) 7.30 (m, 1H) 7.45 (m, 2H) 8.34 (dd, J=7.93, 1.83 Hz, 2H) 8.56 (d, J=2.14 Hz, 1H). HPLC retention time: 1.858 min (method A). MS (ESI) (M+H)+ 648.31.

EXAMPLE 48

N$^1$-((2S,3R)-4-(3-methoxybenzylamino)-1-(3,5-difluorophenyl)-3-hydroxybutan-2-yl)-N$^3$-(1-(4-fluorophenyl)ethyl)-5-(1-hydroxyethyl)isophthal-amide TFA salt

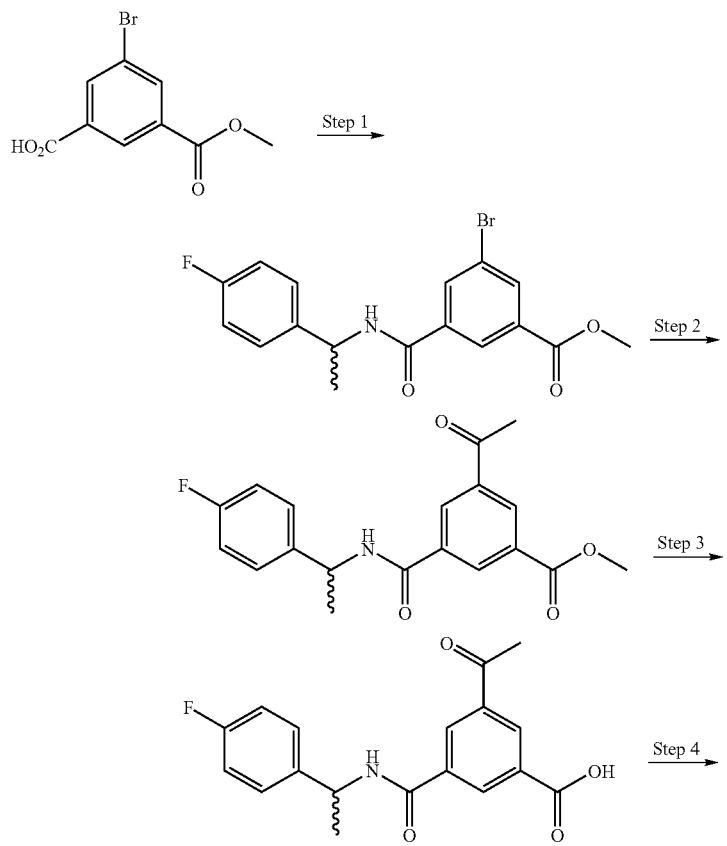

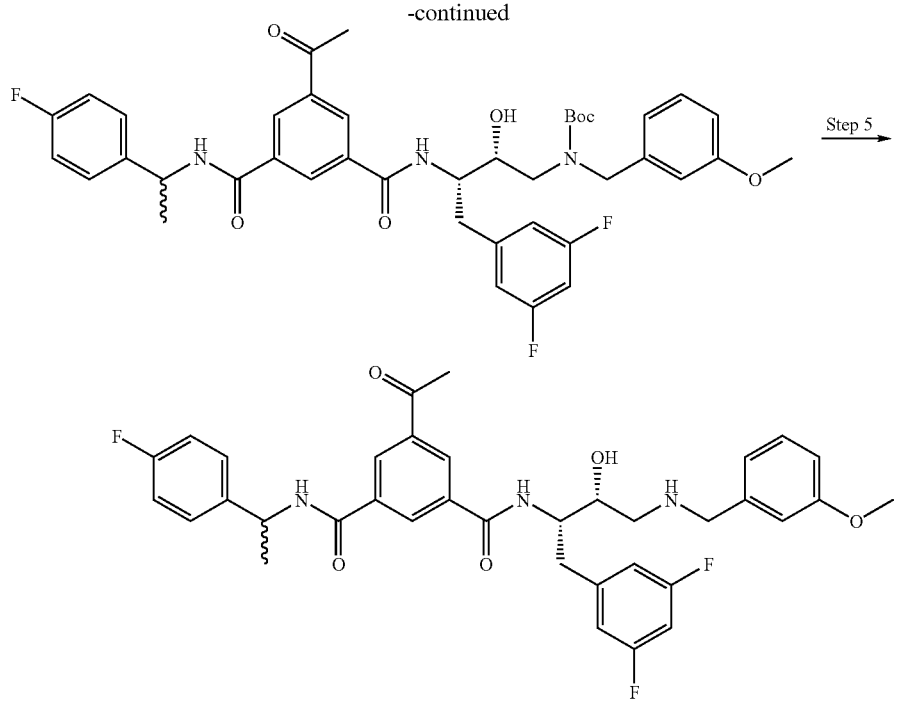

Step 1: Preparation of {(2R,3S)-4-(3,5-Difluoro-phenyl)-3-[3-[1-(4-fluoro-phenyl)-ethylcarbamoyl]-5-(1-hydroxy-ethyl)-benzoylamino]-2-hydroxy-butyl}-(3-methoxy-benzyl)-carbamic acid tert-butyl ester. [(2R,3S)-3-{3-Acetyl-5-[1-(4-fluoro-phenyl)-ethylcarbamoyl]-benzoyl-amino}-4-(3,5-difluoro-phenyl)-2-hydroxy-butyl]-(3-methoxy-benzyl)-carbamic acid tert-butyl ester (10 mg, 0.0134 mmol) was dissolved in MeOH (0.1 mL) and sodium borohydride (0.68 mg, 0.0179 mmol) was added. The reaction mixture was stirred at room temperature for 2 h. The mixture was concentrated and partitioned between ethyl acetate and H$_2$O. The organic layer was separated and concentrated under vacuum to give the title compound (10 mg): HPLC retention time: 2.243 min (method A). MS (ESI) (M+H)$^+$ 750.40.

Step 2: Preparation of N$^1$-((2S,3R)-4-(3-methoxybenzylamino)-1-(3,5-difluorophenyl)-3-hydroxybutan-2-yl)-N$^3$-(1-(4-fluorophenyl)ethyl)-5-(1-hydroxyethyl)isophthalamide TFA salt. {(2R,3S)-4-(3,5-Difluoro-phenyl)-3-[3-[1-(4-fluoro-phenyl)-ethyl-carbamoyl]-5-(1-hydroxy-ethyl)-benzoylamino]-2-hydroxy-butyl}-(3-methoxy-benzyl)-carbamic acid tert-butyl ester (8.0 mg, 0.011 mmol) in MeOH (0.1 ml) was treated with HCl (1 M solution in ether, 0.1 mL) and the mixture was stirred at room temperature for 12 h. The reaction mixture was concentrated under vacuum and purified by reverse phase prep HPLC to give the title compound (6.0 mg): $^1$H NMR (CD$_3$OD, 500 MHz) δ ppm 1.48 (m, 3H) 1.59 (m, 3H) 2.88 (m, 1H) 3.08 (m, 1H) 3.20 (m, 1H) 3.37 (d, J=11.29 Hz, 1H) 3.78 (d, J=5.49 Hz, 3H) 3.98 (m, 1H) 4.21 (m, 3H) 4.92 (m, 1H) 5.25 (m, 1H) 6.75 (m, 1H) 6.93 (m, 3H) 7.07 (m, 4H) 7.32 (q, J=7.93 Hz, 1H) 7.44 (m, 2H) 7.79 (d, J=4.58 Hz, 1H) 7.98 (s, 2H). HPLC retention time: 1.805 min (method A). MS (ESI) (M+H)$^+$ 650.34.

EXAMPLE 49

N$^1$-((2S,3R)-4-(3-methoxybenzylamino)-1-(3,5-difluorophenyl)-3-hydroxybutan-2-yl)-5-((Z)-1-(allyloxyimino)ethyl)-N$^3$-(1-(4-fluorophenyl)ethyl)isophthalamide TFA salt

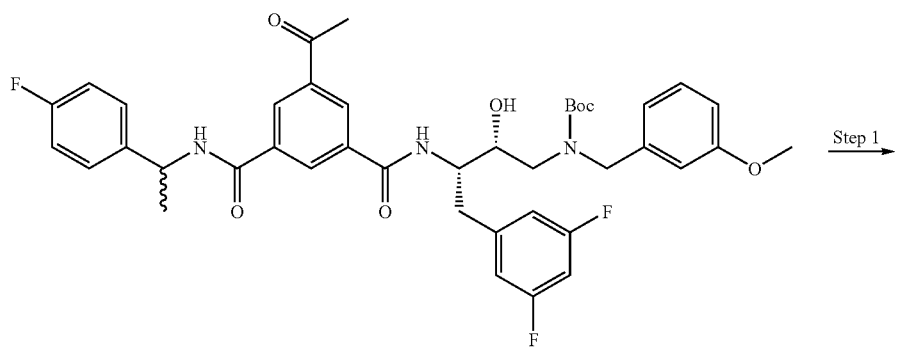

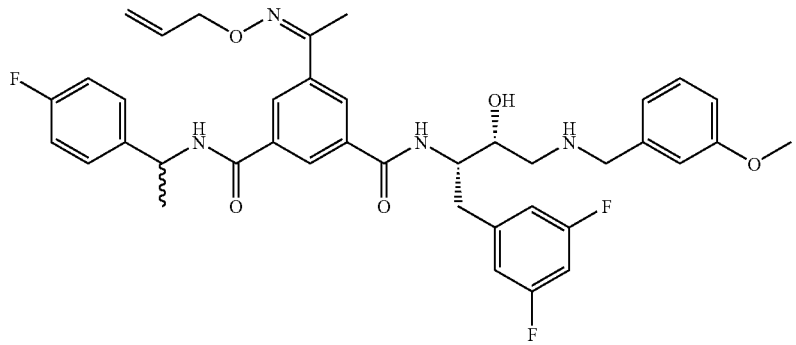

A mixture of [(2R,3S)-3-{3-Acetyl-5-[1-(4-fluoro-phenyl)-ethylcarbamoyl]-benzoylamino}-4-(3,5-difluoro-phenyl)-2-hydroxy-butyl]-(3-methoxy-benzyl)-carbamic acid tert-butyl ester (8.0 mg, 0.011 mmol) and allylhydroxylamine hydrochloride (2.4 mg, 0.022 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (6.5 mg): $^1$H NMR (CD$_3$OD, 500 MHz) δ ppm 1.60 (m, 3H) 2.32 (s, 3H) 2.86 (m, 1H) 3.07 (dd, J=12.97, 7.78 Hz, 1H) 3.20 (m, 1H) 3.36 (m, 1H) 3.77 (d, J=6.41 Hz, 3H) 3.97 (m, 1H) 4.25 (m, 3H) 4.76 (m, 2H) 5.30 (m, 3H) 6.09 (m, 1H) 6.76 (m, 1H) 6.92 (m, 3H) 7.07 (m, 4H) 7.31 (m, 1H) 7.45 (m, 2H) 8.06 (m, 2H) 8.25 (s, 1H)HPLC retention time: 2.060 min (method A). MS (ESI) (M+H)$^+$ 703.38.

EXAMPLE 50

$N^1$-((2S,3R)-4-(3-methoxybenzylamino)-1-(3,5-difluorophenyl)-3-hydroxybutan-2-yl)-$N^3$-(1-(4-fluorophenyl)ethyl)-5-((Z)-1-(methoxyimino)ethyl) isophthalamide TFA salt

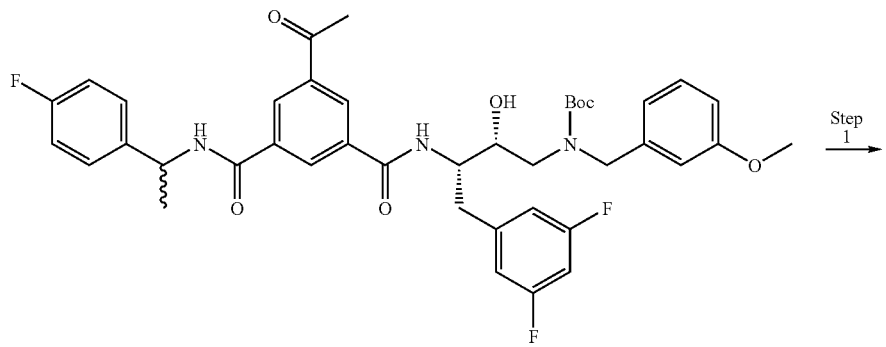

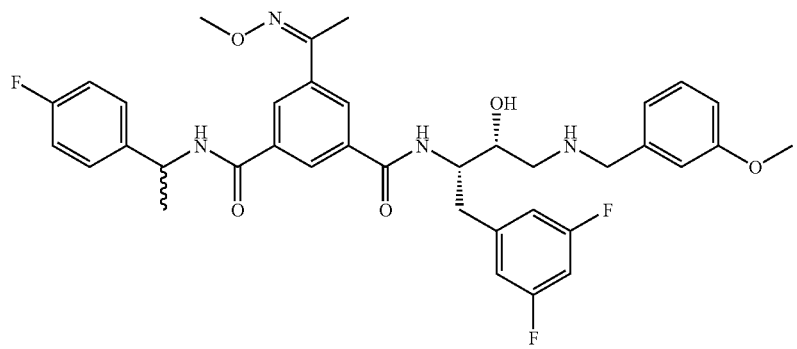

A mixture of [(2R,3S)-3-{3-Acetyl-5-[1-(4-fluoro-phenyl)-ethyl-carbamoyl]-benzoylamino}-4-(3,5-difluoro-phenyl)-2-hydroxy-butyl]-(3-methoxybenzyl)-carbamic acid tert-butyl ester (8 mg, 0.011 mmol) and methoxyamine hydrochloride (1.8 mg, 0.022 mmol) in ethanol (0.1 mL) was heated at 80° C. for 3 h. The reaction mixture was cooled down to room temperature, treated with HCl (1.0 M solution in ether, 0.1 mL) and stirred for overnight. The mixture was concentrated and purified by reverse phase prep HPLC to give the title compound (6.0 mg): $^1$H NMR (CD$_3$OD, 500 MHz) δ ppm 1.60 (m, 2.75 Hz, 3H) 2.28 (s, 3H) 2.87 (m, 1H) 3.08 (m, 1H) 3.20 (m, 1H) 3.38 (m, 1H) 3.77 (d, J=5.80 Hz, 3H) 3.98 (m, 1H) 4.04 (s, 3H) 4.24 (m, 3H) 5.26 (m, 1H) 6.76 (m, 1H) 6.92 (m, 3H) 7.06 (m, 4H) 7.31 (q, J=8.24 Hz, 1H) 7.44 (m, 2H) 8.06 (m, 2H) 8.26 (m, 1H)HPLC retention time: 1.983 min (method A). MS (ESI) (M+H)$^+$ 677.32.

BIOLOGICAL METHODS

There are a number of methods by which inhibitors of the BACE enzyme can be identified experimentally. The enzyme can be obtained from membrane samples from natural tissues or cultured cells or can be expressed recombinantly in a host cell by well known methods of molecular biology. The whole enzyme or a portion thereof can be expressed, for example, in bacterial, insect or mammalian cells to obtain a catalytically active enzyme species. The enzymatic activity and/or ligand binding capability of the enzyme can be assessed within these membrane samples, or the enzyme can be purified to varying extents. As an illustrative example, the nucleic acid sequence encoding the pro and catalytic domains of human BACE can be appended on the 5' end with an untranslated and signal sequence from the gene for acetylcholinesterase, and on the 3' end with a sequence encoding a poly-histidine tag. This cDNA can then be expressed in *Drosophila melanogaster* S2 cells in which the signal and pro sequences of the transcribed/translated protein are removed by cellular proteases and the catalytic domain, appended by a C-terminal poly-histidine tag, is secreted out into the cellular medium. The enzyme can then be purified from the culture medium by nickel affinity chromatography by methods well known to those trained in the art [Mallender, W. et al., (2001) "Characterization of recombinant, soluble beta-secretase from an insect cell expression system." *Mol. Pharmacol.* 59: 619-626]. Similar strategies for expressing and purifying various forms of BACE in bacterial, mammalian and other cell types would be known to one skilled in the art. A preferred method for determining the potency of a test compound in binding to the BACE enzyme is by motoring the displacement of a suitable radioligand.

Radioligand displacement assays with a radiolabeled BACE inhibitor (WO 2004 013098, compound 3, where the methoxy group is substituted for C($^3$H)$_3$) were carried out using standard methods (Keen, M. (1999) in *Receptor Binding Techniques* (Walker, J. M. ed) p. 106 Humana Press, Totowa, N.J.). The HEK293-9B.A1 cell line, which overexpresses the BACE1 enzyme, was derived from HEK293 cells (Simmons, N. L. (1990) A cultured human renal epitheloid cell line responsive to vasoactive intestinal peptide. *Exp. Physiol.* 75:309-19.) by RAGE™ (Harrington, J. J. et al. (2001) Creation of genome-wide protein expression libraries using random activation of gene expression. *Nat. Biotechnol.* 19:440-5; U.S. Pat. Nos. 6,410,266 and 6,361,972). T225 flask cultures of HEK293-9B.A1 were grown to 80% confluency in DMEM supplemented with 2 mM L-glutamine, 10 μg/ml penicillin, 10 μg/ml streptomycin, 3 μg/ml puromycin, 100 nM methotrexate, and 10% fetal bovine serum (Invitrogen, Carlsbad, Calif.), harvested, and resuspended at 2×10$^8$ cells per 10 ml of lysis buffer consisting of 50 mM HEPES pH 7.0 containing a protease inhibitor cocktail of AEBSF 104 μM, aprotinin 80 nM, leupeptin 2 μM, bestatin 4 μM, pepstatin A 1.5 μM, and E-64 1.4 μM (0.1% of protease inhibitor cocktail P8340, Sigma-Aldrich, St. Louis, Mo.) at 4° C. The resuspended cells were homogenized using a Polytron (Brinkman, Westbury, N.Y.) at setting 6 for 10 sec., then centrifuged at 48,000×g for 10 min. The resulting pellet was washed by repeating the resuspension, homogenization and centrifugation steps. The final pellet was resuspended in buffer at 4° C. to yield a total protein concentration of 5 mg/ml, then aliquots were frozen in liquid nitrogen for further storage at −70° C. Immediately before carrying out a binding assay, an aliquot of cell homogenate was thawed and diluted to a concentration of 100 μg/ml in assay buffer consisting of 50 mM HEPES pH 5.0 and 0.1% CHAPSO. Assays were initiated in polypropylene 96-well plates (Costar, Cambridge, Mass.) by the addition of 200 μl of cell homogenate to 50 μl of assay buffer containing 1 nM radioligand (WO 2004 013098, compound 3, where the methoxy group is substituted for C($^3$H)$_3$: 80 Ci/mMol) and various concentrations of unlabelled compounds, and incubated for 1.5 hr. at 25° C. Separation of bound from free radioligand was by filtration on GFF glass fiber filters (Innotech Biosystems International, Lansing, Mich.) using an Innotech cell harvester. Filters were washed three times with 0.3 ml of phosphate buffered saline pH 7.0 at 4° C. and assessed for radioactivity using a Wallac 1450 Microbeta liquid scintillation counter (PerkinElmer, Boston, Mass.). Ki values of competing compounds were derived through Cheng-Prussoff correction of IC50 values calculated using XLfit (IDBS, Guildford, UK).

Abbreviations:
AEBSF: 4-(2-Aminoethyl)benzenesulfonyl fluoride hydrochloride
CHAPSO: 3-[(3-Cholamidopropyl)dimethylammonio]-2-hydroxy-1-propanesulfonate
D-MEM: Dulbecco's modified eagle medium
HEPES: 4-(2-Hydroxyethyl)piperazine-1-ethanesulfonic acid
RAGE™: Random Activation of Gene Expression™

The activity of specific compounds described herein and tested in the above assay is provided in Table 1.

TABLE 1

| Example No. | Activity Rating[a] |
|---|---|
| 1 | +++ |
| 2 | +++ |
| 3 | +++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | ++ |
| 17 | ++ |
| 18 | ++ |
| 19 | ++ |
| 20 | + |
| 21 | ++ |
| 22 | +++ |

TABLE 1-continued

| Example No. | Activity Rating[a] |
|---|---|
| 23 | +++ |
| 24 | +++ |
| 25 | +++ |
| 26 | +++ |
| 27 | ++ |
| 28 | +++ |
| 29 | ++ |
| 30 | +++ |
| 31 | +++ |
| 32 | ++ |
| 33 | ++ |
| 34 | +++ |
| 35 | +++ |
| 36 | +++ |
| 37 | +++ |
| 38 | +++ |
| 39 | +++ |
| 40 | +++ |
| 41 | ++ |
| 42 | +++ |
| 43 | +++ |
| 44 | +++ |
| 45 | +++ |
| 46 | +++ |
| 47 | +++ |
| 48 | +++ |
| 49 | ++ |
| 50 | +++ |

[a]Activity based on $IC_{50}$ values:
+++ = <0.1 μM
++ = 0.1-1.0 μM
+ = >1.0 μM In Vitro Assay to Identify β-Secretase Inhibitor Based on the Inhibition of Aβ Formation from Membrane Preparations.

An isolated membrane fraction which contains functionally active β-secretase and β-APP substrates can generate β-secretase cleavage products including Aβ (Roberts, S. B.; Hendrick, J. P.; Vinitsky, A.; Lewis, M.; Smith, D. W.; Pak, R. PCT Publication WO 01/0175435; Fechteler, K.; Kostka, M.; Fuchs, M. Patent Application No. DE 99-19941039; Shearman, M.; Beher, D. et al., *Biochemistry,* 2000, 39, 8698-8704; Zhang, L. Song, L. et al., *Biochemistry* 2001, 40, 5049-5055). An isolated membrane fraction can be prepared from human derived cell lines such as HeLa and H4 which have been transfected with wild type or mutant forms of β-APP or a human alkaline phosphatase β-APP fusion construct, and stably express high levels of β-secretase substrates. The endogenous β-secretase present in the isolated membranes prepared at 0-4° C. cleaves the β-APP substrates when the membranes are shifted from 0-4 to 37° C. Detection of the cleavage products including Aβ can be monitored by standard techniques such as immunoprecipitation (Citron, M.; Diehl, T. S. et al., *Proc. Natl. Acad. Sci. USA,* 1996, 93, 13170-13175), western blot (Klafki, H.-W.; Ambramowski, D. et al., *J. Biol. Chem.* 1996, 271, 28655-28659), enzyme linked immunosorbent assay (ELISA) as demonstrated by Seubert, P.; Vigo-Pelfrey, C. et al., *Nature,* 1992, 359, 325-327, or by a preferred method using time-resolved fluorescence of the homogeneous sample containing membranes and Aβ (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry,* 2000, 39, 8698-8704). The Aβ present in a homogeneous sample containing membranes can be detected by time-resolved fluorescence with two antibodies that recognize different epitopes of Aβ. One of the antibodies recognizes an epitope that is present in Aβ but not present in the precursor fragments; preferably the antibody binds the carboxyl terminus of Aβ generated by the β-secretase cleavage. The second antibody binds to any other epitope present on Aβ. For example, antibodies that bind the N-terminal region (e.g., 26D6-B2-B3® SIBIA Neurosciences, La Jolla, Calif.) or bind the C-terminal end (e.g., 9S3.2® (antibody, Biosolutions, Newark, Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of β-secretase. The isolated membrane assay can be used to identify candidate agents that inhibit the activity of β-secretase cleavage and Aβ production.

A typical membrane-based assay requires 45 μg membrane protein per well in a 96- or 384-well format. Membranes in a neutral buffer are combined with the test compound and shifted from 0-4 to 37° C. Test agents may typically consist of synthetic compounds, secondary metabolites from bacterial or fungal fermentation extracts, or extracts from plant or marine samples. All synthetic agents are initially screened at doses ranging from 10-100 μM or in the case of extracts at sufficient dilution to minimize cytotoxicity. Incubation of the membranes with the test agent will continue for approximately 90 minutes at which time fluorescence labeled antibodies are added to each well for Aβ quantitation. The time-resolved fluorescence detection and quantitation of Aβ is described elsewhere (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry,* 2000. 39, 8698-8704). Results are obtained by analysis of the plate in a fluorescence plate reader and comparison to the mock treated membranes and samples in which known amounts of Aβ were added to construct a standard concentration curve. A positive acting compound is one that inhibits the Aβ relative to the control sample by at least 50% at the initial tested concentration. Compounds of the present application are considered active when tested in the above assay if the $IC_{50}$ value for the test compound is less than 50 μM. A preferred $IC_{50}$ value is less than 1 μM. A more preferred $IC_{50}$ value is less than 0.1 μM. If a compound is found to be active then a dose response experiment is performed to determine the lowest dose of compound necessary to elicit the inhibition of the production of Aβ.

In Vivo Assays for the Determination of Aβ Reduction by a β-Secretase Inhibitor.

In vivo assays are available to demonstrate the inhibition of β-secretase activity. In these assays, animals, such as mice, that express normal levels of APP, β- and γ-secretase or are engineered to express higher levels of APP and hence Aβ can be used to demonstrate the utility of β-secretase inhibitors, as demonstrated with γ-secretase inhibitors [Dovey, H. et al., (2001), J. Neurochem. 76: 173-181]. In these assays, β-secretase inhibitors are administered to animals and Aβ levels in multiple compartments, such as plasma, cerebral spinal fluid, and brain extracts, are monitored for Aβ levels using methods previously outlined. For instance, Tg2576 mice, which overexpress human APP, are administered β-secretase inhibitors by oral gavage at doses that will cause measurable Aβ lowering, typically less than 100 mg/kg. Three hours after dosing plasma, brain, and CSF are collected, frozen in liquid nitrogen, and stored at −80° C. until analysis. For Aβ detection, plasma is diluted 15-fold in PBS with 0.1% Chaps while CSF is diluted 15-fold in 1% Chaps with protease inhibitors (5 μg/ml leupeptin, 30 μg/ml aprotinin, 1 mM phenylmethylsulfonylfluoride, 1 μM pepstatin). Brains are homogenized in 1% Chaps with protease inhibitors using 24 ml solution/g brain tissue. Homogenates were then centrifuged at 100,000×g for 1 hr at 4° C. The resulting supernatants were then diluted 10-fold in 1% Chaps with protease inhibitors. Aβ levels in the plasma, CSF, and brain lysate can then be measured using time-resolved fluorescence of the homogenous sample or one of the other methods previously described.

A β-secretase inhibitor is considered active in one of the above in vivo assays if it reduces Aβ by at least 50% at a dosage of 100 mg/kg.

DOSAGE AND FORMULATION

The compounds of the present application can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present application can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this application can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present application will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present application may be administered in a single daily dose, or the total daily dosage may be administered in divided doses of two, three, or four times daily.

The compounds for the present application can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present application, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices. Suitable pharmaceutical carriers are described in Remington's Pharmaceutical Sciences, Mack Publishing Company, a standard reference text in this field.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present disclosure can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present disclosure may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present disclosure may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

What is claimed is:

1. A compound of Formula (I); or a stereoisomer thereof

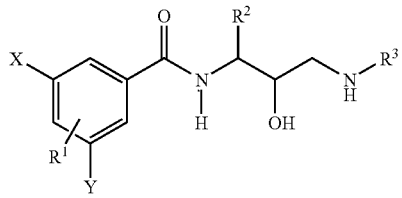
(I)

wherein
X is

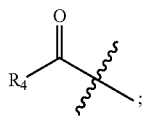
;

Y is —C(O)NR$^6$R$^7$, C(O)NH—C$_{1-3}$alkyl-aryl, —SO$_2$R$^6$, —NR$^6$S(O)$_m$R$^7$,

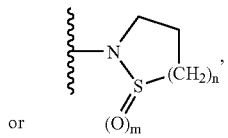
or wherein aryl=phenyl;
R$^1$ is H, or C$_{1-4}$alkyl;
R$^2$ and R$^3$ each are —C$_{1-4}$alkyl-aryl, wherein aryl=phenyl;
R$^4$, R$^6$ and R$^7$ are each independently C$_{1-6}$ alkyl; and
m=n=2;
or a nontoxic pharmaceutically acceptable salt thereof.

2. The compound according to claim 1 of Formula (Ia)

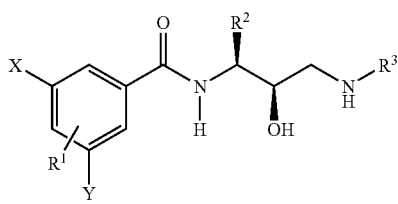
(Ia)

wherein
X is

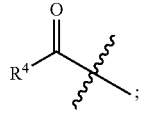
;

Y is —C(O)NR$^6$R$^7$, C(O)NH—C$_{1-3}$alkyl-aryl, —SO$_2$R$^6$, —NR$^6$S(O)$_m$R$^7$, or

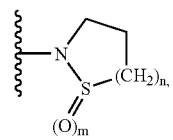

wherein aryl=phenyl;
R$^1$ and H, or C$_{1-4}$alkyl;
R$^2$ and R$^3$ each are —C$_{1-4}$alkyl-aryl, wherein aryl=phenyl;
R$^4$, R$^6$ and R$^7$ are each independently C$_{1-6}$ alkyl; and
m=n=2;
or a nontoxic pharmaceutically acceptable salt thereof.

3. The compound according to claim 2 wherein R$^2$ is benzyl.

4. The compound according to claim 3 wherein R$^3$ is benzyl.

5. The compound according to claim 4 wherein R$^1$ is H.

6. The compound according to claim 5 wherein Y is C(O)N(n-Pr)$_2$ or

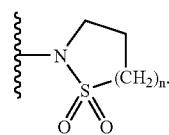

7. The compound according to claim 6 wherein X is —C(O)Me.

8. The compound which is selected from the group consisting of:

N$^1$-((2S,3R)-4-(3-methoxybenzylamino)-1-(3,5-difluorophenyl)-3-hydroxybutan-2-yl)-5-acetyl-N$^3$,N$^3$-dipropylisophthalamide TFA salt;

N$^1$-((2S,3R)-4-(3-methoxybenzylamino)-1-(3,5-difluorophenyl)-3-hydroxybutan-2-yl)-5-acetyl-N$^3$-methyl-N$^3$-propylisophthalamide TFA salt; and N$^1$-((2S,3R)-4-(3-methoxybenzylamino)-1-(3,5-difluorophenyl)-3-hydroxybutan-2-yl)-3-acetyl-5-(N-phenylmethan-10-ylsulfonamodo)benzamide TFA salt.

9. A pharmaceutical composition comprising a therapeutically effective amount of a compound of claim 1 in association with a pharmaceutically acceptable carrier or diluent.

* * * * *

UNITED STATES PATENT AND TRADEMARK OFFICE
CERTIFICATE OF CORRECTION

PATENT NO. : 7,476,764 B2  Page 1 of 1
APPLICATION NO. : 11/494145
DATED : December 23, 2008
INVENTOR(S) : Roland D. Hintzman It is certified that error appears in the above-identified patent and that said Letters Patent is hereby corrected as shown below:

Column 3, line 41 "fabric scam tape" should be changed to --fabric seam tape--

Column 4, line 1 "chafing skins" should be changed to --chafing skirts--

Signed and Sealed this

Twenty-fourth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO.       : 7,476,764 B2                                        Page 1 of 1
APPLICATION NO.  : 11/494145
DATED            : January 13, 2009
INVENTOR(S)      : Roland D. Hintzman It is certified that error appears in the above-identified patent and that said Letters Patent is hereby corrected as shown below:

Column 3, line 41 "fabric scam tape" should be changed to --fabric seam tape--

Column 4, line 1 "chafing skins" should be changed to --chafing skirts--

This certificate supersedes the Certificate of Correction issued February 24, 2009.

Signed and Sealed this

Seventeenth Day of March, 2009

JOHN DOLL
*Acting Director of the United States Patent and Trademark Office*